(12) United States Patent
Baeten et al.

(10) Patent No.: US 11,219,579 B2
(45) Date of Patent: Jan. 11, 2022

(54) HEATING OF DENTAL MATERIALS USING OVERTONE SIGNATURES, ABSORBING DYES AND MATERIAL PROPERTIES

(71) Applicant: INTER-MED, INC., Racine, WI (US)

(72) Inventors: John Baeten, Oak Creek, WI (US); Alex Johnson, Racine, WI (US); Brett Arand, Milwaukee, WI (US)

(73) Assignee: Inter-Med, Inc., Racine, WI (US)

( * ) Notice: Subject to any disclaimer, the term of this patent is extended or adjusted under 35 U.S.C. 154(b) by 0 days.

(21) Appl. No.: 16/804,138

(22) Filed: Feb. 28, 2020

(65) Prior Publication Data
US 2020/0197263 A1 Jun. 25, 2020

Related U.S. Application Data

(63) Continuation of application No. 16/246,205, filed on Jan. 11, 2019, now Pat. No. 10,588,829, which is a
(Continued)

(51) Int. Cl.
*A61K 6/54* (2020.01)
*A61C 13/14* (2006.01)
(Continued)

(52) U.S. Cl.
CPC ............. *A61K 6/54* (2020.01); *A61C 13/14* (2013.01); *A61C 13/20* (2013.01); *A61C 19/003* (2013.01);
(Continued)

(58) Field of Classification Search
CPC ....... A61C 13/14; A61C 13/20; A61C 19/003; A61C 8/0016; A61C 13/081;
(Continued)

(56) References Cited

U.S. PATENT DOCUMENTS 4,351,853 A * 9/1982 Jochum .................. A61K 6/887
427/2.26
4,977,511 A 12/1990 Gottschalk et al.
(Continued)

FOREIGN PATENT DOCUMENTS

CN 103237521 A 3/2000
CN 105611895 A 5/2016
(Continued)

OTHER PUBLICATIONS

Abate et al. "Effect of photopolymerization variables on composite hardness." The Journal of Prosthetic Dentistry [online], Dec. 2001 [Retrieved on May 7, 2018], vol. 86, No. 6, Retrieved from the Internet: <URL: doi: 10.1067/mpr.2001.120843>, see entire document, especially Abstract; p. 634, col. 1, para 3 to p. 634, col. 2, para 1.
(Continued)

*Primary Examiner* — Nicholas D Lucchesi
(74) *Attorney, Agent, or Firm* — Barnes & Thornburg LLP; Ryan L. Marshall

(57) ABSTRACT

The invention relates to the application of photon energy to energize dental materials to enhance their physical handling characteristics, efficacy, ability to be delivered, reactivity, polymerization, and/or post-cure mechanical properties, among other attributes.

17 Claims, 34 Drawing Sheets

Related U.S. Application Data continuation of application No. PCT/US2018/019260, filed on Feb. 22, 2018.

(60) Provisional application No. 62/462,133, filed on Feb. 22, 2017.

(51) Int. Cl.
| | |
|---|---|
| *A61C 13/20* | (2006.01) |
| *B32B 27/18* | (2006.01) |
| *A61C 13/15* | (2006.01) |
| *A61K 6/52* | (2020.01) |
| *A61K 6/831* | (2020.01) |
| *A61K 6/887* | (2020.01) |
| *C08F 2/50* | (2006.01) |
| *C08F 2/44* | (2006.01) |
| *A61K 41/00* | (2020.01) |
| *A61N 5/06* | (2006.01) |

(52) U.S. Cl.
CPC ............... *A61K 6/52* (2020.01); *A61K 6/831* (2020.01); *A61K 6/887* (2020.01); *B32B 27/18* (2013.01); *A61K 41/00* (2013.01); *A61N 5/062* (2013.01); *C08F 2/44* (2013.01); *C08F 2/50* (2013.01)

(58) Field of Classification Search
CPC ........ A61C 19/004; A61K 6/54; A61K 6/887; A61K 6/52; A61K 6/831; A61K 41/00; A61K 2800/242; A61K 41/0052; A61N 5/062; C08F 2/44; C08F 2/80; C08F 299/028; B32B 17/10706; B32B 17/10935; B32B 37/15; B32B 38/16; B32B 2310/0837; B32B 2315/02; B29C 31/042; B29C 35/0288; B29C 35/0294; B29C 39/10; B29C 66/91921; B29C 2035/0833; B29C 2045/0075

See application file for complete search history.

(56) References Cited

U.S. PATENT DOCUMENTS

| | | | |
|---|---|---|---|
| 5,472,991 A * | 12/1995 | Schmitt | A61K 6/62 |
| | | | 522/4 |
| 5,573,889 A | 11/1996 | Hofmann et al. | |
| 6,168,431 B1 | 1/2001 | Narusawa et al. | |
| 6,204,302 B1 * | 3/2001 | Rawls | C08F 2/50 |
| | | | 522/8 |
| 6,312,254 B1 | 11/2001 | Freidman et al. | |
| 6,444,725 B1 | 9/2002 | Trom et al. | |
| 6,960,340 B2 | 11/2005 | Rowe | |
| 7,014,462 B1 | 3/2006 | Tilse et al. | |
| 7,066,732 B2 * | 6/2006 | Cao | A61C 19/004 |
| | | | 433/29 |
| 9,883,931 B2 | 2/2018 | Gente et al. | |
| 10,076,767 B2 | 9/2018 | Offermann et al. | |
| 2002/0186558 A1 | 12/2002 | Plank et al. | |
| 2003/0036031 A1 | 2/2003 | Lieb et al. | |
| 2006/0121743 A1 | 6/2006 | Brown et al. | |
| 2007/0118144 A1 | 5/2007 | Truckai et al. | |
| 2007/0141524 A1 | 6/2007 | Brennan et al. | |
| 2010/0249793 A1 | 9/2010 | Truckai et al. | |
| 2010/0304322 A1 | 12/2010 | Emde et al. | |
| 2010/0330524 A1 | 12/2010 | Karim et al. | |
| 2012/0213832 A1 | 8/2012 | Ori et al. | |
| 2014/0200511 A1 | 7/2014 | Boyden et al. | |
| 2015/0230900 A1 | 8/2015 | Gente | |

FOREIGN PATENT DOCUMENTS

| | | |
|---|---|---|
| CN | 106233190 A | 12/2016 |
| EP | 2529690 A1 | 12/2012 |
| WO | 2011143454 A1 | 11/2011 |
| WO | 2015164180 A1 | 10/2015 |
| WO | WO2016196027 A1 | 12/2016 |

OTHER PUBLICATIONS

International Search Report dated Jun. 1, 2018, prepared in International Application No. PCT/US2018/0192260.
Written Opinion of the ISA dated Jul. 11, 2018, in International Application No. PCT/US2018/0192260.
Office action dated Mar. 3, 2021 from corresponding Chinese Application No. 2018-80026440.0 (English translation).

* cited by examiner

HEATING OF DENTAL MATERIALS USING OVERTONE SIGNATURES, ABSORBING DYES AND MATERIAL PROPERTIES

This application is a continuation of U.S. application Ser. No. 16/246,205, filed Jan. 11, 2019, which is a continuation of International Application No. PCT/US2018/019260, filed Feb. 22, 2018, the entire contents of which are hereby incorporated herein by reference, which claims priority from U.S. Provisional Application No. 62/462,133, filed Feb. 22, 2017, the entire contents of which are hereby incorporated herein by reference.

BACKGROUND

Technical Field

The invention relates to the application of photon energy to energize dental materials to enhance their physical handling characteristics, efficacy, ability to be delivered, reactivity, polymerization, and/or post-cure mechanical properties, among other attributes.

Background Information

In many dental procedures, such as root canals or tooth restorations, among others, it is necessary to cleanse and fill a space within a tooth in order to effectively restore and seal the space from the exterior environment. During endodontic procedures, practioners use chemomechanical methods to enlarge and cleanse a root canal space. Specifically, practioners use endodontic irrigants to remove debris, remnant pulp tissue and bacteria before filling. Despite advancements in endodontic instruments, endodontic therapy still has an approximate 30% failure rate. These failures have been attributed to bacteria recolonization/infection of the root canal due to improper cleansing or a failed restoration. Restorative procedures often fail for many of the same reasons as endodontic procedures, which are poor adhesion of the material to the tooth structure, and/or microleakage around the restoration which promote bacteria recolonization/infection. Materials used during dental procedures, therefore, must be able to adapt to the complex geometry of the applied space and bond effectively with the tooth or cavity structure to seal off the area in which the material is placed. Improving the effectiveness of dental solutions (e.g. endodontic irrigants) and dental materials (e.g. gutta percha, dental composite resins, i.e. composites, dental sealants, etc) may promote better cleansing and filling of these voids to increase success rates.

Dental Composite

Dental composite resins offer the dental professional one of the most cost-effective methods in which to restore a patient's dentition in an aesthetically pleasing manner, which is defined as matching the patient's natural tooth colors. For cosmetic reasons and to meet consumer demand, composite resins are a preferred alternative material to metallic restorations, most specifically amalgams. Composite resins were first met with doubt and skepticism, which was borne out of a myriad of shortcomings, including the following: poor wear resistance, microleakage, bodily fracture, marginal breakdown, recurrent decay, post-operative sensitivity, inadequate interproximal contacts and contours, color degradation, and inability to polish or maintain polish. In addition to the physical and mechanical limitations of dental composite resins, placement of dental composites is technique sensitive. The placement of composite requires meticulous attention to the procedure or it may fail prematurely. Additionally, the tooth must be kept dry during resin placement or the restoration can fail from poor adhesion to the tooth. Composites are placed while still in a soft, dough-like state, but when exposed to light of a certain blue wavelength they polymerize and harden into the solid filling.

Composite resins generally consist of: acrylate monomers (e.g. triethylene glycol dimethacrylate, TEGDMA, urethane dimethacrylate, UDMA, and bisphenol-A-glycidyldimethacrylate, bis-GMA, etc), inorganic fillers (glasses or ceramics), a photopolymerization system, and pigments and colorants that match tooth colors and shades. Camphorquinone (CQ) is the most common photoinitiator used in photopolymerizable dental material. CQ has a peak excitation at approximately 470 nm and is a type II photoinitiator, which requires the addition of co-initiators to create free radicals to initiate polymerization. Other photopolymerizable dental materials optionally include type I photoinitiators, such as diphenyl(2,4,6-trimethylbenzoyl)phosphine oxide (TPO) or 1-phenyl 1,2-propanedione (PPD), which do not require co-initiators for polymerization. Irrespective of the photoinitiator and/or co-initiator used in commercially available products, it is clinically impractical to completely convert all free monomers to oligomers and polymers within the composite, since the light cannot penetrate more than a couple millimeters into the composite due to absorption and scattering properties of the dental material. If too thick an amount of composite is placed in the tooth, the deeper composite will remain partially soft, and this soft unpolymerized composite could ultimately lead to restoration failure, leaching of potentially toxic free/unreacted monomers, and/or leakage of the bonded joint leading to recurrent dental pathology. To overcome this issue, the dentist is trained to place composite in numerous increments, curing each 2-3 mm section fully before adding the next increment to maximize polymerization through each composite increment and the complete restoration. In addition, the clinician must carefully construct the composite filling to match the patient's natural occlusion. If the filling is too high, the patient's bite may be unnatural, which could lead to chewing sensitivity and/or restoration failure. Due to the aforementioned issues, improved composite compositions, curing lights, delivery systems, and methods for placement and enhanced post-cure properties for dental composites is desirable to aid the clinician and improve the success of the restoration.

A major downside to conventional dental composites (that is documented in the literature) is the fact that resins demonstrate polymerization shrinkage. The polymerization of the resin begins the conversion of the monomer molecules into a polymer matrix, which leads to contraction. This bulk contraction (polymerization shrinkage), is seen as a volumetric decrease during the curing/polymerization process. The material transforms in phases; from a viscous, to viscous-elastic, to elastic in nature. In the viscous stage, stress is non-existent. During the viscous-elastic stage, however, stresses occur in the material and at the material-tooth interface. Shrinkage stresses are transferred to the cavity walls of the tooth due to volumetric changes in the composite. These stresses, and the resulting polymerization shrinkage, can be influenced by material selection, filler content, irradiance and duration of the applied polymerization light source, curing characteristics of the resin, water sorption, and cavity prep configuration. Many options have been proposed to limit internal tooth stresses, including the following: the use of liners and bases, alteration of polymerization light, irradiance waveform, incremental layering, increased filler content, and modification of bonding techniques. Unfortunately, none of these can fully compensate for the effects of this phenomenon.

The effect of lowering viscosity to improve adaptation of the composite and to improve ease of placement has been shown to be important. This is the primary basis for the development of flowable resin composites and flowable liners. These flowable composites achieve their lower viscosity primarily by a reduction in reinforcing filler content and changes in the matrix chemistry. A variety of studies have shown that lower viscosity composites can improve adaptation and reduce microleakage. The use of flowable composites has also been touted as a way to ensure a more intimate contact with both the dentin bonding agent and internal surfaces of the prep, and to augment the seal obtained by a composite at the cavosurface margin. With some types of restorations, it can be difficult to achieve complete interfacial sealing between the tooth structures and composites.

One potential way to improve sealing would be to use lower viscosity flowable composites; however, these flowable composites are not generally considered as durable as higher viscosity materials, due to the lower levels of reinforcing filler particles present. A second approach is to use a flowable liner in conjunction with regular composites. A third alternative is to use conventional/highly filled composites that have been heated to lower their viscosity. In this last approach, higher durability conventional composites could be used, while utilizing their reduced viscosity to form more intact interfaces with tooth tissues and eliminates the need for a flowable liner. Also, this third alternative is seen as advantageous since flowable resins are less filled than traditional composites, and therefore exhibit higher shrinkage rates due to the decreased filler content. This could be problematic in restorative techniques when a large volume of flowable composite is used in an attempt to improve the seal and marginal adaptation of the composite.

As stated earlier, many polymer resins exhibit lower viscosity when they are heated. The theoretical basis for this behavior is that thermal vibrations force the composite monomers or oligomers further apart, allowing them to slide by each other more readily. Studies have shown that heating general polymers and resin composites lowers viscosity and thereby improves adaptation. Deb et al. (Dent Mater. 2011 April; 27 (4): e51-9) have shown that increasing dental composite temperature lowers viscosity as indicated by decreased film thickness. Similar results were found by Broome (Dent Adv. 2006 January; 4). As such, preheating composites has been the focus of research in recent years, as preheating improves the physical and mechanical properties of the resin. Preheating of dental composites has been shown to reduce the viscosity and potentially increase the post-cure microhardness of the composite resin. Currently available devices used to aid the clinician in pre-heating composite rely primarily on conductive heat transfer and have many downsides, including long heat up times, not heating at the point of delivery which causes the composite to cool and potentially reach room temperatures depending on procedural application times, the lack of being able to heat multiple composites quickly, and the lack of being able to heat the composite once placed within the restoration; among other challenges and limitations.

Effect of Elevated Temperatures on Composite Properties after Curing

There is concern about the effect preheating has on the properties of photopolymerizable dental materials. A few studies have investigated the conversion of double bonds (a measure of how completely the polymerization reaction progresses) and hardness of the composite after the preheating treatment. These studies are important in determining how quickly and completely the composite polymerizes. Preheating appears to either improve conversion and hardness or it produces no negative changes. Increased conversion generally equates to better mechanical properties of the polymeric materials and composites. Therefore, preheating may lead to more durable composite restorations. Furthermore, there has been concern that the higher temperature of preheated composite would lead to greater shrinkage of the composite during and after curing. Elhejazi (J Contemp Dent Pract. 2006 Jul. 1; 7(3):12-21) showed that raising the temperatures of resin composite led to greater shrinkage. In response to this concern, it was suggested that the preheated composite be allowed to cool for a period of about 15 seconds after placement but before curing. Another concern expressed in the literature was that subjecting the composite to preheating cycles would reduce the shelf life of the unused composite. However, Daronch et al. (J Esthet Restor Dent. 2006; 18(6):340-51) showed that neither preheating cycles nor extended preheating for 24 hours caused any significant changes in monomer conversion. Although some studies exist that demonstrate preheating does not negatively impact dental materials, research is conflicting and not comprehensive for all dental materials.

Obturation

Successful root canal therapy is dependent on many factors. It begins by removal of all the organic substrate from the canal. This includes removal of the coronal pulp tissue and radicular pulp tissue. The coronal pulp tissue is removed by performing complete access and identifying straight-line access to the radicular pulp tissue. This, in turn, allows the practitioner to remove the radicular pulp tissue with endodontic files and irrigation. Irrigation is arguably the most important part of endodontic therapy as chemomechanical instrumentation alone leaves approximately 30% of the root canal untouched. Therefore, the importance of effective irrigation in root canal preparation cannot be overemphasized, and enhancing the activity/efficacy of endodontic irrigants is desired.

Finally, the last objective is preventing reinfection by obtaining a three-dimensional obturation of the canal. For increased endodontic treatment success, the canal system must be effectively sealed coronally and apically. The apical seal is the principal barrier to leakage. There are many different obturation techniques; no one technique has been identified as clearly superior. It has been shown that adding heat to obturation increases success rates and allows for obturation of canal irregularities and anatomy that traditional techniques may not seal. Characteristics of successful obturation are defined and categorized as the three-dimensional filling of the entire root canal system as close to the cemento-dentinal junction as possible; i.e., without gross overextension or underfilling in the presence of a patent canal. Minimal amounts of root canal sealers are used in conjunction with the core filling material to establish an adequate seal.

Controversy has surrounded root canal obturation for many years. Clinicians and academics alike have researched, studied, applied, and compared many warm obturation techniques, and no single technique has been proven superior to another, leaving clinicians to experiment and form preferences through trial.

Following endodontic obturation, a coronal restoration is completed to restore the tooth shape and occlusal surface. There is reasonable evidence to suggest that coronal leakage through improperly placed restorations is a significant contributing factor in endodontic therapy failure. Thus, there remains an unmet need for new methods, compositions, and device that improves upon dental material application and the curing of dental materials and for performing the aforementioned dental procedures.

BRIEF SUMMARY

A benefit of the embodiments of the invention described herein is that via the application of photon energy to the dental composite or dental composite's container, the material is rapidly and efficiently heated chairside above ambient temperature. This inventive concept also applies to all dental materials. In comparison to commercially available composite warmers, the disclosed invention is highly efficient, especially when there is high conversion efficiency from photon energy to heat. Elevating the dental material's temperature, for example dental composite resins, improves the material's physical handling characteristics and ability to be delivered, obviating the need of flowable composites as the dental composite is capable of exhibiting viscosities similar to flowable composites but does not suffer from the negatives of flowable composites (high shrinkage, low wear retention, low hardness, etc.). Furthermore, since the invention allows for the application of photon energy to the dental materials once it is placed, improved handling characteristics can be achieved even after dispensing the material from the tool or wand. Additionally, improved flowability and adaptation can allow for a filling smaller voids in the tooth and performing minimally invasive restorations. Furthermore, heating composite would allow manufacturers to develop and commercialize more highly filled composite, which heretofore has not been possible due to extrusion and manipulation constraints of highly filled materials. Normally, increasing the filler content would make the composite too thick and hard to work with, however by heating using photon energy, the flowability will return to that of less filled or even flowable composites while still maintaining the benefits of a highly filled composite (i.e. reduced shrinkage stress, increased durability). Thus, the disclosed invention further improves coronal restorations and thereby improves clinical outcomes.

As described herein, a dental material is provided that can be heated to increase the flowability of the material to ease the application and conformance of the material to the tooth surface to which the material is applied. Further, as a result of the heating of the material, when cured the composite has increases in hardness and durability, without any deterioration in the cured dental materials compared to dental materials placed without the use of the methods described herein.

In addition, the disclosed invention utilizes photon energy to quickly heat endodontic irrigants above ambient temperature and to promote photochemical effects thereby making the irrigants more efficacious during use. Furthermore, a major benefit of the disclosed invention is that the use of photon energy does not have any deleterious impact on dental materials or dental composite resins specifically. Moreover, the invention described herein allows for gutta percha, or a similar obturation material, to be delivered and applied within the root canal space with improved handling and lower viscosities than previously achieved. By lowering the viscosity and improving the delivery, the invention allows the clinician to more reliably gain a three dimension fill of the complex root canal anatomy and significantly reduce endodontic treatment failures.

Statistically significantly greater absorbance was observed with concentrations ≥1 ppm of the ICG dye. The figure demonstrates that adding a photon energy absorbing dye to the composite significantly increases the absorption characteristics of the dental material. This increased absorbance can be targeted using photon energy to increase heating rates of materials.

Figure 25:
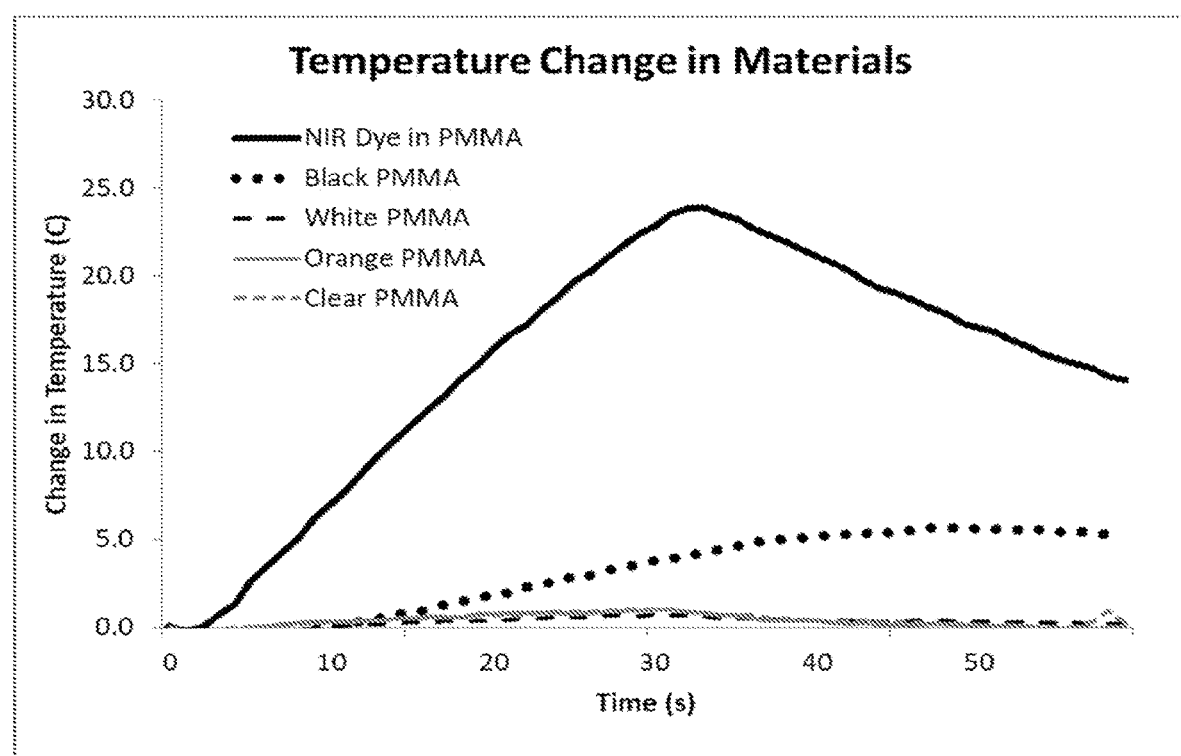

FIG. 25 is a graph showing the heating profiles obtained from polymethylmathacrylate (PMMA) resin, with or without differing absorbing dyes incorporated therein, subjected to a constant photon energy source at 940 nm for about 30 seconds. Temperature measurements were recorded for about 60 seconds total. The graph demonstrates that by incorporating dyes that have higher absorbance values commensurate with the applied photon energy source, the heating rates and overall gain in temperature can be substantially increased compared to resin with no dye or less absorbing dyes/pigments. Additionally, once photon energy is stopped, the material temperature decreases readily, as evident by the quickly decreasing temperature measurements for the NIR dye in PMMA between 30 seconds and 60 seconds. This is an additional advantage of the invention as materials can cool quicker when photon energy is stopped. Thus, if a hot material is warmed in a disclosed inventive device, the device can be turned off and the material will cool quickly before touching. Conversely, commercially available warming units maintain their heat for significantly longer periods of time, as they typically heat metal blocks which then primarily transfer heat to the material via conduction.

Figure 26:
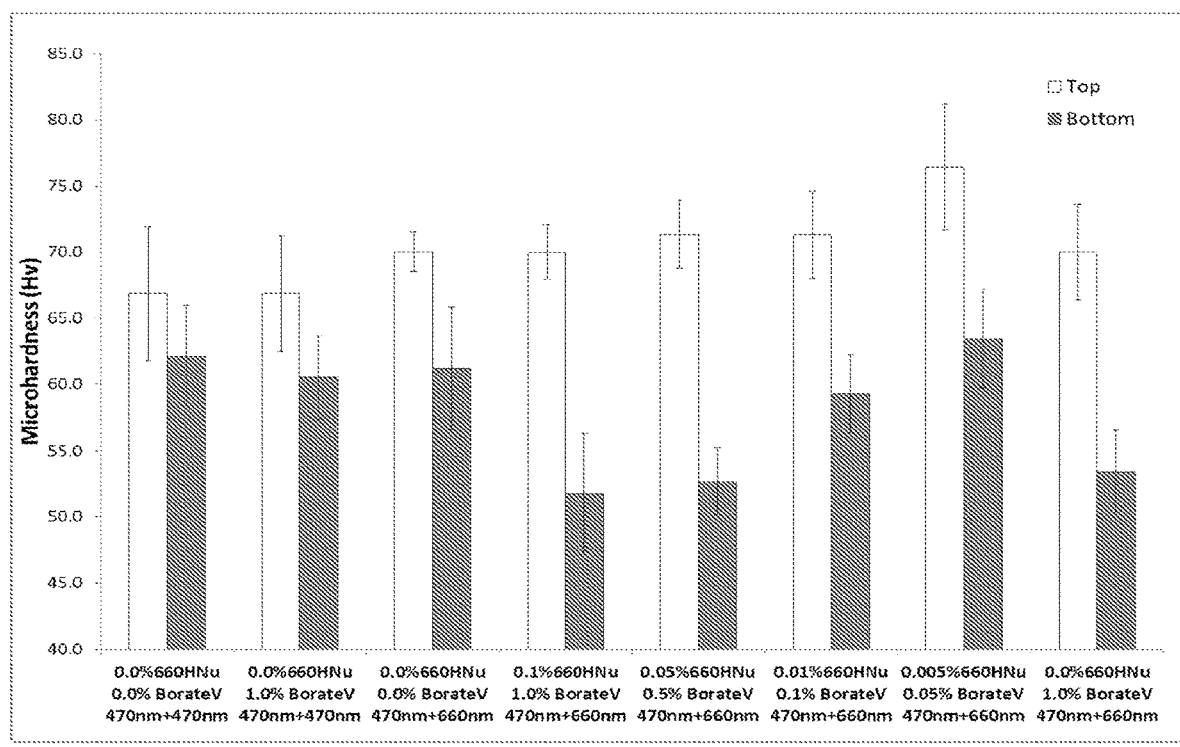
Figure 27:
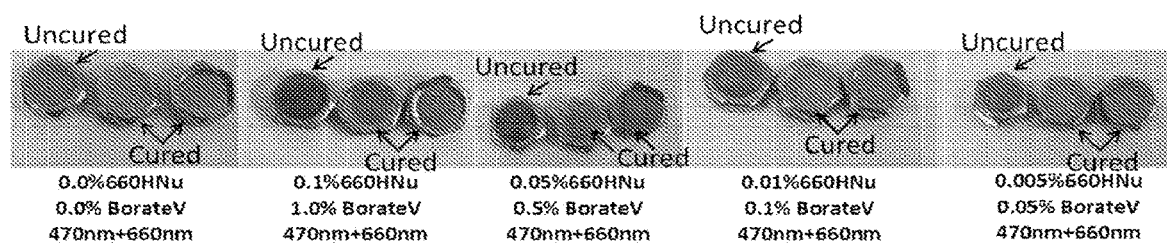

FIG. 26 is a graph showing the post-cure microhardness values of a commercially available composite (Ivoclar Evo-Ceram A2 shade) with or without an additional photoinitiator (660HNu) and co-initiator (BorateV) at various concentrations when subjected to curing emissions of equivalent total optical power. An improvement in microhardness values was seen for Ivoclar Evo-Ceram additionally incorporating 0.005% 660HNu and 0.05% BorateV subjected to simultaneous 470 nm and 660 nm. This figure demonstrates that improving polymerization and microhardness values is dependent on the concentration of the additionally incorporated photoinitiator and coinitiator. Additionally, a visible color change from green/blue to standard A2 shade was visualized after photopolymerization for the various compositions, as shown in FIG. 27. In particular, the green/blue color was unnoticeable post-cure for 660HNu concentrations equal to or below 0.05%. Thus, these concentrations can be used to provide a visible indication of a complete/successful cure to the clinician. Conversely, remnant green/blue color is observed in the 0.1% 660HNu samples post-cure and thus would not be suggested for aesthetic dental use.

FIG. 27 demonstrates that any introduced color by incorporated additives can be lost upon curing to indicate a successful/complete cure to the clinician.

Figure 28:
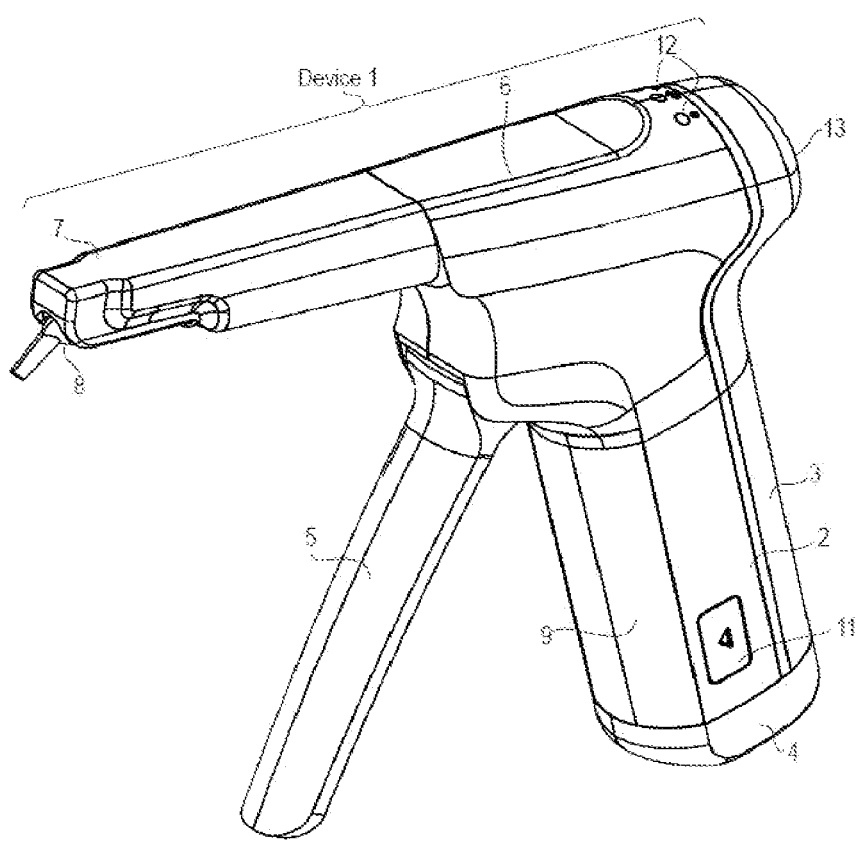

FIG. 28 is an isometric view of a delivery device according to another exemplary embodiment of the invention.

Figure 29:
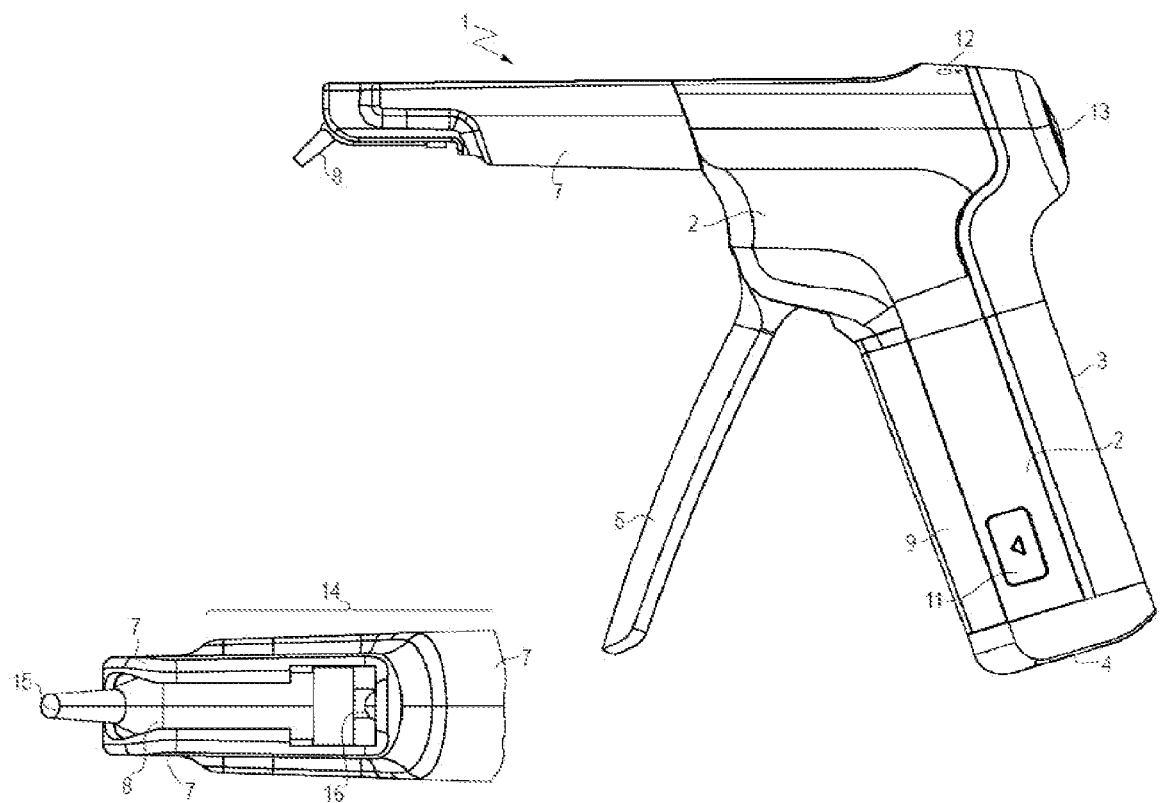

FIG. 29 is an isometric view of a delivery device according to another exemplary embodiment of the invention. The inset image shows the compule/material container located with the device's receptacle for receiving the compule/material container.

Figure 30:
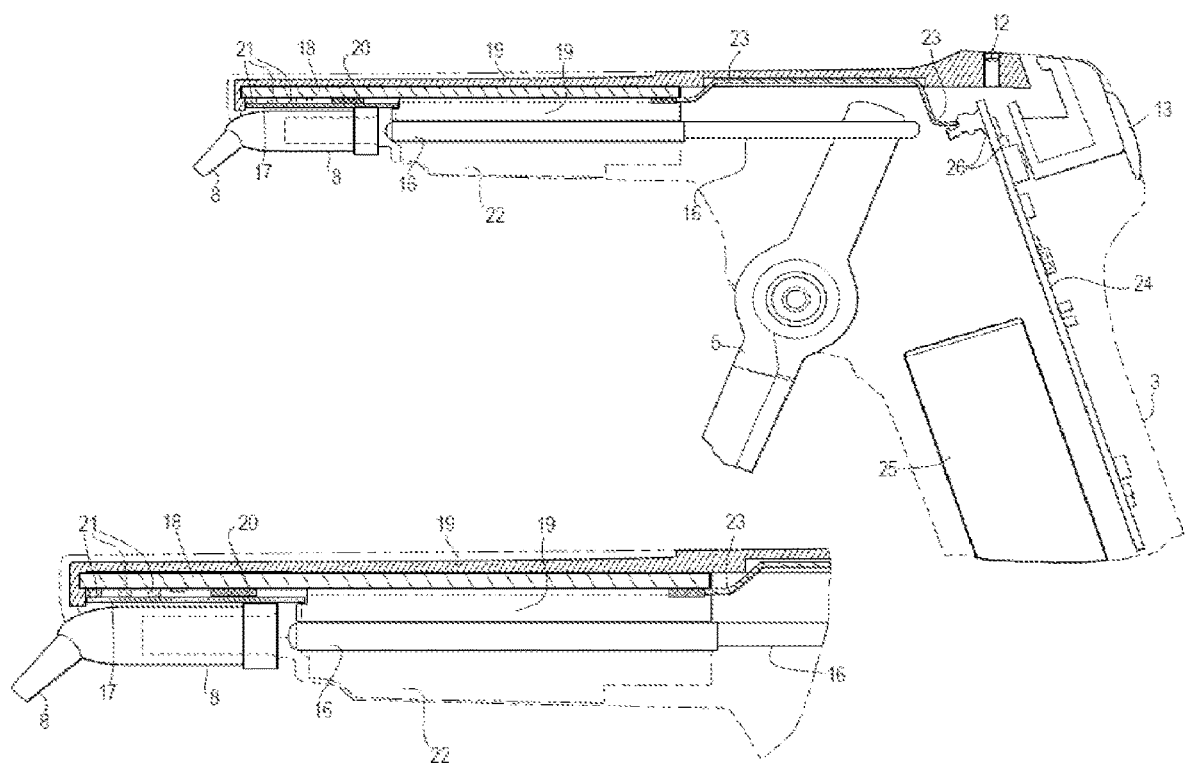

FIG. 30 is a cross-sectional view of part of the device. The inset images shows the compule/material container located with the device's receptacle for receiving the compule/material container, as well as how the device's plunger makes contact with the dental material container to extrude the dental material therein.

Figure 31:
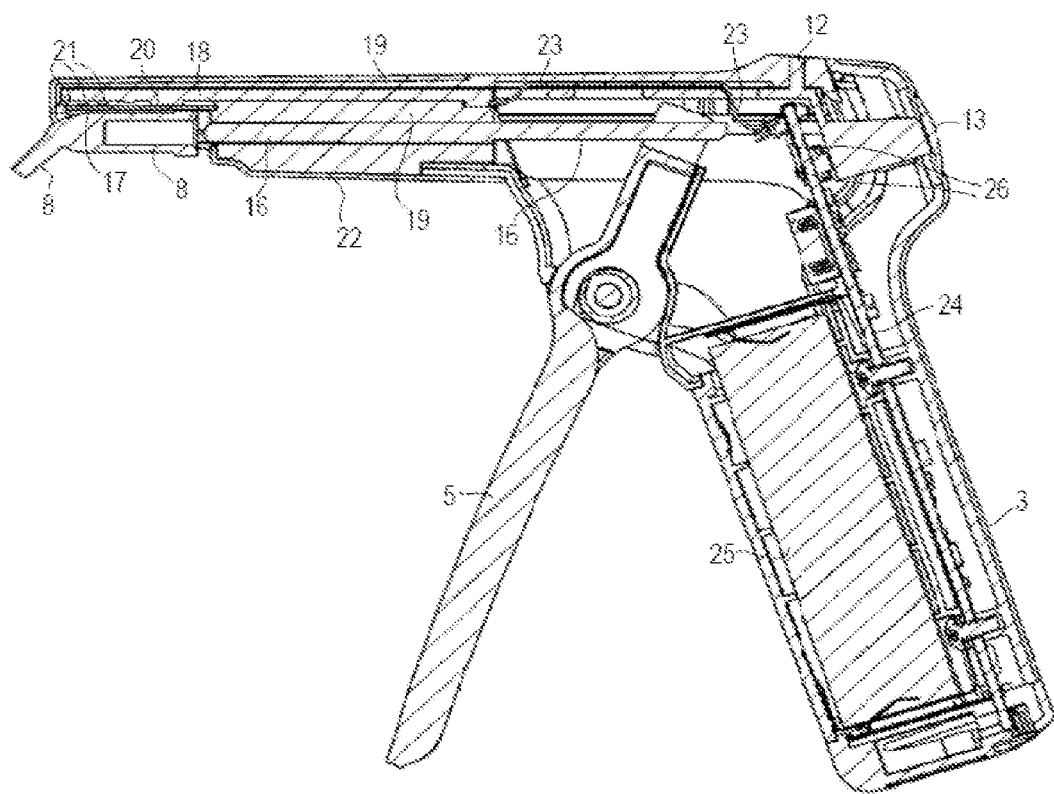

FIG. 31 is a cross-sectional view of the isometric side-profile image within FIG. 25.

Figure 24:
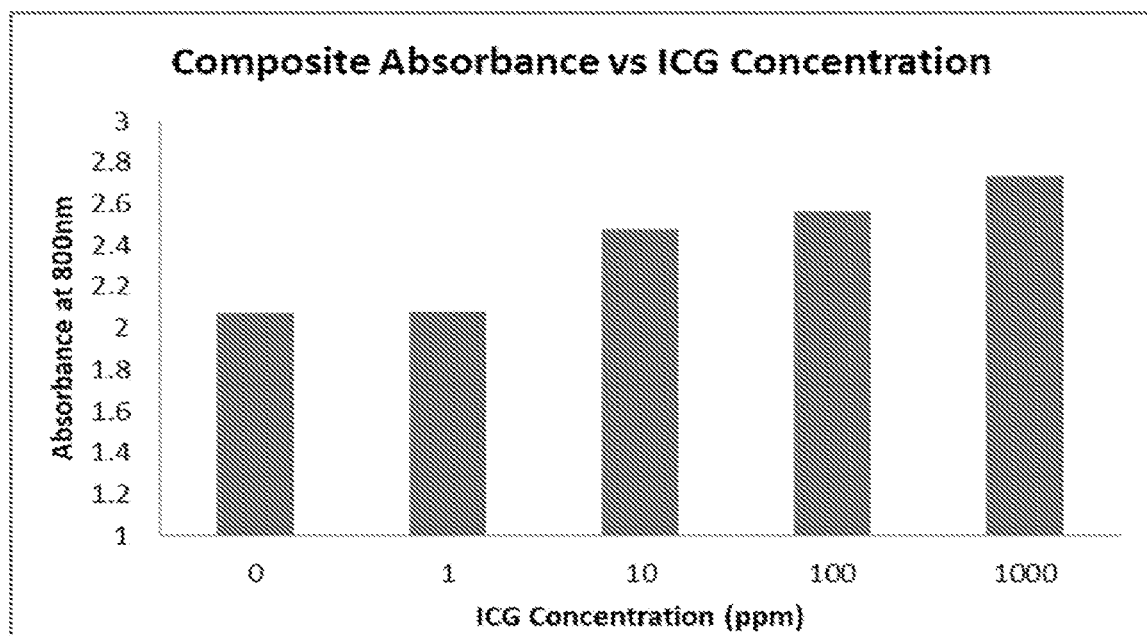
FIG. 24 is a graph showing the increase in dental composite (Filtek Supreme) absorbance when a photon energy absorber/dye (ICG) was added at varying concentrations.
Figure 32:
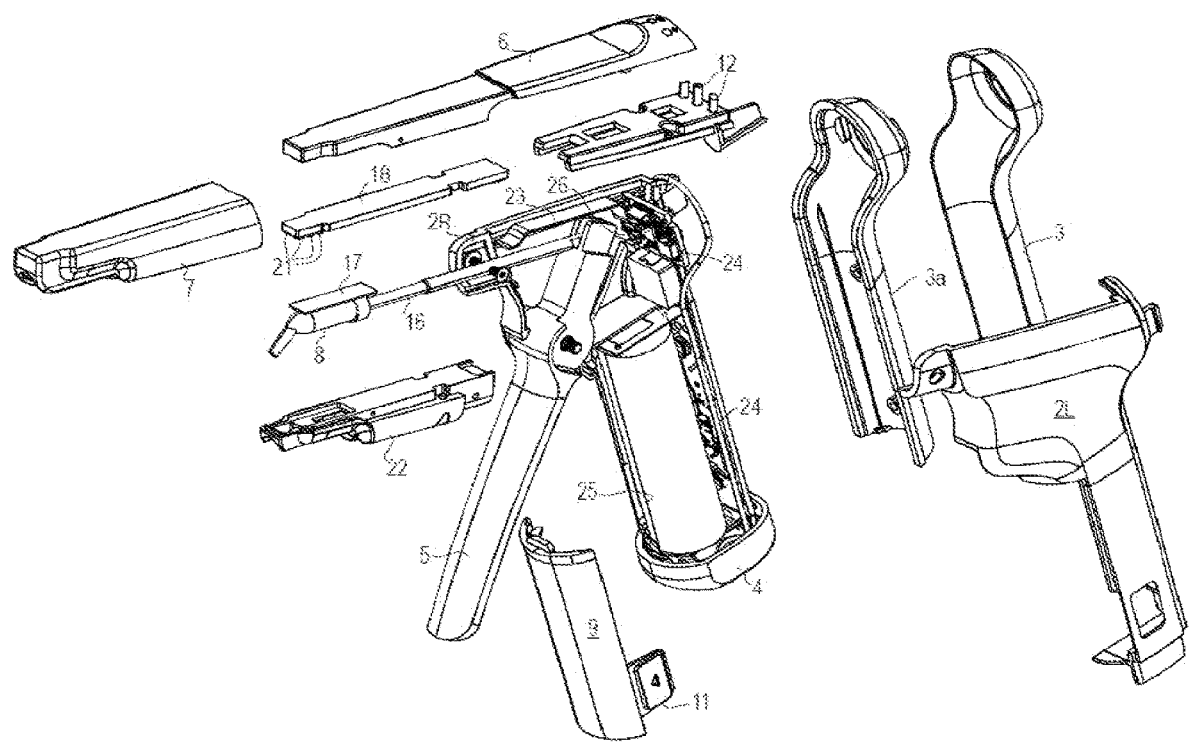

FIG. 32 is an exploded view of the device shown in FIG. 24 showing the various components of the device.

Figure 33:
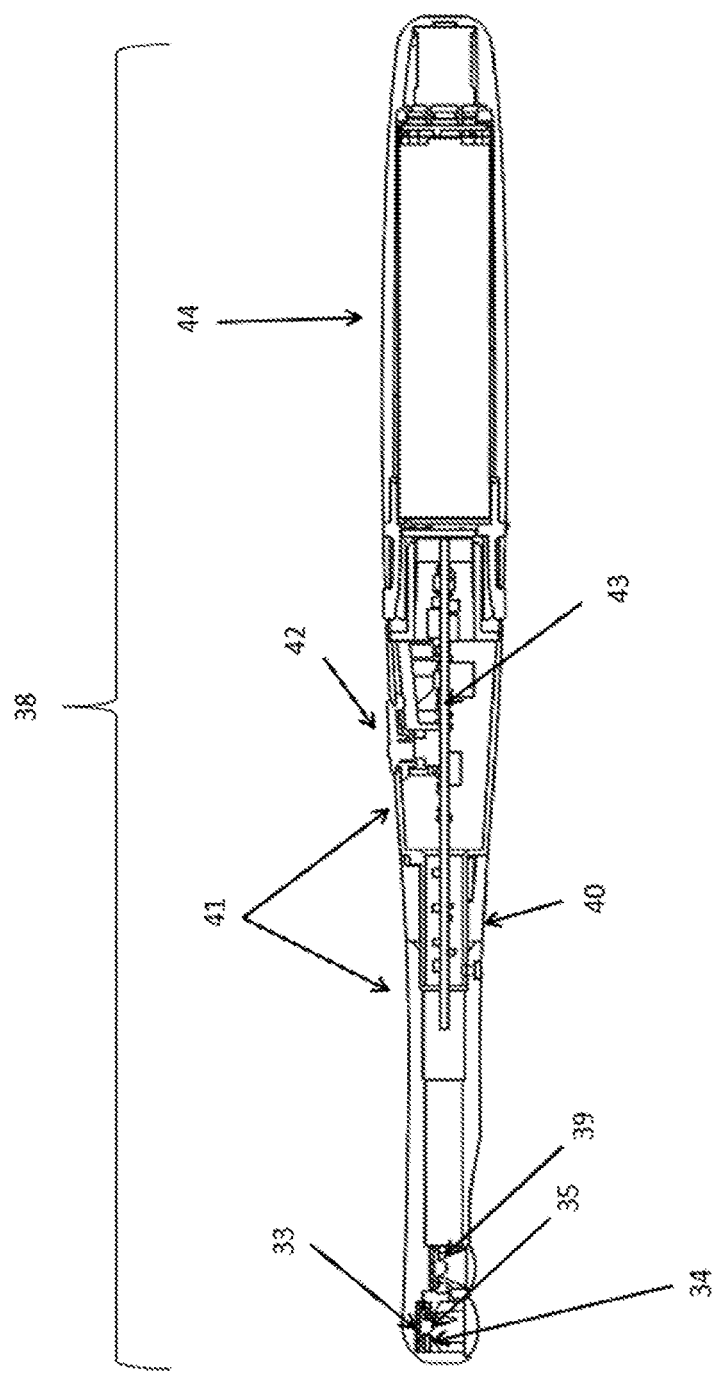

FIG. 33 is an isometric cross-sectional view of a multi-spectral curing light device according to one exemplary embodiment of the invention.

Figure 34:
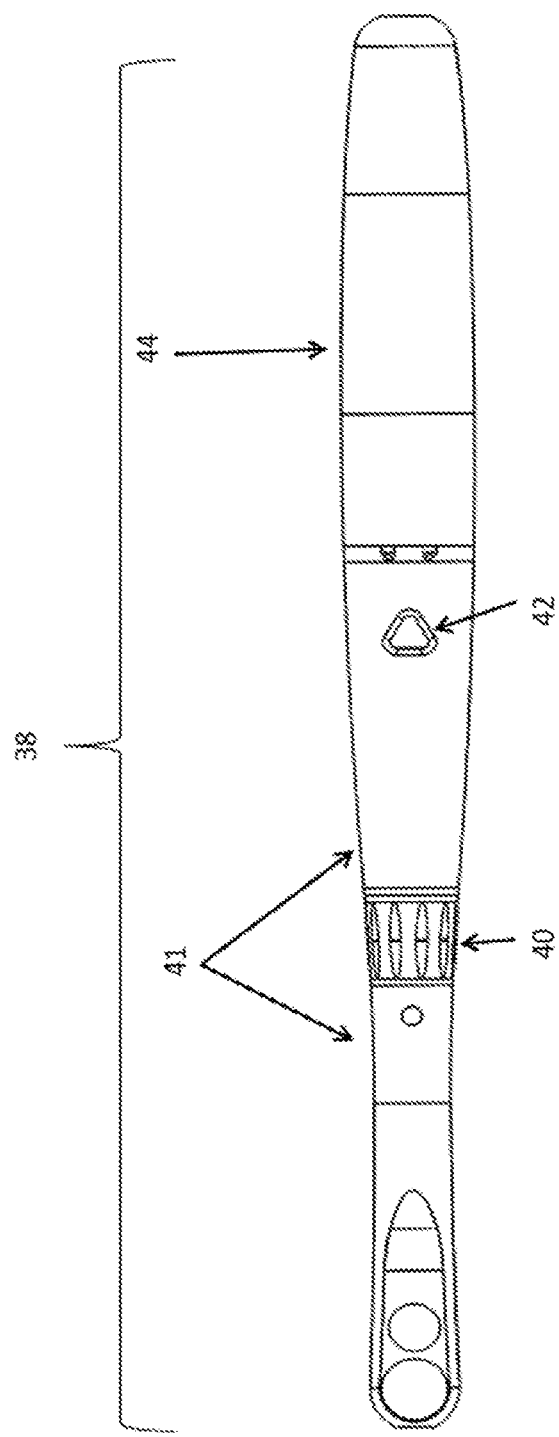

FIG. 34 is a bottom view of a multispectral curing light device according to one exemplary embodiment of the invention.

Figure 35:
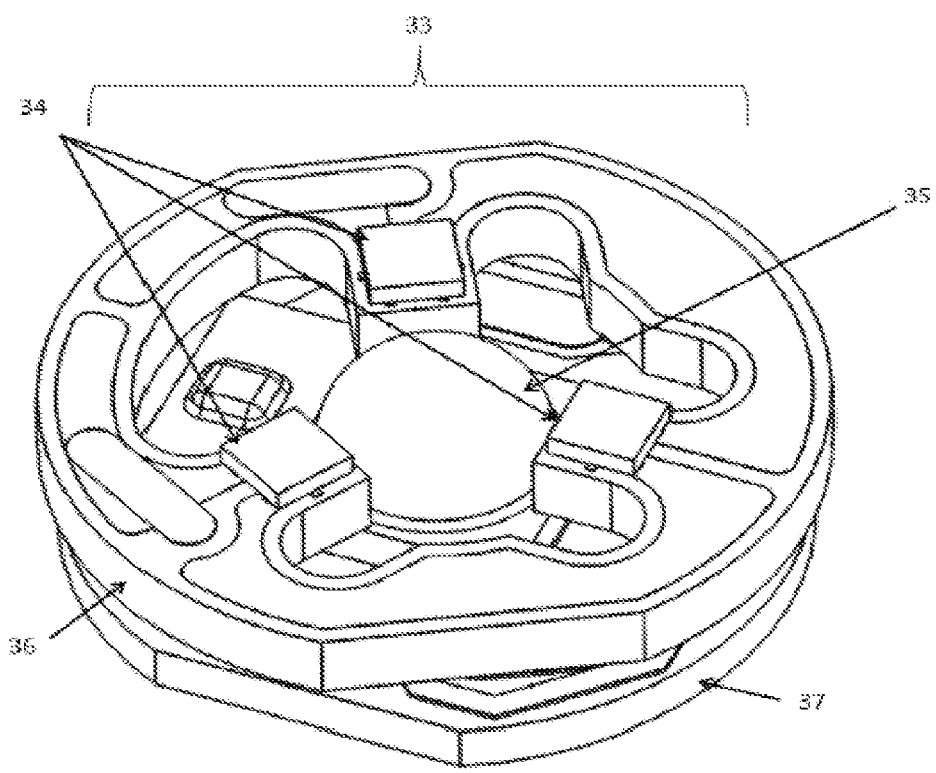

FIG. 35 is an exemplary embodiment of a package consisting of at least three photon emitters (i.e. LEDs) for use in a multispectral device which emits at least two discrete emission spectra for curing dental composite materials and for the application of photon energy for heating.

Figure 36:
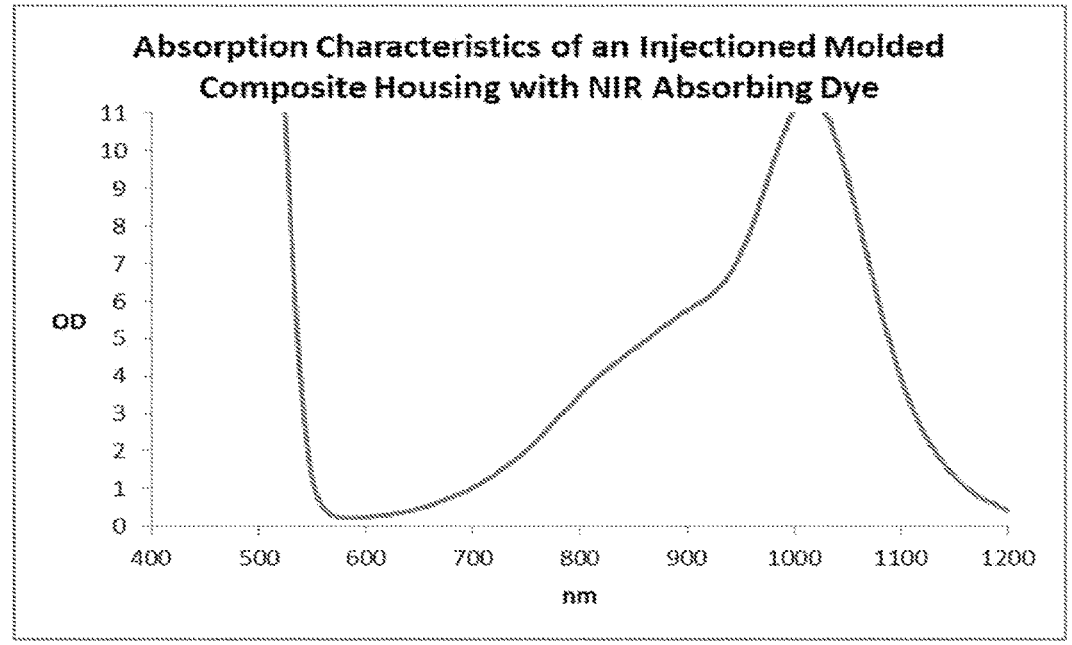

FIG. 36 is a graph showing the absorbance versus wavelength characteristics of one exemplary embodiment of the invention for a dental material container, wherein a thermoplastic resin (polycarbonate) incorporates a photon energy absorption dye (Epolite 7657) that has high absorbance from about 800 nm to about 1100 nm and below 550 nm (sample is 2 mm thick). This dye/additive simultaneously results in high absorbance within the photon energy range, and thus can be targeted for increased container and/or material heating rate using photon energy emitters, as well as within the blue light range (400-500 nm), to successfully block polymerization light from photopolymerizing the dental material within the container.

Figure 37:
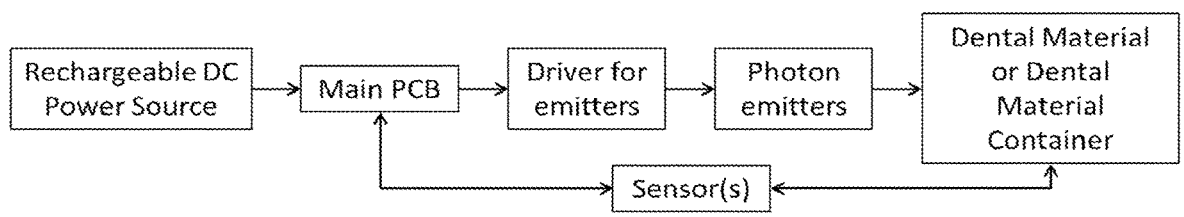

FIG. 37 is a block diagram showing the generalized functioning components of one exemplary device used to heat, control and identify the dental material and/or dental material container. The dental material and/or dental material container's temperature can be controlled and maintained via the use of a sensor feedback loop. Additionally, the sensor may be used to ensure that photon energy sources only emit photon energy if a material or container is present. Lastly, the sensor may be used to specifically identify various materials and/or containers based on the feedback.

DETAILED DESCRIPTION

The following paragraphs define in more detail the embodiments of the invention described herein. The following embodiments are not meant to limit the invention or narrow the scope thereof, as it will be readily apparent to one of ordinary skill in the art that suitable modifications and adaptations may be made without departing from the scope of the invention, embodiments, or specific aspects described herein. All patents and publications cited herein are incorporated by reference herein in their entirety.

For purposes of interpreting this specification, the following terms and definitions will apply and whenever appropriate, terms used in the singular will also include the plural and vice versa. In the event that any definition set forth below conflicts with any document incorporated herein by reference, the definition set forth below shall control.

The term "room temperature" or ambient temperature as used herein refers to common ambient temperatures ranging from about 20° C. to about 27° C.

The term "treating" refers to administering a therapy in an amount, manner, or mode effective to improve a condition, symptom, or parameter associated with a disorder. In some aspects, treating refers to the treatment of a dental ailment such as a cavity.

The term "prophylaxis" refers to preventing or reducing the progression of a disorder, either to a statistically significant degree or to a degree detectable to one skilled in the art.

The term "substantially" as used herein means to a great or significant extent, but not completely.

As used herein, "a" or "an" means one or more unless otherwise specified.

Terms such as "include," "including," "contain," "containing," "has," or "having," and the like, mean "comprising."

The term "patient" or "subject" refers to mammals and humans. Thus, in one aspect, the subject is a mammal, or a mammal in need thereof. In one aspect, the subject is a human, or human in need thereof. In one aspect, the human or human in need thereof is a medical patient. The subject can be from ~0 years of age to 99 years of age or older.

Described herein are methods for applying photon energy to heat dental materials and dental material housings or containers. Also described herein are dental material compositions and dental material containers or housings having enhanced heating properties and photopolymerization properties based upon the inclusion of heating additives and photopolymerization enhancer systems. Further described herein are devices capable of applying specific wavelengths of photon energy for heating, delivering, and curing a dental composition (e.g., the dental compositions disclosed herein). Also described herein are methods for treating patients with the methods and devices disclosed herein. Although one example or embodiment may discuss, or specifically relate to, a certain application or aspect of the invention, it is understood that the example or embodiment may additionally relate to and envision other detailed aspects of the invention. For example, certain devices or methods may be discussed with relation to dental composite materials, however, the same devices or methods may be applicable to other dental materials in general.

The inventors report that photon energy between 0.49 eV-2.38 eV (i.e. 2500 nm-520 nm), between 0.49 eV-1.90 eV (i.e. 2500 nm-650 nm) or between 1.23 eV-2.06 eV (i.e. 1000 nm-600 nm) can be used to enhance dental materials' handling properties, mechanical properties, and performance properties with high conversion efficiency. Dental materials include but are not limited to: composites, resins, glass ionomer resins, cements, cavity liners, endodontic irrigants, endodontic obturation materials, gutta percha, anesthetic, and sealants. Accordingly, the invention described herein includes a method for heating dental materials, a method for improving the polymerization of photopolymerizable dental materials, dental material heating and delivery devices, dental material heating and curing devices, and dental material compositions.

Photon energy outside the specified range of 0.49 eV-2.38 eV (i.e. 2500 nm-520 nm) is still envisioned by the invention to enhance dental materials' handling properties, mechanical properties, and performance properties with high conversion efficiency. In particular, the use of ultraviolet light may be utilized as ultraviolet wavelengths have high photon energy (specifically ultraviolet A wavelengths: 315 nm-400 nm, 3.93 eV-3.09 eV), and many materials exhibit inherently high absorbance below 400 nm. Although these other wavelengths are possible, some particular embodiments described further herein utilize photon energy within the specified range of 0.49 eV-2.38 eV (i.e. 2500 nm-520 nm) as wavelengths below 400 nm can have a deleterious impact on the dental material, specifically photopolymerizable dental materials, and are a potential safety concern due to ionization. A specific concern is the photopolymerizing of dental materials, which may occur if ultraviolet light is utilized directly on the material itself, however, in some embodiments, ultraviolet light can be utilized to heat the dental material's container, providing that the dental material's container has an optical density value of at least two for wavelengths below 400 nm, i.e. the dental material's container transmits <1% of light below 400 nm. Conversely, in some other embodiments, ultraviolet light may be used on other non-photopolymerizable dental materials, specifically endodontic irrigants, to enhance their performance properties via photochemical effects.

Method for Applying Photon Energy to Heat Dental Materials

Some embodiments described herein are methods for heating dental materials above ambient temperature using a photon energy without deleteriously affecting the dental material. One embodiment is a method of heating a dental material with photon energy between 0.49 eV-2.38 eV (i.e. 2500 nm-520 nm) to quickly heat the dental material to an elevated temperature above ambient temperature. In some aspects, the dental material is heated to a temperature of about 50° C. to about 250° C. In some aspects, dental material is heated to a temperature between about 50° C. and about 100° C. In some other aspects, the dental material is heated to a temperature between 60° C. and about 80° C. In some aspects, the applied photon energy is between 1.23 eV-2.06 eV (1000 nm-600 nm). In some embodiments, photon energy to heat the dental material is applied prior to application of the dental material. Other photon energy wavelengths may be utilized by tuning the applied photon energy to the fundamental absorption frequency/wavelength and/or an overtone vibrational band of the dental material or the dental material's container. In particular, any resonant frequency above the fundamental frequency is referred to as an overtone. In the electromagnetic spectrum, overtone bands are multiples of the fundamental absorption frequency. Because energy is proportional to the frequency absorbed, which in turn is proportional to the wavenumber, the first overtone that appears in the spectrum will be approximately twice the wavenumber of the fundamental. That is, the first overtone v=1→2 is approximately twice the energy of the fundamental, v=0→1. For example, a vibrating diatomic molecule such as hydrochloric acid (HCl), with a fundamental absorption at 3465 nm, will have its first overtone absorption band at 1733 nm (actually observed at 1764 nm), second overtone absorption band at 1155 nm (actually observed at 1198 nm), third overtone absorption band at 866 nm (actually observed at 915 nm), and fourth overtone absorption band at 693 nm (actually observed at 746 nm). Thus, to obtain equivalent vibrational motion, significantly more energy will be required at the first overtone compared to the energy needed at the fundamental absorption frequency/wavelength. As increased molecular vibrations results in heat generation, it is possible to target the fundamental absorptions and/or overtone bands to heat objects and materials.

With regard to dental materials, the fundamental absorption bands are typically outside the specified photon energy range (0.49 eV-2.38 eV, i.e. 2500 nm-520 nm). Therefore, overtone bands of the dental materials are targeted by some embodiments described herein. Specifically for photopolymerizable dental materials (i.e. composites, resins, cements, sealants, etc), the application of photon energy prior to use or during use (i.e. in vivo) quickly heats the material above ambient temperature but does not prematurely cure or negatively impact the photopolymerizable material pre or post cure, which can occur if the applied photon energy activated the material's incorporated photoinitiator.

Clinically, heated photopolymerizable materials are advantageous as they exhibit increased flowability to ease the application and conformance of the photopolymerizable material to the tooth surface. This same concept holds true for all dental materials in general. Additionally, the photopolymerizable material's mechanical properties may be enhanced by applying photon energy during curing, or just before curing, to increase the temperature, which has been shown to increase post-cure properties (degree-of-conversion and microhardness), compared to standard curing. Thus, in some aspects described herein the applied photon energy is at a separate wavelength from the absorption peak used to active the photopolymerizable material's photoinitiator.

Figure 1:
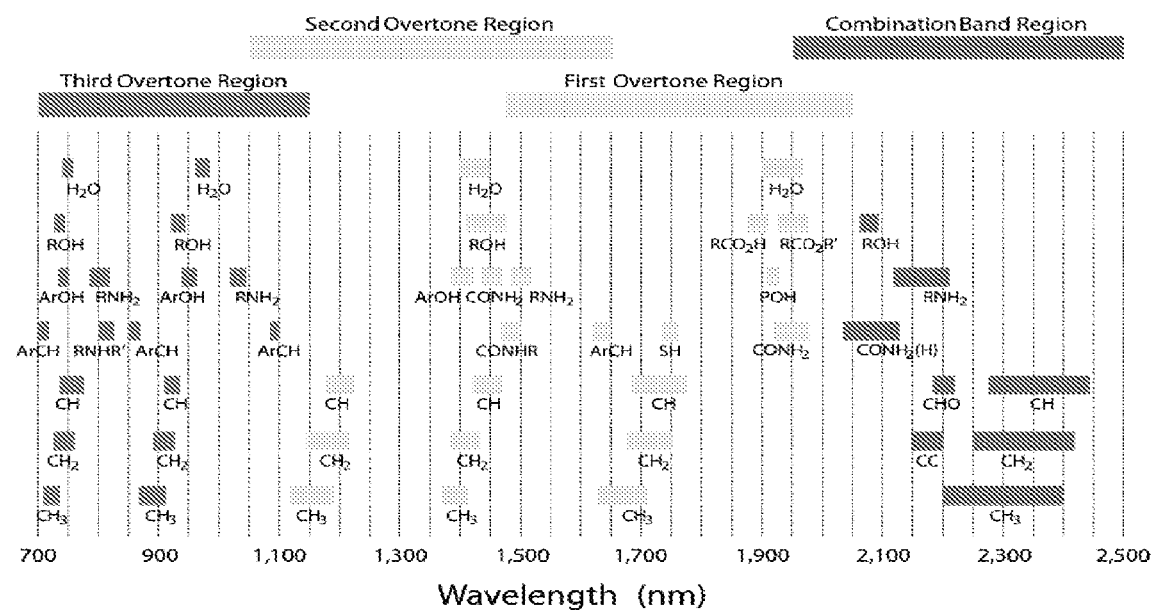
FIG. 1 is a graph of near infrared absorption bands of common organic bonds and functional groups. The figure details the peak absorbance bands and respective first, second and third overtone absorbance bands of the organic and functional group structures.

The type and amount of photon energy to be applied to the dental material for a desired heating can be determined based upon the absorbance overtone regions for various components (e.g., molecules and bonds). For example, various components and their respective overtone regions is illustrated in FIG. 1. Most components have absorbance in more than one overtone region, and thus some embodiments relate to the application of photon energy to these composites utilizing wavelengths in the combination band region, primary absorption band, or any of the overtone regions contained within 0.49 eV-2.38 eV (i.e., 2500 nm-520 nm). In some embodiments, the utilized photon energy is between 1.23 eV-2.06 eV (i.e., 1000 nm-650 nm).

In some embodiments, the applied photon energy is in the third overtone region, or greater overtone, or other component absorption characteristics within the specified photon energy ranges/wavelengths, to provide certain advantages with regard to the degree and speed of heating that can be accomplished without overly high energy requirements. The disclosed embodiments are highly efficient at converting energy from a power source to heat using photon energy that is tuned to the dental material and/or dental materials container.

Photon emission within the third overtone band can be accomplished with currently existing LED technology whereas emission of photons in the $1^{st}$ or $2^{nd}$ overtone band would require diode lasers and much higher expense with much lower optical energy output. Fundamentally, shorter wavelengths of light have greater frequencies and higher photon energy. Given the relationship between wavelength and frequency—the higher the frequency, the shorter the wavelength—it follows that short wavelengths are more energetic than long wavelengths. As such, the third overtone, despite having a lower absorbance in certain instances, utilizes wavelengths that have high energy and are can demonstrate more effective and efficient heating properties. In addition, with information regarding the components utilized in a composite material, the particular wavelengths in the selected region can be specifically targeted onto the composite to efficiently affect the heating of the composite material in the wavelengths where the molecules and bonds have the highest absorption.

In some embodiments, photon energy is applied to dental materials including but not limited to: anesthetic (reducing pain during injection), gutta-percha (for endodontic root canal obturation), dental composites, sealants, cements, cavity liners, and glass ionomer resins (e.g., lowering viscosity, improving handling characteristics, decreasing voids, and improving mechanical properties post-cure) and endodontic irrigants (increasing efficacy and reactivity).

Thus, some embodiments the photon energy herein is applied utilizing devices that are specifically configured for the efficient heating of a dental material sample.

Method for Applying Photon Energy to Enhance the Material's Performance or Reactivity One embodiment is a method of applying photon energy to a dental material to enhance the material's performance or reactivity via photochemical effects. This method is succinctly different and separate from photodynamic therapy and the use of photosensitizers. One aspect is the use of photon energy within the specified range to photopolymerizable dental materials, which further increases the mechanical properties of the dental materials. Without being bound by any theory, this can be performed using the two-photon effect if the proper wavelengths or electron volts are matched to the photoinitiator. For example, to polymerize a material containing camphoroquinone via the two-photon effect, applying photon energy in a band from 880 nm-960 nm can be utilized.

Another embodiment is the use of photon energy to stimulate photochemical effects including photodegradation (i.e. the alteration of material by light, which can include oxidation and free radical generation), photobleaching (i.e. photochemical alteration of a dye to reduce or remove the dyes visible color or fluorescent properties) or photocatalysis (i.e. the acceleration of a chemical reaction by light) of a dental material. Clinically, this may be useful to promote disinfection properties, esthetic properties, and safety. With regard to endodontic irrigants, the application of photon energy can be used to enhance the disinfection properties of commonly used irrigations such as sodium hypochlorite or chlorhexidine whereby the reactivity or free radical generation is increased by photon energy at certain wavelengths. The aforementioned methods above can be further enhanced by the incorporation of additives to the dental material further described herein.

Additives for Improved Heating Via Enhanced Energy Conversion Efficiency and Heat Transfer Another embodiment includes a method for improving the heating of a dental material by adding one or more heating additives to the dental material or dental material container. In some aspects, the heating additive is a photon energy absorption enhancer or a thermal conductivity enhancer. As described herein, the addition of heating additives including certain photon energy absorption enhancers (e.g., absorbing dyes) and thermal conductivity enhancers to the dental material and/or the dental material's container to increase the photon energy absorption, energy conversion efficiency from photon energy to heat, and/or material heating rate. In some aspects, the methods described herein include adding one or more heating photon energy absorption enhancers, one or more thermal conductivity enhancers or any combination thereof to a dental material or dental material container.

Suitable photon energy absorption enhancers exhibit one or more of the following properties: high absorbance between, (e.g., 0.49 eV-2.38 eV (i.e., 2500 nm-520 nm)), high ultraviolet A absorbance between 3.93 eV-3.09 eV (315 nm-400 nm), biocompatible, doesn't impart an unnatural tooth color to the material, compatible with the material and/or the container, stable, demonstrates heat stability (e.g., if used for injection molding), soluble and dispersible within the material and/or container, doesn't negatively affect the material's performance, and has a high conversion efficiency from photon energy to heat, or combinations of properties thereof. Additives that absorb ultraviolet light can be advantageous to use as many ultraviolet absorbing dyes are colorless, however, other dyes that absorb between 0.49 eV-2.38 eV may also be colorless or impart acceptable color to the dental material. For example, additives that impart a slight yellow or tan color may be acceptable to include in various shades of dental materials that are slightly yellow or tan. Exemplary and non-limiting photon energy absorption enhancers that satisfy some of the above properties include the following dye classifications: cyanine, polycyanine, fluorones, amminium, trisaminium, metal dithiolene complexes, anthroquinone, peri-arylenes (i.e., sexterrylenes and sexterrylenetetracarboxylic bisim ides), squaraines, phthalocyanines, phthalocyanines metal complexes, polymethine cyanines, porophyrines, chlorines, benzochlorines, thiazines, quantum dots, and single walled carbon nanotubes. Suitable commercially available dyes meeting one or more of the aforementioned criteria include, but are not limited to: Cy3, Cy5, fluorescein, indocyanine green, methylene blue, toluidene blue, absorbing dyes from Luminochem (e.g., LUNIR8/1; Budapest, Hungary), absorbing dyes from Epolin (i.e., Epolite 4113, 4831, 4019, 7809, 4105, 3130, 3169, 3036, 4019, 4129, 4113, 5262, 5839, 6661, 6158, 5636, 6084; Newark, N.J.) absorbing dyes from QCR Solutions (preferably NIR806F, NIR856A, NIR886A, NIR848A, NIR949A, NIR728A, NIR700A, NIR739B; Port St. Lucie, Fla.). Below is a structure of Cy3 and Cy5, with higher wavelength cyanine dyes sharing a similar structure, and are advantageous since cyanine dyes have been shown to be biocompatible.

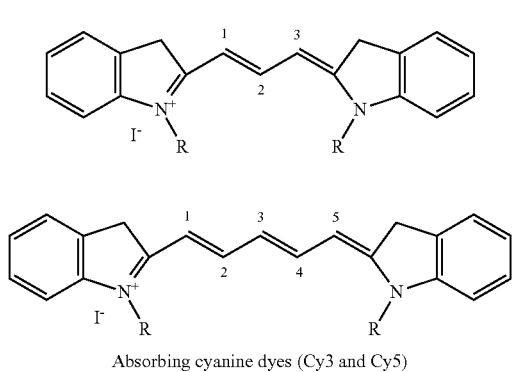

Absorbing cyanine dyes (Cy3 and Cy5)

In another aspect, the photon energy absorption enhancer is added to the dental material or dental material's container at a concentration to yield an absorbance/optical density value greater than or equal to 1 and at a photon energy within the disclosed photon energy range.

Figure 2:
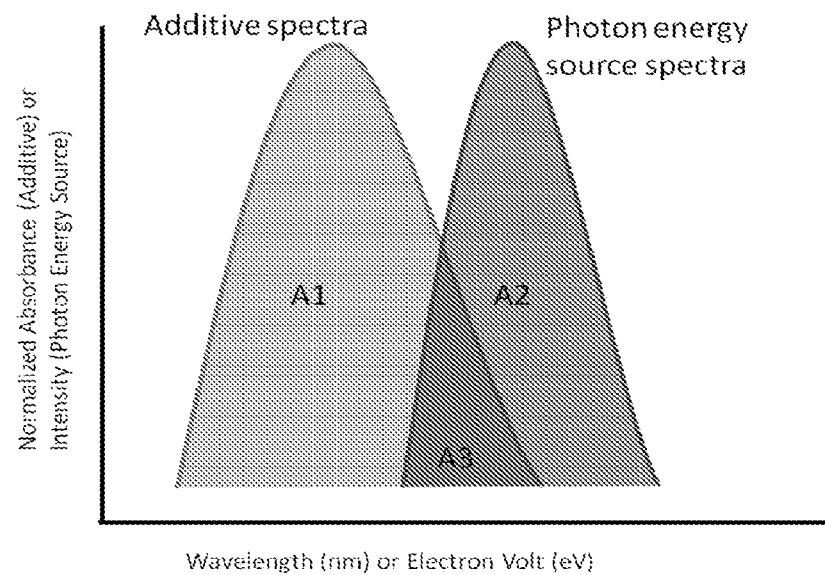
FIG. 2 is an area-intersect figure. A1=area-under-the-curve (AUC) for the normalized additive spectra, A2=AUC for the normalized photon energy source spectra, A3=area-intersection of the additive's spectra and the photon energy source's emission spectra. In some aspects, A3 is at least 10% of either A1 or A2. In some aspects, A3 is at least 25% of either A1 or A2. In some aspects, A3 is at least 50% of either A1 or A2.

The selected photon energy absorption enhancer, the spectra of the photon energy absorption enhancer, and the spectra of the photon energy source represent important aspects for achieving a desired overall heating performance. Referring to FIG. 2, an area-intersection (A3) of the photon energy absorption enhancer normalized absorbance (A1) spectra and the photon energy source's normalized emission spectra (A2) must have at least some overlap to achieve improved photon energy absorption and subsequent heating. In one aspect, the area-intersection of the photon energy absorption enhancer normalized absorbance spectra and the photon energy source's normalized emission spectra must be at least 10% of the area-under-the-curve for either the additive or the photon energy source. In another aspect, this area-intersect is at least 25%. In another aspect, this area-intersect (A3) is at least 50%.

In another aspect, one or more photon energy absorption enhancers is added to the dental material at a concentration of about 0.001%-10% (wt %) to increase the photon energy absorption of the dental material. In another aspect, one or more photon energy absorption enhancers is added to the dental material at a concentration of about 0.005%-7% (wt %). In another aspect, one or more photon energy absorption enhancers is added to the dental material at a concentration of about 0.01%-3% (wt %). In another aspect, one or more photon energy absorption enhancers is added to the dental material at a concentration of about 0.01%-1% (wt %). In another aspect, one or more photon energy absorption enhancers is added to the dental material at a concentration of about 0.001%, about 0.005%, about 0.01%, about 0.05%, about 0.1%, about 0.2%, about 0.4%, about 0.8%, about 1%, about 2%, about 3%, about 4%, about 5%, about 6%, about 7%, about 8%, about 9%, or about 10% (wt %).

In another aspect, one or more photon energy absorption enhancers is added to the dental material container at a concentration of about 0.1%-25% (wt %) to increase the photon energy absorption of the dental material container. In another aspect, one or more photon energy absorption enhancers is added to the dental material container at a concentration of about 0.1%-20% (wt %). In another aspect, one or more photon energy absorption enhancers is added to the dental material container at a concentration of about 0.1%-15% (wt %). In another aspect, one or more photon energy absorption enhancers is added to the dental material container at a concentration of about 0.1%-10% (wt %). In another aspect, one or more photon energy absorption enhancers is added to the dental material container at a concentration of about 0.1%-5% (wt %). In another aspect, one or more photon energy absorption enhancers is added to the dental material container at a concentration of about 0.1%-1% (wt %). In another aspect, one or more photon energy absorption enhancers is added to the dental material container at a concentration of about 0.1%, about 0.5%, about 1%, about 2%, about 4%, about 5%, about 7%, about 9%, about 11%, about 13%, about 15%, about 17%, about 20%, or about 25% (wt %).

In another aspect, one or more thermal conductivity enhancers is added to the dental material. Suitable thermal conductivity enhancers improve the thermal conductivity of the material and/or the material's container. This allows heat to more quickly disperse throughout the material and/or material's container, or improve the conductive transfer of heat between the material and its container. Exemplary and non-limiting additives to improve thermal conductivity include: graphite particles, graphene particles, ceramic particles (e.g. metal nitrides, boron nitride, silicon carbide, and silicon nitride), metal oxide particles (e.g. aluminum oxides), metal particles, and carbon nanotubes. In another aspect, one or more thermal heating additives is added to the dental material at a concentration of about 0.01%-80% (wt %). In another aspect, one or more thermal heating additives is added to the dental material at a concentration of about 0.01%-50% (wt %). In another aspect, one or more thermal heating additives is added to the dental material at a concentration of about 0.01%-30% (wt %). In another aspect, one or more thermal heating additives is added to the dental material at a concentration of about 0.01%-10% (wt %). In another aspect, one or more thermal heating additives is added to the dental material at a concentration of about 0.01%-1% (wt %).

In another aspect, one or more thermal conductivity enhancers is added to the dental material container. Suitable thermal conductivity enhancers improve the thermal conductivity of the material and/or the material's container. This allows heat to more quickly disperse throughout the material and/or material's container, or improve the conductive transfer of heat between the material and its container. Exemplary and non-limiting additives to improve thermal conductivity include: graphite fibers, graphene flakes, ceramic particles (e.g. metal nitrides, boron nitride, silicon carbide, and silicon nitride), metal oxides (e.g. aluminum oxides), metal particles, and carbon nanotubes. In another aspect, one or more thermal heating additives is added to the dental material container at a concentration of about 0.01%-80% (wt %). In another aspect, one or more thermal heating additives is added to the dental material container at a concentration of about 0.01%-50% (wt %). In another aspect, one or more thermal heating additives is added to the dental material container at a concentration of about 0.01%-30% (wt %). In another aspect, one or more thermal heating additives is added to the dental material container at a concentration of about 0.01%-10% (wt %). In another aspect, one or more thermal heating additives is added to the dental material container at a concentration of about 0.01%-1% (wt %).

Additives for Improving Material Polymerization (Photoinitiator and Coinitiator)

In another embodiment, a photopolymerization enhancer system is incorporated into a photopolymerizable dental material composition. The inclusion of such a system can improve polymerization, depth-of-cure, and degree-of-conversion using photon energy. The photopolymerization enhancer system described herein is succinctly different from other known photopolymerization systems because it includes a type I photoinitiator and a type II photoinitiator with a coinitiator or two type II photoinitiators with coinitiator(s), wherein at least one type I or type II photoinitiator is activated photon energy in a suitable range. In some aspects, the range of photon energy in which at least one of the photoinitiators is activated is about 0.49 eV-2.38 eV (2500 nm-520 nm), herein referred to as a "specified photoinitiator."

In one aspect, the photopolymerization enhancer system includes a type I photoinitiator and a type II photoinitiator with at least one coinitiator, wherein at least one or all of the photoinitiators is a specified photoinitiator. In another aspect, the photopolymerizable enhancer system includes two type II photoinitiators with at least one coinitiator, wherein one or all of the photoinitiators is a specified photoinitiator. In another aspect, the coinitiator is present at a concentration that is greater than or equal to the specified photoinitiator. In another aspect, the coinitiator and the other non-specified photoinitiator is present at a concentration that is greater than or equal to the specified photoinitiator. In another aspect, the combination of the coinitiator and the other non-specified photoinitiator is present at a concentration that is greater than or equal to the specified photoinitiator. In another aspect, at least one of the coinitiators is borate V. In another aspect, the specified photoinitiator is incorporated at a concentration of about 0.0001%-2% by weight of the total photopolymerizable dental material. In another aspect, the specified photoinitiator is incorporated at a concentration of about 0.0001%-1% by weight of the total photopolymerizable dental material. In another aspect, the specified photoinitiator is incorporated at a concentration of about 0.0001%-0.5% by weight of the total photopolymerizable dental material.

In another aspect, the photopolymerization enhancer system includes a type I photoinitiator and a type II photoinitiator with at least one coinitiator, or two type II photoinitiators with at least one coinitiator, wherein the specified photoinitiator is incorporated at a concentration of 0.0001%-0.5% by weight of the total photopolymerizable dental material, wherein the coinitiator(s) and the other photoinitiator is present at a concentration greater than or equal to the specified photoinitiator, wherein at least one of the coinitiators is borate V. In another aspect, the photopolymerizable enhancer system includes a type I photoinitiator and a type II photoinitiator with at least one coinitiator, or two type II photoinitiators with at least one coinitiator, wherein the specified photoinitiator is incorporated at a concentration of 0.001%-0.1% by weight of the total photopolymerizable dental material, with at least one of the coinitiators is borate V that is at least 10 times more concentrated than the specified photoinitiator, and with the other photoinitiator at a concentration greater than or equal to the specified photoinitiator.

In another aspect, the specified photoinitiator or coinitiator added to the photopolymerizable dental material is capable of losing its visible color (i.e., it becomes bleached or colorless) as a result of the application of photon energy of between 0.49 eV-1.90 eV (2500 nm-650 nm) or 1.23 eV-2.06 eV (1000 nm-600 nm) and/or is consumed during the photopolymerization process occurring after the application of photon energy of between 0.49 eV-1.90 eV (2500 nm-650 nm) or 1.23 eV-2.06 eV (1000 nm-600 nm). During a clinical application, the photopolymerizable dental material (e.g., a dental composite) can start as a distinct color, and change to the desired tooth shade once it is cured. This property gives the clinician the benefit of visual confirmation of a completed cure.

In another aspect, the specified photoinitiator absorbs photon energy between 0.49 eV-1.90 eV (2500 nm-650 nm) and photobleaches or becomes colorless. In another aspect, the specified photoinitiator facilitates material curing via increased radical formation and simultaneously bleaches as formed radicals deplete. Thus, in some aspects, the specified photoinitiator participates in the curing process and provides a visible change to indicate complete curing. In these aspects, the specified photoinitiator is used in conjunction with another photoinitiator and/or co-initiators at the concentrations disclosed herein.

Exemplary and non-limiting type I photoinitiators that can be used in conjunction with the specified photoinitiator include: TPO (diphenyl(2,4,6-trimethylbenzoyl)phosphine oxide), 2-Benzyl-2-(N, N-dimethylamino)-1-(4-morpholinophenyl)-butane-1-one (BDMB), 2,2-dimethoxy-2-phenylacetophenone (DMPA), Bis-acylphosphine oxide (BAPO), acyl germane derivatives, benzoin ethers, benzyl ketals, α-dialkoxyacetophenones, α-hydroxyalkylphenones, α-aminoalkylphenones, acylphosphine oxides, and fluorone dyes. Exemplary and nonlimiting type II photoinitiators that can be used in conjunction with the specified photoinitiator include: 1-phenyl 1,2-propanedione (PPD), camphoroquinone (CQ), ethyl-4-(dimethylamino)benzoate (EDB), benzil (BZ) and cyanine dyes. Additional suitable photoinitiators that may be used in conjunction with the specified photoinitiator include, but are not limited to: acetophenones, titanocene, germane based compounds, benzophenone derivatives, dibenzoylferrocene, iridium complexes, pyrene derivatives, thiobarbituric acid derivatives, benzyl and benzoin compounds, benzophenones, thioxanthones, sulfoniums, iodoniums, peri-Arylenes (particularly sexterrylenes, specifically Sexterrylenetetracarboxylic Bisim ides), squaraines, phthalocyanines, and phthalocyanines metal complexes, polymethine cyanines, porophyrines, chlorines, benzochlorines, thiazines and a cyanin-based photoinitiator shown as structure S1. Commercially available photoinitiators include, but are not limited to: photoinitiators from Spectra Group Limited, Inc. (H-Nu 660, H-Nu 780, H-Nu 815.

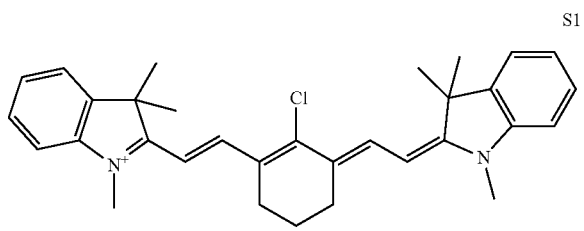 [SMILES: CN1/C(=C/C=C2\CCCC(/C=C/C3=[N+](C)c4ccccc4C3(C)C)=C2Cl)C(C)(C)c2ccccc21]
S1

Exemplary and nonlimiting classes of co-initiators that may be used with the type I and specified photoinitiator, or the type II and specified photoinitiator include: amine-based co-initiators (e.g. ethyl-4-dimethylaminobenzoate (DMABE), 4-dimethylamino benzonitril (DMABN), 2-N,N-dimethylamino ethyl methacrylate (DMAEMA) or other pyridinium-based compounds), borate-based co-initiators (e.g., butyltriphenylborate referred to as borate V, tetrabutylammonium tetrafluoroborate), and iodonium salts. Commercially available co-initiators include, but are not limited to: co-initiators from Spectra Group Limited, Inc. (e.g., borate V, H-Nu 254, which is an iodonium salt).

Additives for Improving the Material's Reactivity (Photocatalyst)

Another embodiment includes a method for improving the reactivity of a dental material by including one or more photocatalysts. The incorporation of a photocatalyst is thought to absorb the applied photon energy and acts as a photocatalyst to enhance other dental material properties. Exemplary and non-limiting photocatalysts include those such as metal oxides. A potential application of this photocatalyst is to place a metal oxide within an endodontic irrigant or oral rinse and subject it to photon energy for improved disinfection.

Methods for Treating a Patient with a Dental Material

Another embodiment described herein is a method of treating a patient with a dental material comprising heating the dental material above ambient temperature with a device using photon energy from a photon energy emission source and applying the heated dental material to a surface of the tooth or a tooth cavity, prior to curing of the material (if applicable, i.e. prior to curing of dental photopolymerizable materials).

As described herein, the photon energy comprises an energy of about 0.49 eV-2.38 eV (2500 nm-520 nm) or about 1.23 eV-2.06 eV (1000 nm-600 nm). In one aspect, the dental material is a dental photopolymerizable material. In another aspect, the emitted photon energy, which heats the dental material, does not prematurely cure or cause the material to polymerize and is at a suitable absorption wavelength of the dental material, a dental material container, or a heating additive described herein.

The dental photopolymerizable material includes composite resins, highly filled composite resins, glass ionomer resins, sealants, cements, cavity liners, or combinations thereof. Following application of the heated dental material, the method for treating a patient further includes curing the dental material. In one aspect, the curing further includes applying a second source of photon energy with an absorption spectra of a photopolymerizable material that is present in the dental material to initiate polymerization. Thus, in this aspect, during the treatment of a patient, an applied photon energy for heating the dental photopolymerizable material does not overlap with an absorbance of a photoinitiator present in the dental photopolymerizable material.

Device for Heating and Dispensing Dental Materials

The inventive devices described herein allow for the creation of dental composites with higher filler content. Higher filler content is desired as it leads to less shrinkage during curing and harder, more wear resistant, and longer lasting restorations. However, highly filled composite is limited in use due to its low flowability, high extrusion force for dispensing, and poor shaping ability, leading to poor marginal adaptation. Preheating the photopolymerizable materials lowers the viscosity and reorders the molecular structure of the filler and monomer reducing internal stresses and heterogeneity thereby improving clinical use of highly filled composites. Additionally, preheating photopolymerizable materials and curing at an elevated temperature increases volumetric expansion of the composite (i.e. thermal expansion) which can offset the volumetric reduction caused by polymerization. This significantly reduces composite shrinkage, leakage, stresses, and post-operative pain.

Thus, another embodiment is a device capable of emitting photon energy between 0.49 eV-2.38 eV (i.e. 2500 nm-520 nm) can be used to heat and/or dispense dental materials. In one aspect, the utilized photon energy is between 1.23 eV-2.06 eV (1000 nm-600 nm) or 1.23 eV-1.77 eV (i.e. 1000 nm-700 nm) to heat and dispense dental materials as the applied photon energy is invisible to the human eye and safer. The photon energy source is limited to an electroluminescence source, such as a light emitting diode (LED) or a laser diode, and provides optical power between 0.5 W and 20 W or between 1 W and 8 W.

Suitable devices described herein may be cordless and furthermore incorporate a rechargeable energy source, such as a lithium ion battery, super capacitor, lithium polymer battery, nickel cadmium battery, or nickel metal hydride battery. In another aspect, the device includes a corn pule or container having a dental material therein. The compule can be removed from the device after application of the dental material and replaced with another compule or container for a subsequent application in the same or a subsequent procedure.

In another aspect, the photon energy source is arranged in close proximity to the compule or container to ensure efficient energy transfer. In another aspect, the distance between the photon energy source and compule or container is less than one centimeter. Alternatively, in another aspect, the photon energy source is collimated via a lens or fiber optic to ensure higher energy transfer to the compule or container and/or allow the photon energy source to be located at a greater distance from the compule or container.

In another aspect, the tool or wand effectively thermally manages the photon energy source in order to keep the device from elevated thermal temperatures that can degrade the dental material or is dangerous to an operator of the device or a patient being treated with the device. This can be accomplished by placing the photon energy source on a primary heat sink, such as a printed circuit board or a metal clad printed circuit board, which may be further coupled to a secondary or tertiary heat sink, which may be contained within the device housing or may comprise the device housing. Additionally, the use of a heat pipe can help facilitate thermal management. Through proper thermal management the device body, and touchable surfaces, should not reach unsafe elevated temperatures, which are commonly defined as temperatures above approximately 50° C. for medical devices.

In another aspect, to minimize the negative impacts of excessive or undesirable temperatures occurring to the dental materials, the device includes a sensor to control the applied photon energy. A temperature sensor can be used to monitor the temperature of the dental material within the tool/wand during the application of photon energy and/or determine when the object is at a desired temperature and feedback this information to the applied photon energy source to reduce or remove the power output of the emitter as detailed in the block diagram illustrated in FIG. 37. Exemplary and non-limiting temperature sensors include a thermistor, IR temperature sensor, thermopile, thermocouple, or a resistance temperature detector (RTD). The temperature sensor can also be part of the object that is being heated instead of being part of the device. This can be done by embedding a thermistor on the object or making the object out of a material that changes its electrical properties (i.e. resistance, capacitance, or inductance) in relation to its change in temperature, and then by making an electrical connection with the device. Suitable temperature sensors are available from Vishay Dale (TFPT), Panasonic (AMG88), Texas Instruments (TMP007), Digilent, Inc. (240-080), and TE Connectivity (Ni1000SOT).

Furthermore, it is envisioned that once the object reaches the desired temperature, the device can use pulse-width modulation (PWM), proportional-integral-derivative controller (PID), or another control loop feedback system approach to maintain the desired temperature without reaching undesirable temperatures which can have a negative impact on the dental material. Furthermore, in lieu of or in addition to a temperature sensor, another sensor can be used to determine how absorbing the object is and adjust power to the photon energy source accordingly to account for differences in the dental materials absorbance and required power and on time to reach a desired temperature. This can be achieved with a thermopile, RGB sensor, proximity sensor, phototransistor, photodiode, ambient light sensor, CMOS sensor, or CCD sensor to either directly or indirectly determine the absorption or color of the object for a specific wavelength of photon energy, either by measuring reflectance or transmittance. Suitable sensors are available from Vishay Semiconductor (VCNL4020X01, VEML6040), Rohm Semiconductor (BH1680FVC), Texas Instruments (TMP007), Everlight Electronics Co Ltd (PD15-22C/TR8), Kingbright (APA3010P3BT), OmniVision Technologies Inc. (OV09740-A46A), and Toshiba (TCD1103GFG).

In addition, the same sensor used for determining absorption, or a separate implementation of one of the aforementioned sensor, can be implemented so that the device only works with a manufacturer's specific object or container or material, as the sensor's measured value can serve as a "fingerprint" to identify the inserted object or container or material to implement a closed platform system. This would allow manufacturers to ensure only their product is heated using this device. Furthermore, as a safety feature, the device can incorporate using any of the above mentioned sensors to determine if the object is present prior to starting or during heating, such that photon energy is only emitted when an object is present.

According to another aspect, the device used for heating and dispensing includes a curing light source at 365 nm-500 nm and an additional source of photon energy between 0.49 eV-2.38 eV (i.e. 2500 nm-520 nm), between 1.23 eV-2.06 eV (1000 nm-600 nm), or between 1.24 eV-1.77 eV (i.e. 1000 nm-700 nm) that can be activated and directed at the composite after application of the composite in order to heat and/or cure the composite where applied. Both the curing light source and photon energy source would each emit between an optical power of between 500 mW and 3 W or between 700 mW and 1.5 W of optical power. In another aspect, the photon energy can be applied prior, simultaneously, or after a short delay of about a couple seconds compared to the curing light source to modulate the resultant dental composite properties. The photon energy can be directly absorbed by the composite material (i.e. constituents within the composite material such as monomers and fillers, or incorporated additives), or an additive to the composite material to heat the dental material during curing with one of the aforementioned additives that may also be used for heating prior to curing.

In another aspect, the curing light and photon energy sources are arranged distally on the device to facilitate access in the oral cavity. Alternatively, in another aspect, the curing light and/or photon energy source can be collimated via a lens or fiber optic to ensure higher energy transfer to the placed material and/or allow the curing and photon energy sources to be located at a non-distal position in the device. The device effectively thermally manages the curing light and photon energy sources in order to keep the device from elevated thermal temperatures, which degrades the dental composite material or is dangerous to an operator of the device or a patient being treated with the device. This can be accomplished by placing the photon energy source on a primary heat-sink (a printed circuit board or a metal clad printed circuit board), which may be further coupled to a secondary or tertiary heat-sink, which may be contained within the device housing or may comprise the device housing/body. Additionally, the use of a heat pipe can help facilitate thermal management. Clinically, the use of the disclosed photon energy device and method can improve surface hardness, degree of conversion, depth of cure, reduce shrinkage and leakage, and can be used to improve incremental layering and curing of restoration material improving procedural efficiency. In another aspect, this can also be accomplished with a separate device that does not dispense the dental material and would be restricted to curing photopolymerizable materials, i.e. a multispectral curing light.

One embodiment described herein is a device according to any one of FIG. 14-16 or 28-32. In one aspect, the device has a package of photon emitters according to any one of FIG. 17-19 or 35.

Device for Enhancing the Cure of Photopolymerizable Dental Materials

According to another embodiment of the invention, a tool or wand can use photon energy to heat the photopolymerizable dental material above ambient temperature and cure the photopolymerizable dental material. This results in curing of the photopolymerizable dental material at an elevated temperature in situ and/or in vivo which has significant benefits to the mechanical properties of the photopolymerizable dental material. In one aspect, this device has a thermally conductive body, and in another aspect, this device is elongated to facilitate easy access in the mouth. Additionally, the device includes at least four discrete distally mounted photon energy emission sources that produce at least two discrete emission spectra. In one aspect, these photon energy emission sources consist of light emitting diodes (LEDs). At least one LED emission spectra is used for curing the photopolymerizable dental material, and at least one LED emission spectra is used to elevate the photopolymerizable dental material's temperature above ambient prior to or during curing. In one aspect, the emission source for curing the photopolymerizable dental material emits light between 365 nm-500 nm, and at a power between 500 mW and 3 W of optical power. In another aspect, the emission source for curing the photopolymerizable dental material emits light between 420 nm-490 nm, and at a power between 700 mW and 1.5 W of optical power. In another aspect, the emission source for elevating the photopolymerizable dental material's temperature above ambient temperature during curing emits light between 520 nm-2500 nm, and at a power between 500 mW and 3 W of optical power. In another aspect, the emission source for elevating the photopolymerizable dental material's temperature above ambient temperature during curing emits light between 600 nm-1000 nm, and at a power between 700 mW and 2 W of optical power.

It was discovered that the spatial orientation of these at least four LEDs ensures a near uniform beam profile, such that optical power does not vary considerably throughout the illumination field. In one aspect, one LED is centrally located within the distal head of the device, and at least three LEDs are located radially about the centrally located LED. These at least four LEDs can be located on the same PCB or separate parallel PCBs (see FIGS. 17-19 and 35), and may be located on the same plane or separate parallel planes. However, in another aspect, the at least four LEDs emit their beam profiles in generally the same direction so the beam profiles can be collimated to provide an even illumination field. Furthermore, if more than three radially spaced LEDs are to be incorporated, the spacing (i.e. angular separation) between LEDs should be equal for uniform beam profile. For example, three LEDs should be angularly separated by about 120° (see FIGS. 17 and 35), four LEDs should be angularly separated by about 90°, and five LEDs should be angularly separated by about 72°. In another aspect, one centrally located LED is contained on its own PCB, which is surrounded by three LEDs contained on a separate PCB, wherein the three LEDs are placed on the same plane 120° apart.

Depending on the clinical procedure, the various LEDs may have different emission output powers and durations themselves or respect to one another. For example, the output of the centrally located LED may lead, lag, or is simultaneously used with the output of the at least three radially located LEDs. If the clinician wanted to soften and/or manipulate the photopolymerizable dental material in situ and/or in vivo the device may incorporate a setting that only illuminates the photopolymerizable dental material to elevate the material's temperature, which subsequently decreases the material's viscosity. At this point, the material can be manipulated to the desired shape/structure prior to curing. Alternatively, elevating the photopolymerizable dental material's temperature in situ and/or in vivo, without physical manipulation, is also possible and would be advantageous to decrease its viscosity and improve conformation to the tooth surface. The heated photopolymerizable dental material can then be cured in situ and/or in vivo at an elevated temperature while it is most conformed to the tooth surface. An example setup to achieve this situation would be to illuminate the photopolymerizable dental material with the spectrum of 520 nm-2500 nm to elevate its temperature for about 5 to about 30 seconds immediately prior to illuminating the photopolymerizable dental material with the spectrum of 365 nm-500 nm to cure for about 3 to about 30 seconds. In one aspect, the device has 2-5 different preprogrammed settings for various clinical procedures/preferences, wherein each mode has differing power, duration, and overlap characteristics of the at least two emission spectrums, wherein at least one emission spectra is within the specified photon energy range.

In another aspect, to ensure proper thermal management of the photon energy emission sources (e.g. LEDs), the photon energy emission sources is coupled to a primary heat sink located within the device. In another aspect, these primary heat sinks are coupled to the thermally conductive body. Alternatively, in another aspect the primary heat sink for the at least three radially located LEDs may be coupled to the primary heat sink of the centrally located LED, which is then coupled to the thermally conductive body. Lastly, in another aspect, these photon energy emission sources are in electrical communication to a direct current power source. In another aspect, this direct current power source is a detachable, rechargeable power source, such as a lithium ion battery.

Optionally, other dental devices can be incorporated within this multispectral curing device, which may include, but is not limited to: a transilluminator.

Another embodiment is a device according to any one of FIGS. 33-34. In one aspect, the device has a package of photon emitters according to any one of FIGS. 17-19 and 35.

Compositions of Dental Materials and Containers

Another embodiment is a dental material composition. In some aspects, the dental material is a photopolymerizable dental material composition. The dental material compositions described herein have enhanced energy conversion efficiency, heat transfer, and/or polymerization characteristics.

In some aspects the photopolymerizable dental material compositions described herein include: acrylate monomers (e.g., triethylene glycol dimethacrylate, TEGDMA, urethane dimethacrylate, UDMA, and bisphenol-A-glycidyldimethacrylate, bis-GMA, etc), inorganic fillers (e.g., glasses or ceramics, i.e., silicon dioxide, crystalline silica, borosilicate glass, zirconium oxide, zirconia-silica, etc), photopolymerization systems (e.g., camphoroquinone with amine-based co-initiators), and optionally one or more pigments or colorants to match tooth color, and optionally one or more heating additives, optionally a polymerization enhancer system and optionally one or more thermal conductivity enhancers. As described herein, the heating additive, polymerization enhancer system, and thermal conductivity enhancers improve the material's energy conversion efficiency, heat transfer properties, and/or polymerization.

In one aspect, the dental material composition includes about 1% to about 40% by weight of acrylate monomers. In another aspect, the dental material composition includes about 5% to about 30% by weight of acrylate monomers. In another aspect, the dental material composition includes about 5% to about 20% by weight of acrylate monomers. In another aspect, the dental material composition includes about 5% to about 15% by weight of acrylate monomers. In another aspect, the dental material composition includes about 1%, 5%, 10%, 15%, 20%, 25%, 30%, 35%, or 40% by weight of acrylate monomers.

In another aspect, the dental material composition includes about 30% to about 95% by weight of an inorganic filler. In another aspect, the dental material composition includes about 60% to about 95% by weight of an inorganic filler. In another aspect, the dental material composition includes about 5% to about 20% by weight of an inorganic filler. In another aspect, the dental material composition includes about 5% to about 15% by weight of an inorganic filler. In another aspect, the dental material composition includes about 1%, 5%, 10%, 15%, 20%, 25%, 30%, 35%, or 40% by weight of an inorganic filler monomers.

In some aspects, the heating additive, polymerization enhancer system and thermal conductivity enhancer is provided into the dental material compositions described herein at the concentrations described by the embodied methods above.

An exemplary embodiment of the photopolymerizable dental material is disclosed in tables 1-2. This exemplary dental material composition includes an absorbing dye (e.g., LUNIR1) as a photon energy absorption enhancer to significantly increase the heating of the material. As described herein additional heating additives and/or polymerization enhancers may be added to the disclosed composition to further enhance the material's energy conversion efficiency, heat transfer properties, and/or polymerization characteristics. Alternatively, other additives may be incorporated to tailor the material's absorption properties to any photon energy in the disclosed photon energy range.

TABLE 1

Exemplary Photopolymerizable Dental Material Composition Having a Photon Energy Absorption Enhancer

| Constituent | Concentration range (%) | Example concentration (%) |
|---|---|---|
| Acrylate monomers | 5-30% | 13.89% |
| Inorganic fillers | 60-95% | 85.00% |
| Camphorquinone photoinitiator | 0.001-0.5% | 0.05% |
| Amine-based co-initiator(s) | 0.001-1% | 0.10% |
| Hydroquinone (stabilizer) | 0.0001%-0.05% | 0.01% |

TABLE 2

Exemplary Photopolymerizable Dental Material Composition Having a Photon Energy Absorption Enhancer

| Constituent | Concentration range (%) | Example concentration (%) |
|---|---|---|
| Acrylate monomers | 5-30% | 13.89% |
| Inorganic fillers | 60-95% | 84.90% |
| Photoinitiator(s) | 0.001-0.5% | 0.10% |
| Co-initiator(s) | 0.001-1% | 0.20% |
| Stabilizer | 0.0001%-0.05% | 0.01% |
| Heating additive | 0.001%-10% | 0.90% |

A further exemplary embodiment is provided in table 3. This exemplary dental material composition includes a photopolymerization enhancer system including two type II photoinitiators (cam phorquinone and H-Nu 660; of which H-Nu 660 is the specified photoinitiator as described herein) and another co-initiator (borate V) to significantly increase polymerization the material. This composition also results in a formulation that changes color from "blue/green" to "tooth shade," which provides confirmation to the clinician that the composite is sufficiently cured (see FIG. 27). As described herein additional heating additives and/or polymerization enhancers may be added to the disclosed composition to further enhance the material's energy conversion efficiency, heat transfer properties, and/or polymerization characteristics. Alternatively, other additives may be incorporated to tailor the material's absorption properties to any photon energy in the disclosed photon energy range.

TABLE 3

Exemplary Dental Material Composition Having a Photopolymerization enhancer system

| Constituent | Concentration range (%) | Example concentration (%) |
|---|---|---|
| Acrylate monomers | 5-30% | 17.845% |
| Inorganic fillers | 60-95% | 85% |

TABLE 3-continued

Exemplary Dental Material Composition Having a Photopolymerization enhancer system

| Constituent | Concentration range (%) | Example concentration (%) |
|---|---|---|
| Camphoroquinone photoinitiator | 0.001-0.5% | 0.05% |
| Amine-based co-initiator(s) | 0.001-1% | 0.05% |
| H-Nu 660 photoinitiator | 0.001-0.5% | 0.005% |
| Borate V co-initiator | 0.01%-5% | 0.05% |

Another exemplary composition is provided in table 4. This exemplary dental material composition includes a dental composite material comprising two type II photoinitiators (camphoroquinone and H-Nu 660; of which H-Nu 660 is the specified photoinitiator as described herein) and a co-initiator (borate V) to significantly increase polymerization the material. This composition also results in a formulation that changes color from "blue" to "tooth shade", which provides confirmation to the clinician that the composite is sufficiently cured. As described herein additional heating additives and/or polymerization enhancers may be added to further enhance the material's energy conversion efficiency, heat transfer properties, and/or polymerization characteristics. Alternatively, other additives may be incorporated to tailor the material's absorption properties to any photon energy in the disclosed photon energy range.

TABLE 4

Exemplary Dental Material Composition Having a Photopolymerization enhancer system

| Constituent | Concentration range (%) | Example concentration (%) |
|---|---|---|
| Acrylate monomers | 5-30% | 14.895% |
| Inorganic fillers | 60-95% | 84.95% |
| Camphoroquinone photoinitiator | 0.001-0.5% | 0.05% |
| H-Nu 660 photoinitiator | 0.001-0.5% | 0.005% |
| Borate V co-initiator | 0.01%-5% | 0.1% |

A further example of a photopolymerizable composition utilizing a photoinitiator system described herein is provided in tables 5-6, which are formulations for a dental sealant.

TABLE 5

Exemplary Photopolymerizable Dental Sealant Composition Having a Heating Additive

| Constituent | Concentration range (%) | Example concentration (%) |
|---|---|---|
| Acrylate monomers | 40-90% | 88.885% |
| Inorganic fillers | 1-20% | 10% |
| Photoinitiator | 0.001-0.5% | 0.05% |
| Additional photoinitiator | 0.001-0.5% | 0.005% |
| Stabilizer | 0.0001%-0.05% | 0.01% |
| Co-initiator(s) | 0.001-1% | 0.05% |
| Heating additive | 0.001%-10% | 1% |

TABLE 6

Exemplary Photopolymerizable Dental Sealant Composition Having a Heating Additive

| Constituent | Concentration range (%) | Example concentration (%) |
| --- | --- | --- |
| Acrylate monomers | 40-90% | 88.89% |
| Inorganic fillers | 1-20% | 10% |
| Photoinitiator | 0.001-0.5% | 0.05% |
| Stabilizer | 0.0001%-0.05% | 0.01% |
| Co-initiator(s) | 0.001-1% | 0.05% |
| Heating additive | 0.001%-10% | 1% |

Endodontic Filling Materials

Another embodiment, is a composition for dental materials, specifically endodontic filling materials such as gutta percha, which display enhanced energy conversion efficiency and/or heat transfer characteristics.

In one aspect, the disclosed composition for gutta percha endodontic filling includes the following constituents: gutta-percha or other polyisoprene derivatives, inorganic fillers (glasses or ceramics, e.g. zinc oxide, titanium oxide, silicon dioxide, crystalline silica, borosilicate glass, zirconium oxide, zirconia-silica, etc), a radiopacifier (e.g., barium sulfate, bismuth sulfate, tungsten), stabilizer(s) (e.g. antioxidants, butylated hydroxytoluene), waxes or resins (e.g., metal stearate complexes, zinc stearate, polyethylene glycol, paraffin wax, palmitates, carnauba wax, etc) and at least one heating additive to improve the material's energy conversion efficiency and/or heat transfer properties. These heating additives will be incorporated into the dental material (e.g. gutta percha) at concentrations described herein.

Another exemplary composition is provided in tables 7-8. This exemplary gutta percha endodontic filler dental material composition includes an absorbing dye (i.e., indocyanine green) as a photon energy absorption enhancer to significantly increase the heating of the material. Additional additives may be added to the disclosed composition to further enhance the material's energy conversion efficiency and/or heat transfer properties. Alternatively, other additives may be incorporated to tailor the material's absorption properties to any photon energy in the disclosed photon energy range.

TABLE 7

Exemplary Gutta Percha Dental Material Composition Having a Photon Energy Absorption Enhancer

| Constituent | Concentration range (%) | Example concentration (%) |
| --- | --- | --- |
| Gutta percha | 10-30% | 23% |
| Inorganic filler | 60-85% | 60% |
| Radiopacifier | 1.0-30% | 12% |
| Wax(es) and resin(s) | 0%-10% | 3% |
| Heating additive | 0.01%-10% | 2% |

TABLE 8

Exemplary Gutta Percha Dental Material Composition Having a Photon Energy Absorption Enhancer

| Constituent | Concentration range (%) | Example concentration (%) |
| --- | --- | --- |
| Gutta percha | 10-30% | 15% |
| Aluminum nitride | 50-85% | 60% |
| Barium sulfate | 1.0-35% | 20% |
| Paraffin | 0%-10% | 3% |
| Indocyanine green | 0.001%-10% | 2% |

Dental Material Housing

Another embodiment, is a dental material container, which displays enhanced energy conversion efficiency and/or heat transfer when irradiated with the disclosed photon energy.

The disclosed composition for dental material containers includes the following constituents: a thermoplastic resin (e.g. polycarbonate, polyamide, polypropylene, polyethylene, etc), and at least one additive to improve the material's energy conversion efficiency and/or heat transfer properties. The composition may also include colorants or other pigments, plasticizers, or other fillers (e.g. glass fibers, carbon black, etc.). With regard to photopolymerizable dental materials, such as a dental composite, the additive, colorant, pigment, or other filler should sufficiently block polymerization light from transmitting through the container to the composite, which would cure the photopolymerizable material inside the container.

Example compositions for a dental material's container are described in tables 9-14. The following tables below detail container formulations incorporating a heating additive to significantly increase the heating rate and overall temperature change of the material located within.

TABLE 9

Exemplary Dental Material Container Having a Heating Additive

| Constituent | Concentration range (%) | Preferred concentration (%) |
| --- | --- | --- |
| Thermoplastic resin | 50-99.9% | 95% |
| Heating additive | 0.1-50% | 5% |

TABLE 10

Exemplary Dental Material Container Having a Photon Energy Absorption Enhancer Heating Additive

| Constituent | Concentration range (%) | Preferred concentration (%) |
| --- | --- | --- |
| Polycarbonate | 50-99.9% | 95% |
| Epolight 7657 | 0.1-50% | 5% |

Additional additives can be added to the above compositions to further enhance the material container's energy conversion efficiency and/or thermal transfer properties. These additives would be incorporated at concentrations disclosed below. For example, boron nitride can be added to the composition to increase heat transfer properties of the container.

TABLE 11

Exemplary Dental Material Container Having Multiple Heating Additives

| Constituent | Concentration range (%) | Preferred concentration (%) |
| --- | --- | --- |
| Thermoplastic resin | 50-99.9% | 92% |
| Heating additive 1 | 0.1-50% | 5% |
| Heating additive 2 | 0.01%-20% | 3% |

TABLE 12

Exemplary Dental Material Container Having a Thermal Conductivity Enhancer and Photon Energy Absorption Enhancer Heating Additives

| Constituent | Concentration range (%) | Preferred concentration (%) |
| --- | --- | --- |
| Polycarbonate | 50-99.9% | 85% |
| Epolight 7657 | 0.1-50% | 5% |
| Boron nitride | 0.01%-20% | 10% |

Alternatively, other additives can be used to tailor the container's absorption properties to any photon energy in the disclosed photon energy range. Furthermore, other fillers can be added to enhance the material container's characteristics. For example, glass fibers can be added to increase the container's strength.

TABLE 13

Exemplary Dental Material Container Having Multiple Heating Additives and a Filler

| Constituent | Concentration range (%) | Preferred concentration (%) |
| --- | --- | --- |
| Thermoplastic resin | 50-99.9% | 71% |
| Heating additive 1 | 0.1-50% | 7% |
| Heating additive 2 | 0.01%-20% | 12% |
| Filler | 1%-20% | 10% |

TABLE 14

Exemplary Dental Material Container Having Multiple Heating Additives and a Filler

| Constituent | Concentration range (%) | Preferred concentration (%) |
| --- | --- | --- |
| Polycarbonate | 50-99.9% | 74% |
| Epolight 7657 | 0.1-50% | 1% |
| Boron nitride | 0.01%-20% | 15% |
| Glass fibers | 1%-20% | 10% |

Another embodiment is a process for making the dental container described herein that includes a thermoplastic resin and a heating additive. In one aspect, the method includes the process of heating a thermoplastic resin to at least its softening point. In another aspect, the method further includes maintaining and controlling the resin temperature to at least its softening point. In another aspect, the method further includes adding an additive at about 0.1-5%. Suitable additives include those, which have a high photon energy absorbance between 520 nm-2500 nm. In another aspect, the method includes while adding an additive and optionally a dispersant the temperature of the resin is maintained at its softening point. In another aspect, the method includes mixing and homogenizing a mixture containing the resin, additive, and optional dispersant while maintaining temperature to at least the resin's softening point. In another aspect, the method includes extruding a homogenized mixture that contains the resin, additive, and optional dispersant into a mold cavity including the dental material container shape and allowing it to cool prior to removal from the cavity. Alternatively, in another aspect, a homogenized and heated mixture containing the resin, additive, and optional dispersant is formed into pellets, which can be later used for injection molding a dental material container.

Another embodiment is a dental material container made by the process described above. The formed dental material container is suitable for being filled with a dental material. Further, the formed dental material container made by the process above and containing a dental material is suitable for being heated with photon energy to quickly heat a dental material as described herein.

EXAMPLES

Figure 3:
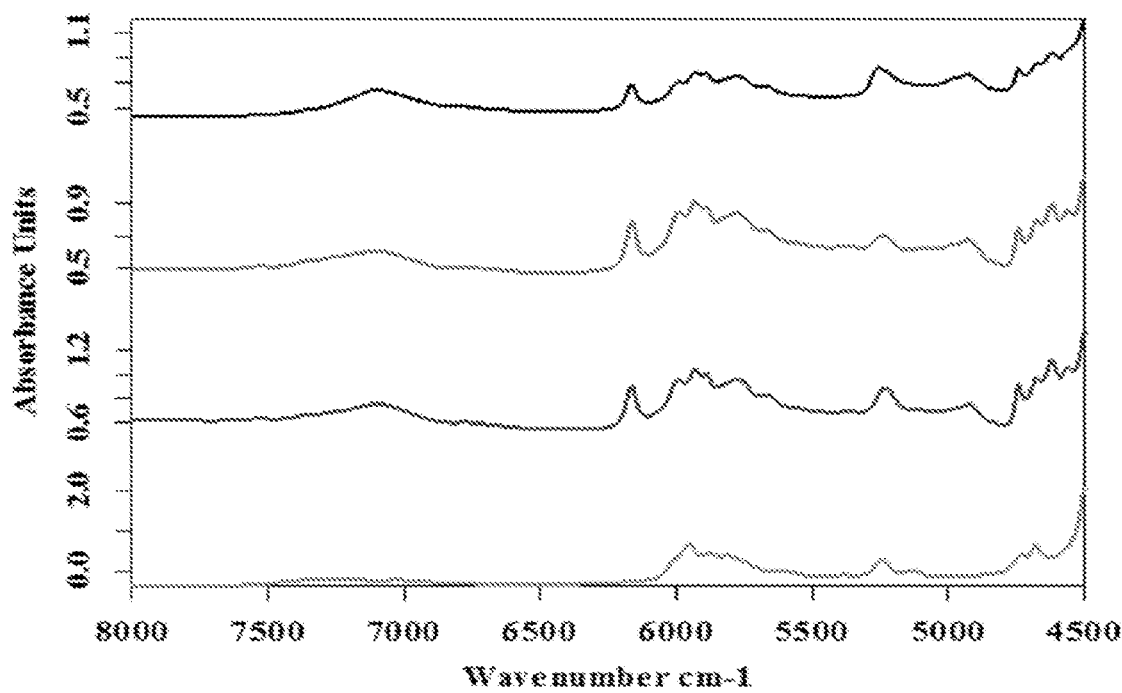
FIG. 3 is a graph of the absorption of three commercially available dental composite resin materials (also synonymously called dental composite materials) and a comparison to poly(methyl methacrylate) (i.e. acrylic). This figure demonstrates the similarities of dental composite near infrared absorbance characteristics and acrylic, due to the presence of acrylate-based monomers within the composite resin's composition. These absorbance characteristics can be exploited for efficient heating using photon energy. For example, targeting higher absorbance bands with photon energy will result in quicker heating of the dental material.

Example 1 Application of Photon Energy to Anesthetic, Gutta-Percha, Dental Composite and Dental/Endodontic Irrigants—Absorbance and Performance The benefits of the disclosed embodiments can be derived from the application of photon energy of dental materials including, but not limited to: anesthetic (reducing pain during injection), gutta-Percha (for endodontic root canal obturation), dental composites, sealants, cements, cavity liners, and glass ionomer resins (e.g., lowering viscosity, improving handling characteristics, decreasing voids, and improving mechanical properties post-cure) and endodontic irrigants (increasing efficacy and reactivity). For example, in FIG. 3, the absorbance of three composite materials, i.e., Filtek Supreme Ultra, Spectrum TPH3 and Esthet.X HA, is compared with that of acrylic, and illustrates that 3 leading composite brands show similar absorptions to acrylic material. This indicates that the primary composition of dental composite is the acrylic monomer, and that this is the primary structure attributing to its absorption, allowing for a particular wavelength band to be selected, corresponding to overtone bands, for heating the acrylic monomers and oligomers within the composite.

Figure 4:
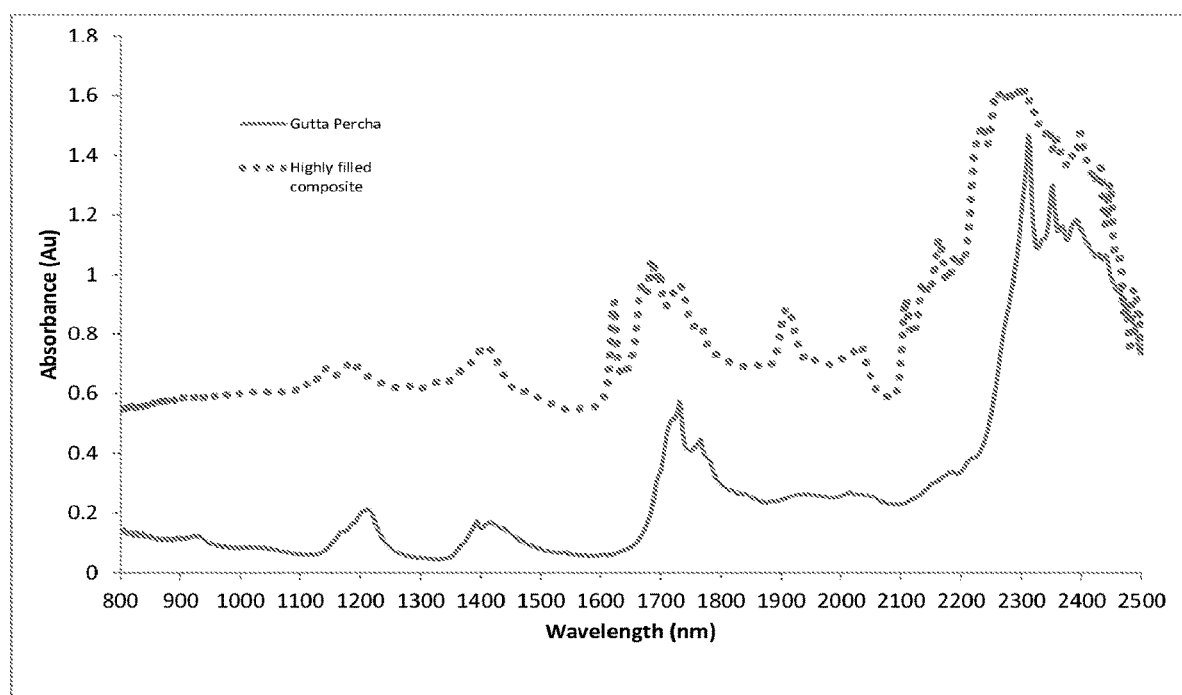
FIG. 4 is graph of the absorbance of gutta-percha and a highly filled dental composite material. These absorbance characteristics can be exploited for heating using photon energy, where higher absorbance would translate to increased photon energy conversion efficiency and faster heating rates.
Figure 5:
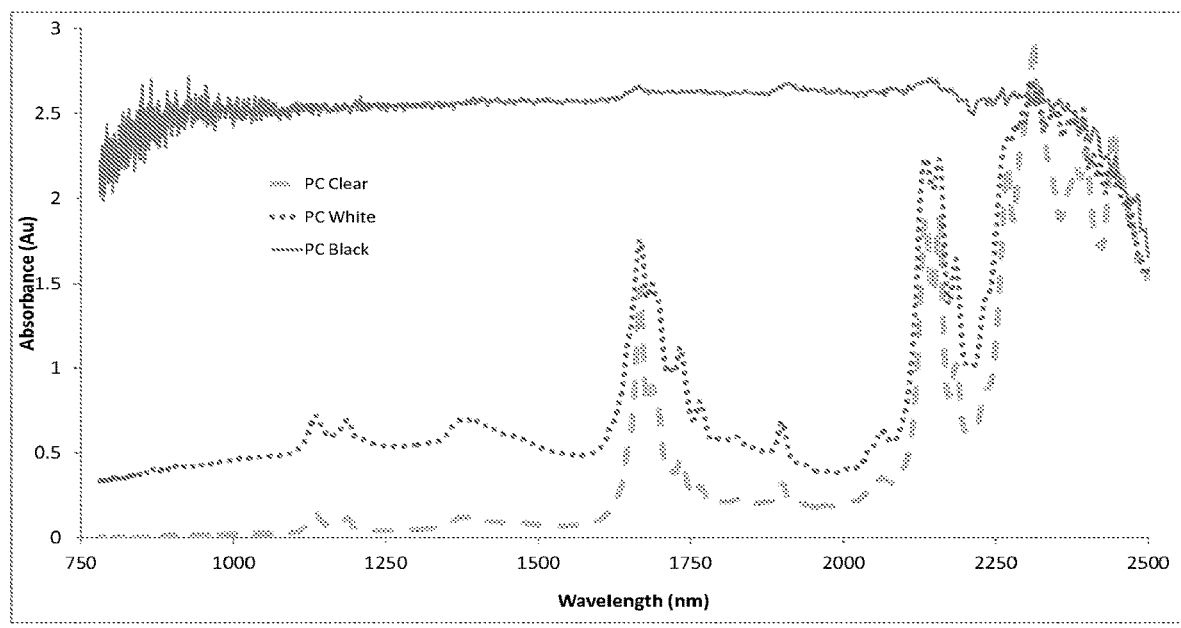
FIG. 5 is a graph of absorption curves for polycarbonate plastic with different pigments added to the thermoplastic resin. This figure demonstrates the dependency of near infrared absorbance depending on the color of a material, not solely on the material itself. Thus, thermoplastic colorant/pigment additives can be used to alter the absorbance characteristics of the material container. These absorbance characteristics can be exploited for heating using photon energy, where higher absorbance would translate to increased photon energy conversion efficiency and faster heating rates.

In addition, for dental materials including gutta purcha, which has the following structure:

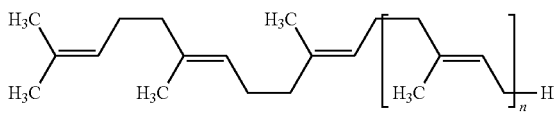

the targeted bond(s) for absorption and heating using near infrared IR photons in gutta-percha—is the terpene molecule, which has C—C single bonds and C═C double bonds. This is also clearly illustrated in FIG. 4 which illustrates the peaks for the various bonds and molecules in gutta-percha and a highly filled composite material, e.g., Esthet.X HA, that can be targeted for near IR application and heating. In addition, separate from the material(s) forming the composite, the composite/dental material container, or compules, can be designed with specific materials, additives, and/or colors with either low absorption that passes all photon energy to the composite or dental material therein, or high absorption to heat the compule/material container itself. As shown in FIG. 5, different absorption characteristics are obtained for an identical plastic material (polycarbonate) of different colors/opacities. Any of these provided absorbance/overtone bands can be targeted for heating of dental materials and/or dental material containers using photon energy.

Figure 6:
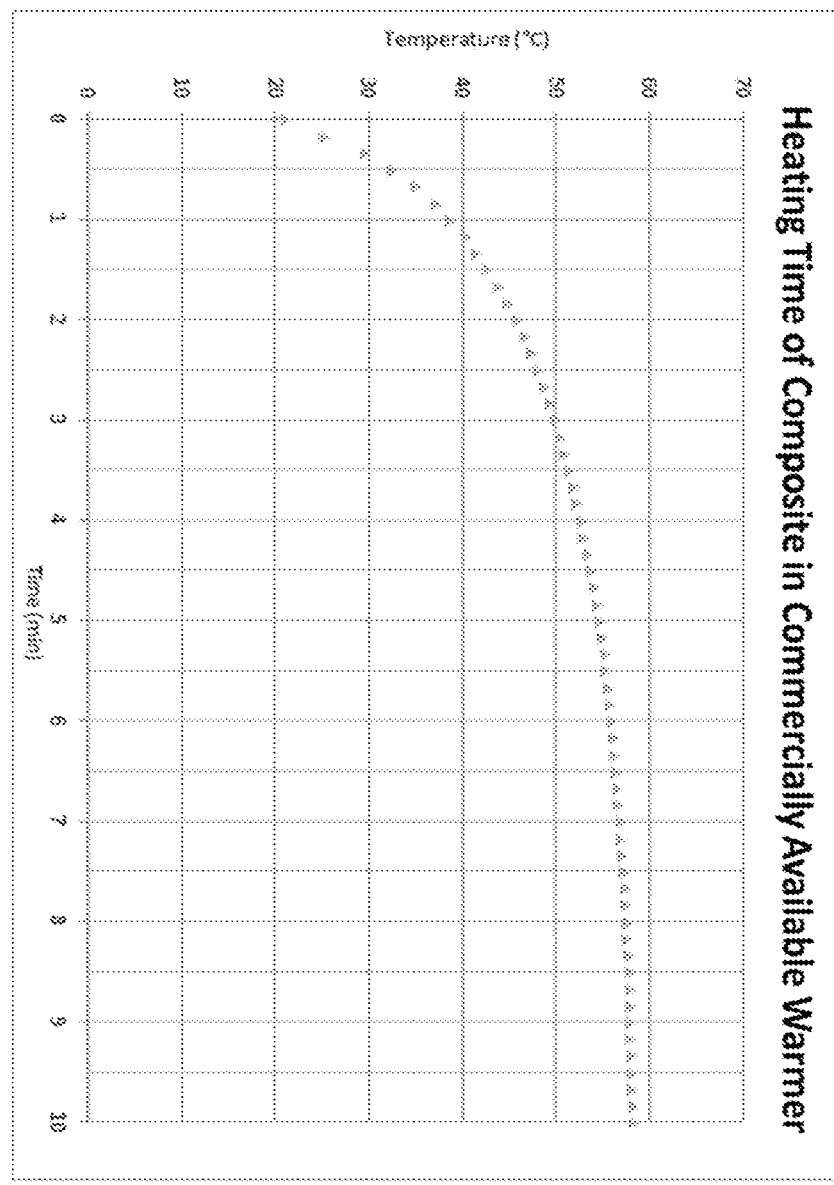
FIG. 6 is a graph of the internal temperature within a composite compule using a commercially available composite warmer. This figure demonstrates how current composite warmers require long warm up times to reach ideal temperatures compared to the invention.
Figure 7:
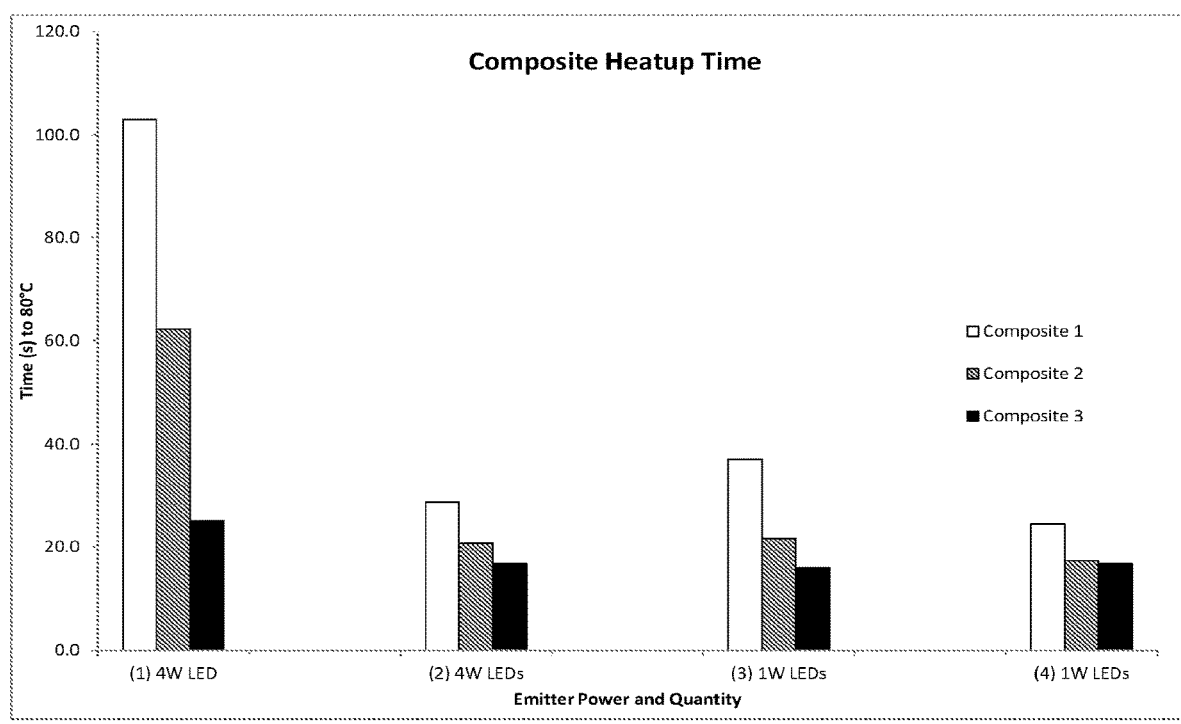
FIG. 7 is a graph of the time to heat three different commercially available dental composites using various photon energy sources and spatial arrangements. This figure demonstrates that optical output power does not necessarily translate solely to heat rates, as thermal diffusion also plays a critical role in the heat distribution and transfer within the composite and composite compule itself. Thus, practicing the invention requires utilizing proper optical power and spatial orientation of photon energy sources directed toward the dental material and/or dental material container for optimal performance and to conserve input power (i.e. efficiency).

Referring now to FIGS. 6 and 7, the ability to target the composite and/or the compule with photon energy also provides a significant decrease in the time required to heat the composite to the desired temperature. In other words, the use of photon energy provides a significant increase in heating rate without any deleterious effects. For comparison, as shown in FIG. 6, heating a composite in a commercially available composite warmer is slow and reaches about 60° C. in 10 minutes. In contrast, as shown in FIG. 7, photon energy can be used to heat the same composite to the same temperature (60° C.) in under 20 seconds, which is highly advantageous to the clinician as this significantly reduces procedural time and increases in-office efficiencies. Different composites (and other dental materials) will heat up faster based on the composition of the composite itself, the composition of the material container, and/or the heat transfer properties of the composite or container. These same concepts hold true for all dental materials. Heating time and rate is also related to the quantity and spatial orientation of the photon energy sources, i.e. a single emitter with 4 W of power will be effective, but will not be as efficient as four emitters with 1 W of power each orientated around the composite container circumferentially. In a preferred embodiment of the invention, a device is created which utilizes between 1 and about 6 light emitting diodes to heat dental materials between about 60° C. and 80° C. in between about 10 seconds and 60 seconds.

Example 2 Determination of Dental Material Viscosity at Elevated Temperature

One additional consideration is the desired target temperature for heating the composite material and/or dental material, as this determines the types and amount of photon energy required to achieve the desired handling and/or performance characteristics. Additionally, for photopolymerizable dental materials, the photon energy must not be in excess, which may prematurely cure the photopolymerizable dental material prior to application. In one exemplary embodiment, the composite can be heated to a temperature between about 50° C. and about 100° C., and more preferably 60° C. and about 80° C.

Figure 8:
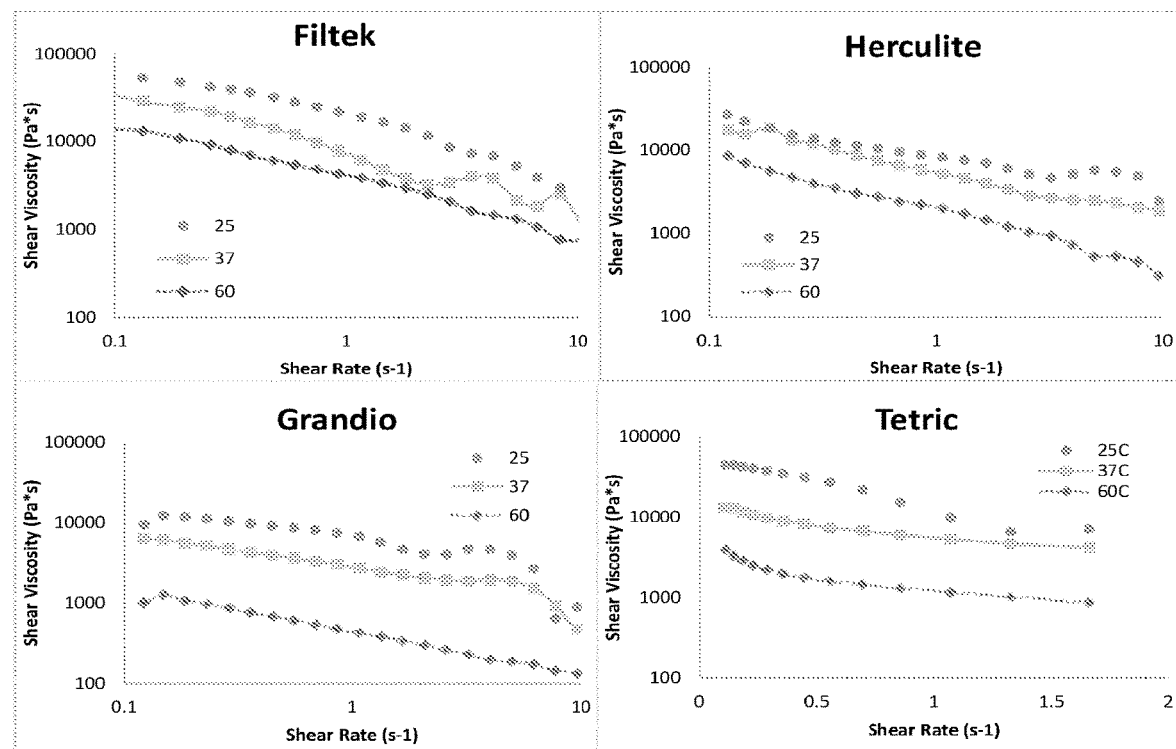
FIG. 8 is a graph of viscosity vs. shear rate for various composites at different temperatures. This figure demonstrates that at all shear rates the viscosity of commercially available dental composites is reduced with increasing temperature, and the reduced viscosity improves the handling characteristics and delivery to the tooth and/or cavity.
Figure 9:
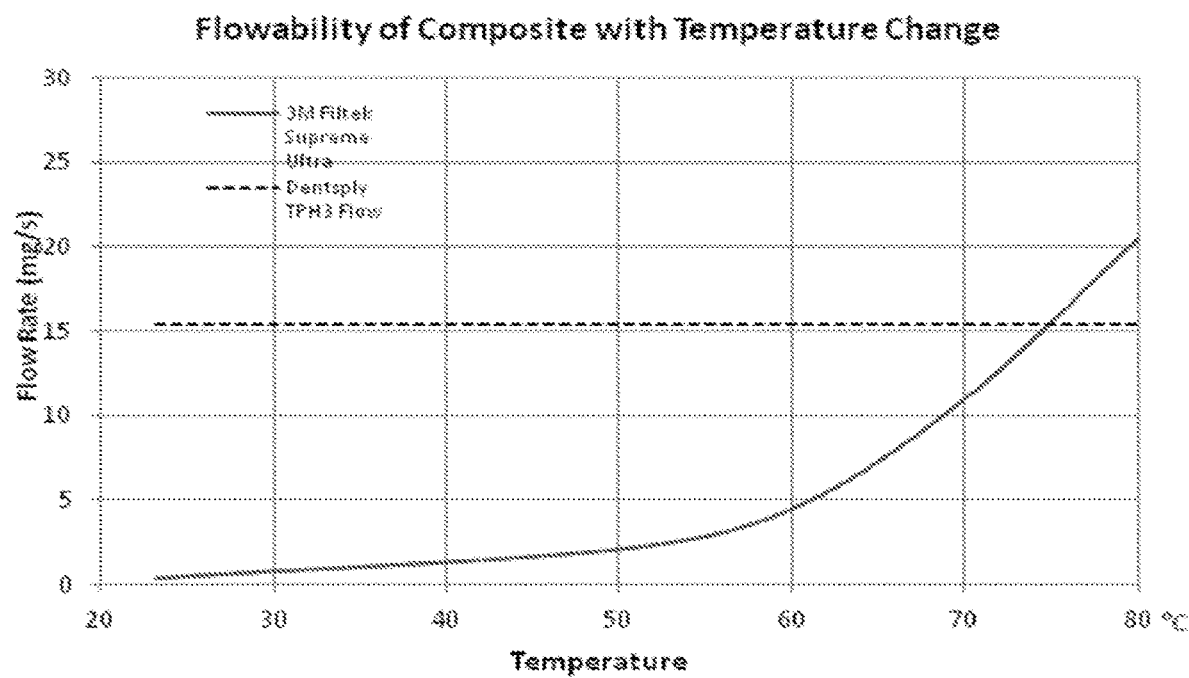
FIG. 9 is a graph of flowability of highly filled composite versus temperature compared to a flowable composite at room temperature. This figure demonstrates that heating of highly filled composites can increase the flowability of highly filled composites to be equivalent or greater to flowable composites, thereby demonstrating that a clinician can use heat to obviate the need of using a flowable composite as a liner in the tooth cavity restoration.

To determine this with more specificity the following evaluation (FIG. 8) was undertaken:
Methods:
The rheological characterization of the four preheated resin based nanocomposite [Herculite Ultra (Kerr, Orange, Calif.), Tetric EvoCeram (Ivoclar Vivadent, Schaan, Liechtenstein), Filtek Supreme Ultra (3M, St. Paul, Minn.) and Grandio (Voco, Cuxhaven, Germany)] were carried out using a shear rheometer with environmental control (Kinexus, Malvern, UK) using a stainless steel parallel-plate geometry setup (diameter of 20 mm). The composite samples (0.2 g) were placed on the rheometer's lower plate, and the upper plate was lowered until it gently touched the surface of the sample at a gap distance of 0.5 mm. The rheometer was set to various temperatures (25° C., 37° C., and 60° C.) and a delay of five minutes was employed prior to measurements to ensure the composite was at the designated temperature. The shear rate was increased linearly in ramp mode from 0.1 to 10 s$^{-1}$.
Results:
The results demonstrate that viscosity decreases by increasing the shear rate. Also, for all shear rates tested, viscosity varies as a function of the heating temperature in the following order: 60° C.<37° C.<25° C.
Conclusion:
Regardless of the resin composite material used, it was found that preheating the dental nanocomposites considerably improves their flowability, which provides increased mechanical bond and seal strength. Thus, increasing the shear rate and temperature resulted in a significant decrease in shear viscosity In addition, similar evaluations were performed on two additional composites as shown in FIG. 8. As a result of these evaluations, it is seen that a benefit of heating highly filled composite is that it will behave like a flowable composite at a certain temperature. This temperature can vary depending on the specific composite brand, however the highly filled composite should be heated above about 60 C to achieve desired flowability. For even higher filled composites, this target temperature is expected to be higher, perhaps about 70° C. or about 80° C. Regardless of the product, photon energy can be used to enhance performance and handling characteristics, such as flowability. Flowability aids in placement in the tooth, and highly filled composite is more durable than flowable composite Example 3. Effects of Temperature on Dental Materials It is in some aspects, it is undesirable to heat the composite to a temperature at which the composite material will cure or harden. For example, at temperatures above 140° C. some dental composite will start to harden (either due to self-curing/polymerizing or evaporation of constituents) making it clinically unusable. This temperature will vary depending on the dental composite's composition, and some composites have maintained integrity at 200° C. This experiment is summarized below.
Methods:
Dental composite from three manufacturers and Gutta Percha from one manufacturer (3 samples of each) were placed on a hot plate and brought up to 60° C. Temperature was monitored with a thermocouple placed in the composite. Temperature was raised by 5° C. every 3 minutes up until 150° C. After 150° C., temperature was raised by 10° C. every 3 minutes. A metal spatula was used to probe the samples and observations were recorded.
Results:
At 60° C., the composite viscosity was greatly reduced for all three brands, supporting previous data. The gutta percha was very soft but still viscous. By 115° C. the gutta percha became similar to the composite at 60° C. and was easy to manipulate with the spatula but had a stringy behavior. At 130° C. the gutta percha's stringiness disappeared and the viscosity was significantly reduced and easily malleable. By 140° C., two of the three composite brands started to harden. When removed from the hot plate, two hardened composites easily crumbled when manipulated with little pressure. The third brand of composite did not harden or crumble up to 200° C. It did not seem to be affected, and was still able to be cured at this temperature. The gutta percha seemed unaffected up to 200° C. Between 200° C. and 250° C. it started to create a visible and odorous fume, but did not discolor or noticeably change its material properties.

Conclusion:

Composite should be kept to temperatures below 140° C. to avoid compromising performance, higher than 100° C. should not be clinically required since the desired flowability is already reached at temperatures <100° C. Gutta percha should not be heated above 200° C.; desired flowability is also reached below this temperature at about 115° C. to about 200° C. These temperature boundaries are considered in this invention. In some aspects, the use of photon energy does not increase the temperature of dental materials greater than about 200° C. In some aspects, the use of photon energy does not increase the temperature of dental materials greater than about 140° C.

In a different benchtop test (data not provided), a heat block and oven were brought to elevated temperatures of 120° C. and 150 degrees Celsius to determine if primarily conductive heating from a very hot element can reduce the warm up time of a dental composite and compule. The composite reached 80° C. in over 30 seconds, but quickly continued to elevate in temperature >100° C. and hardened, rendering the material unusable. This data supports that conductive heating, similar to commercially available composite warming units, is unable to quickly warm the composite in a safe and controlled manner without deleterious effects on the composite.

Dental irrigants, such as ones containing sodium hypochlorite, have enhanced performance at elevated temperatures (up to 60° C.) but also degrade quicker at higher temperatures and should not be heated above boiling (100° C.). Therefore, in one embodiment photon energy is used to heat dental liquids/irrigants between about 30° C. and about 100° C.

In summary, the particular temperature to which a particular dental material should be heated for enhancement without negative effects depends greatly upon the composition of the dental material.

Figure 13:
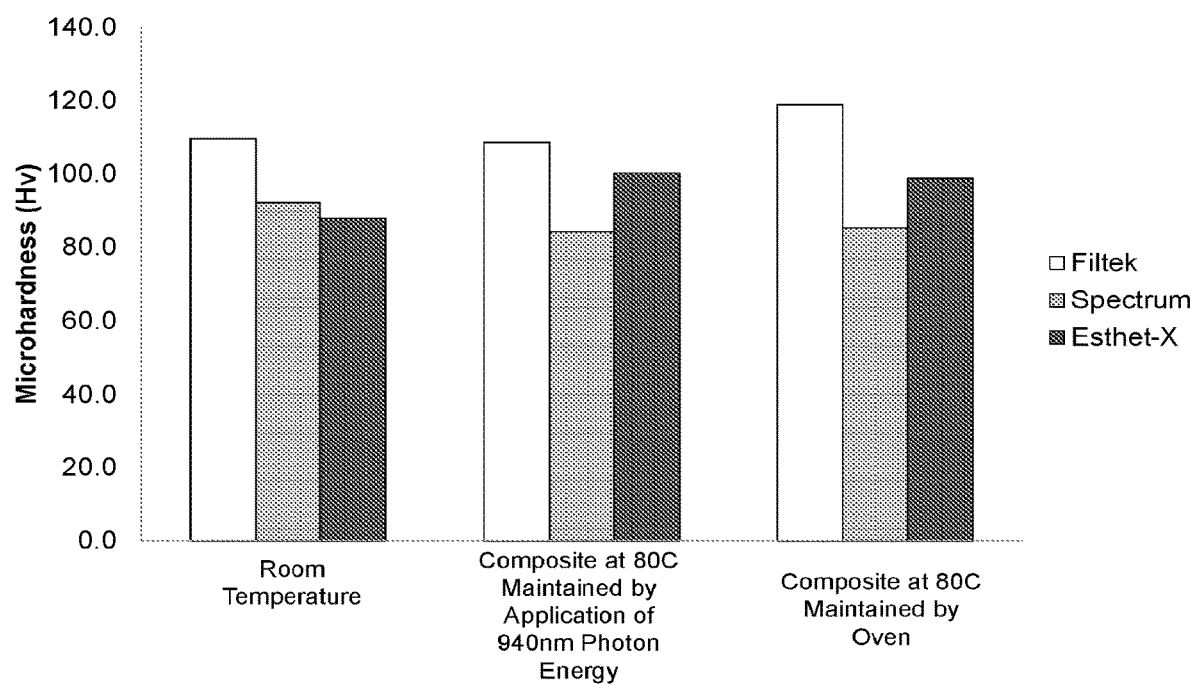
FIG. 13 is a graph of post-cure microhardness values of various commercially available dental composites after the application of extended elevated temperatures from either photon energy or an oven compared to room temperature. Data demonstrates that 1 hour applications of elevated temperatures (80° C.) resulting from photon energy, or an oven, did not negatively impact the composite as microhardness values were not statistically significantly different compared to room temperature (untreated) composite post-cure.

FIG. 13 provides a summary of data collected to test for negative effects of extended periods of elevated temperature and near infrared (NIR) photon energy exposure on curing properties of dental composites.

Methods:

Three different commercially available composite brands were tested in each of three conditions: room temperature at 20° C. (control), 80° C. in an oven, and 80° C. via photon energy. For the elevated temperature group, an oven was brought to 80° C. and the composites were placed within for 1 hour. For NIR exposure, NIR LEDs (940 nm) were used along with a thermocouple and microcontroller. The LEDs were turned on at 100% with the thermocouple inserted into the composite for feedback to bring the composite temperature up to 80° C., which took under 1 minute. At this point, the microcontroller switched to pulse with modulation to maintain the constant temperature for 1 hour. Composite was dispensed and formed into a puck using a 2 mm puck mold (Paradigm Curing Discs, 3M Company SKU: 76965) and cured for 20 seconds using a commercially available curing light. In the elevated temperature groups, dispensing was done immediately after removing from the oven or NIR LED fixture.

Results:

As evident from the data, prolonged exposure to elevated temperatures from a convection oven or by absorbed near infrared photon energy did not statistically impact post cure microhardness values as compared to room temperature stored dental composite. Furthermore, there was no change in the observed aesthetics of the dental composites tested.

Conclusion:

Maintaining composite at 80° C. using photon energy did not deleteriously impact the material.

Example 4. Absorption Measuring Experiment Using a Proximity Sensor

Figure 20:
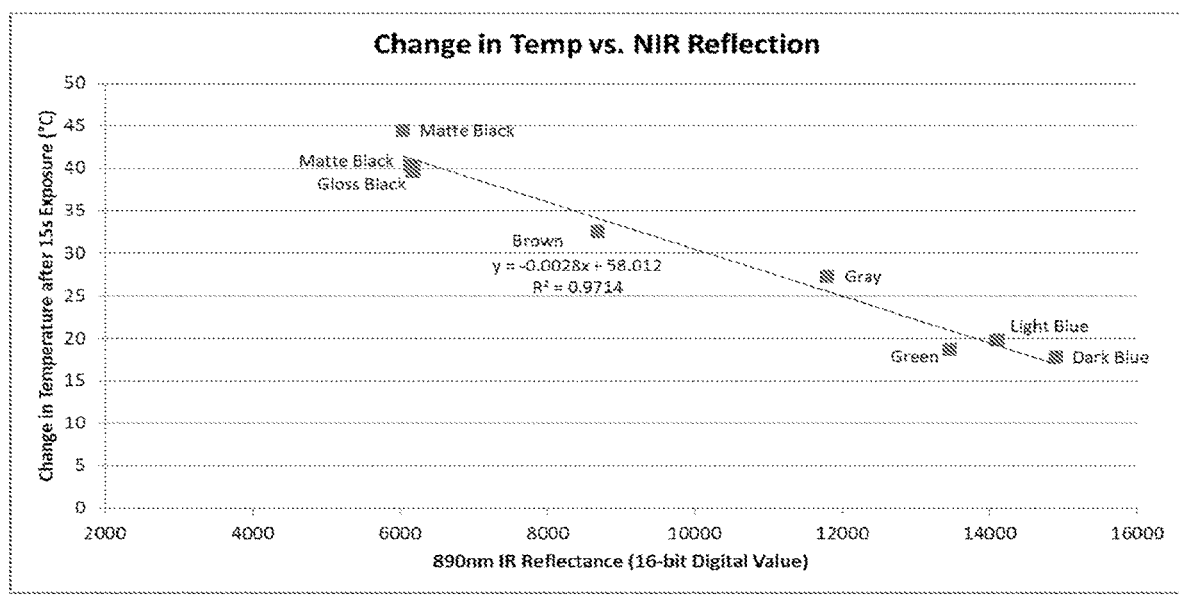
FIG. 20 is a graph showing the NIR reflection values compared to the internal temperature of a dental material exposed to 15s of photon energy within the specified photon energy band from a Vishay VCNL4010 sensor (Fully Integrated Proximity and Ambient Light Sensor with Infrared Emitter, I²C Interface, and Interrupt Function) obtained from various colored commercially available dental containers. This figure demonstrates that at a fixed distance from the sensor, there is a strong correlation ($R^2=0.97$) between the measured NIR reflectance and the object's change in temperature after 15 seconds of exposure to an NIR LED (wavelength, power, time, and distance were all held constant between objects). The sensor, therefore, can be used to determine the amount of photon energy needed to heat a given dental material, or a material's container, to a desired temperature and optionally maintain the desired temperature over a period of time. Additionally, the sensor's measured value can be a "fingerprint" to identify the inserted object to implement a closed platform system (i.e. the device would only work with a specific material or material container).

A test was performed using a proximity sensor (Vishay VCNL4010 sensor—Fully Integrated Proximity and Ambient Light Sensor with Infrared Emitter, I$^2$C Interface, and Interrupt Function) that incorporates both an infrared (IR) LED at 890 nm and an IR phototransistor to measure reflected IR photon energy. Typically this sensor is used to measure the distance of an object, however the results of our test shown in FIG. 20 shows that at a fixed distance from the sensor, there is a strong correlation ($R^2$=0.97) between the measured IR reflectance and the object's change in temperature after 15 seconds of exposure to an IR LED (wavelength, power, time, and distance were all held constant between objects). Objects tested were all commercially available dental composite compules of different colors. Therefore, the sensor can be used to determine the amount of photon energy needed to heat a given dental material, or a material's container, to a desired temperature and optionally maintain the desired temperature over a period of time. Additionally, the sensor's measured value can serve as a "fingerprint" to identify the inserted object to implement a closed platform system (i.e. the device would only work with a specific material or material container).

Example 5. Dental Composite Microhardness Vs Temperature

In addition to an enhancement of the flowability of the composite, the heating of the composite has been determined to result in enhancements with respect to the hardness or durability of the composite material when cured after application. To illustrate this, the following evaluations were conducted, with the results graphically illustrated in FIG. 10.

Methods:

A custom heating setup was used to heat a 2 mm×3 mm composite puck (height×diameter) to designated temperatures (25, 40, 60, and 80° C.). Composite pucks were cured (Paradigm Curing Light, 3M, St. Paul, Minn.) at the various temperatures and kept in a dark container at 37 C for 24 hours. Microhardness was measured on the sample's top and bottom surfaces using a HMV-G Micro Hardness Tester (Shimadzu, Kyoto, Japan) under the following experimental conditions: Force setting—HVO.2 (1.961N); Hold time—10 seconds. Prior to microhardness measurements, the composite samples were smoothened using 180, 500 and 1500 grit sandpaper to level the sample and polish the sample's surface for analysis. Four resin based nanocomposite were tested (n=9 for each): Herculite Ultra (Kerr), Tetric Evo-Ceram (Ivoclar Vivadent), Filtek Supreme Ultra (3M) and Grandio (Voco). Unpaired student's t-tests (a=0.05) were used to compare statistical significance between temperature results.

Figure 10:
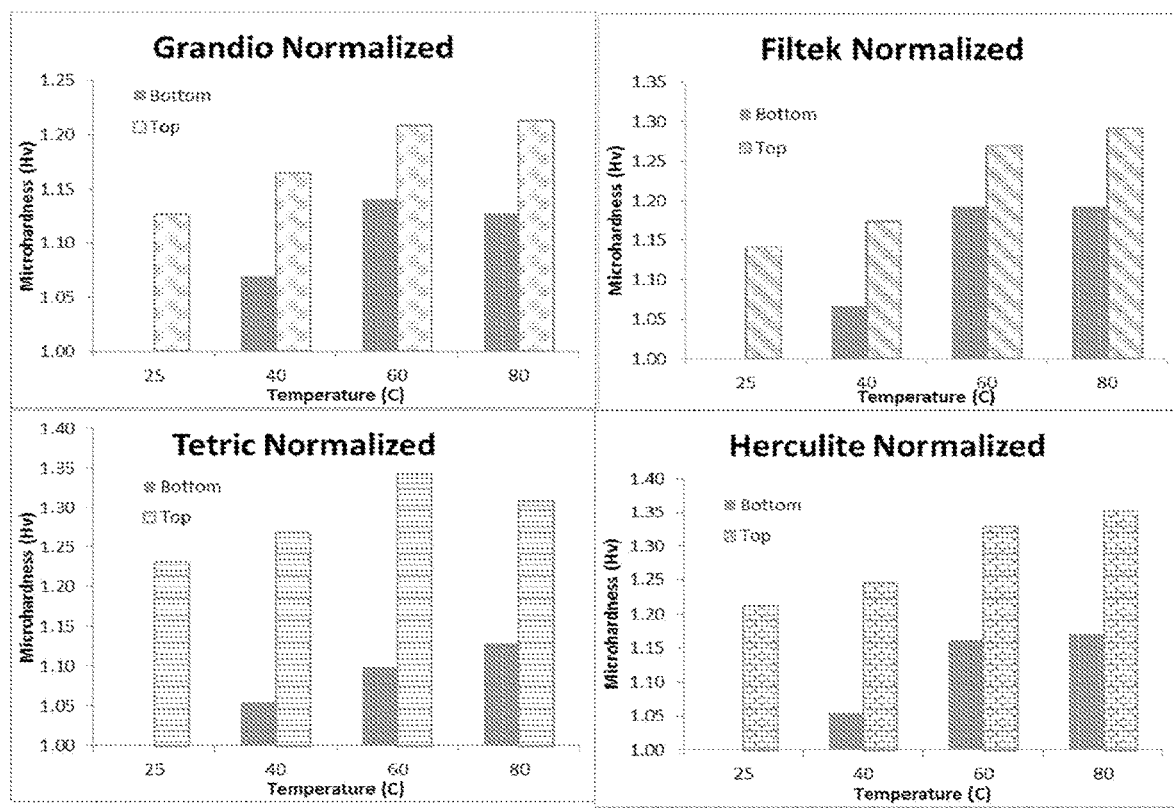
FIG. 10 is a graph of post-cure microhardness when various commercially available dental composites are maintained and cured at various temperatures. This figure demonstrates that elevated temperatures above ambient increases the polymerization of dental composites during curing resulting in higher microhardness on the top and bottom of a 2 mm puck.

Results:

Microhardness results are summarized in the subsequent FIG. 10. Pre-heating the Grandio and Filtek composites ≥60° C. resulted in statistically significantly increased microhardness on both the top and bottom surfaces of the samples (p<0.02). Pre-heating the Tetric composite to 60° C. resulted in statistically significantly increased microhardness on the top surface of the samples (p=0.047). Pre-heating the Herculite composite to 80° C. resulted in statistically significantly increased microhardness on the top surface of the samples (p<0.05).

Conclusion:

Curing dental composites at elevated temperatures is favorable to increase composite microhardness. In particular, 60° C. C–80° C. is the target range to increase microhardness for the composites tested. Therefore, additives that act to increase the photopolymerizable dental material's temperature prior to or during curing can act as a polymerization enhancer themselves, since increased temperature leads to increased polymerization and a higher microhardness measurement. Thus, in some aspects photon energy is used to heat dental materials, specifically dental photopolymerizable materials, to temperatures between about 60° C. and about 80° C.

Example 6. Dental Composite Degree of Conversion Vs Temperature

Figure 11:
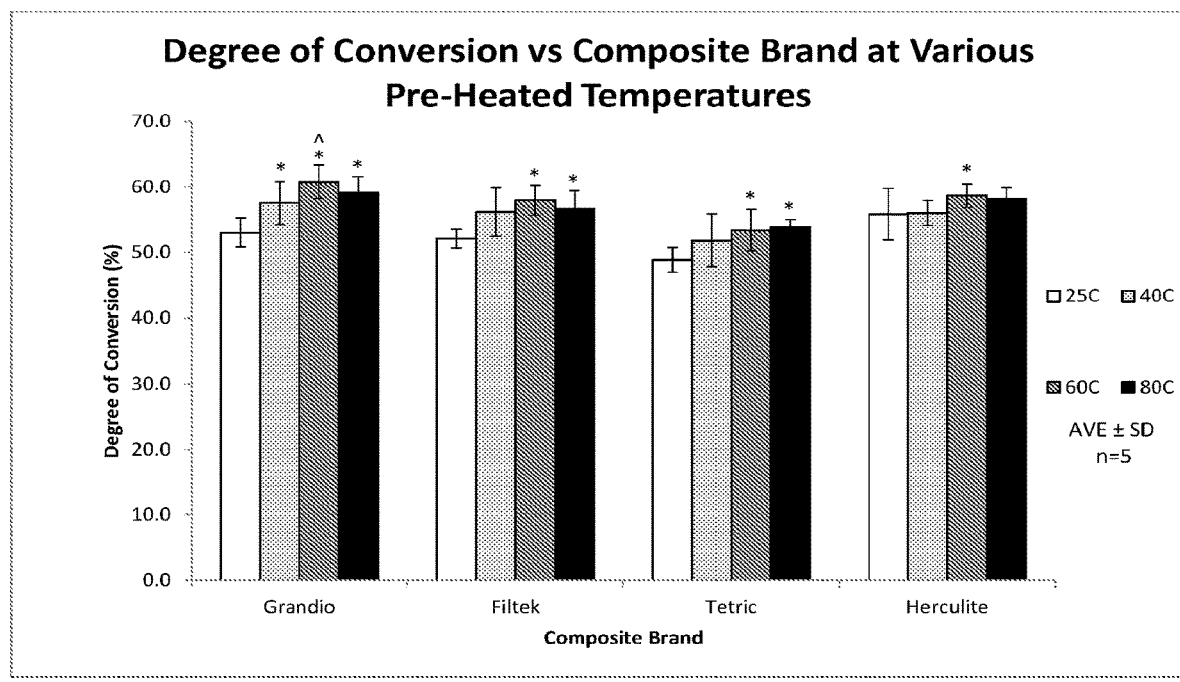
FIG. 11 is a graph of post-cure monomer and oligomer conversion when various commercially available dental composites are maintained and cured at various temperatures. This figure demonstrates that elevated temperatures above ambient increases the degree-of-conversion of monomers to oligomers and polymers within dental composites during curing, which results in higher microhardness on the top and bottom of a 2 mm puck.

As another measure of the enhancement of durability as a result of the heating or pre-heating of the composite prior to application and curing of the dental composite, the degree of conversion of the composite material at elevated temperatures was also assessed according to the following evaluation, the results of which are shown in FIG. 11.

Methods:

A custom heating setup was used to heat a 2 mm×3 mm composite puck (height×diameter) to designated temperatures (25° C., 40° C., 60° C., and 80° C.).

Composite pucks were cured at the various temperatures and kept in a dark container at 37° C. for 24 hours. The DoC was measured at the top surface of the sample by micro-attenuated total reflectance fourier transform infrared spectroscopy (micro-ATR FTIR) using a Nicolet iS5 Spectrometer equipped with an iD5 ATR accessory (ThermoFisher Scientific, Waltham, Mass.) at the following specifications: wave number range=4000-650 cm-1, 32 scans/second, and 2 cm-1 resolution. Four resin based nanocomposite were tested (n=5 for each): Herculite Ultra (Kerr), Tetric Evo-Ceram (Ivoclar Vivadent), Filtek Supreme Ultra (3M) and Grandio (Voco). Unpaired student's t-tests (a=0.05) were used to compare statistical significance between temperature results.

Results:

Degree of conversion results are shown in FIG. 11. All four composite brands showed statistically significantly increased degree of conversion (DoC) for composites heated to 60° C. compared to 25° C. (p<0.05). All composite brands, but Herculite (p=0.11), showed statistically significantly increased DoC for composites heated to 80° C. compared to 25° C. (p<0.03). Only Grandio showed statistically significantly increased DoC when heated to 40° C. compared to 25° C. (p=0.02)

Conclusion:

Curing of dental composites at elevated temperatures results in higher DoC. In particular, 60° C.–80° C. is the target range to maximize DoC. Thus, in some aspects photon energy is used to heat dental materials, specifically dental photopolymerizable materials, to temperatures between about 60° C. and about 80° C.

Example 7. Polywave/Multi-Spectral Curing

As pre-heating of the photopolymerizable dental material provides enhancement to the photopolymerizable dental material upon curing, the benefits of combined blue light at 440-500 nm and a second wavelength above 520 nm was evaluated. The impact of combined photon energy and curing light emissions on composite microhardness was investigated according to the following experiment, the results of which are graphically illustrated in FIG. 12:

Methods:

A custom setup was used to investigate the simultaneous near-infrared photon energy and curing of Filtek Supreme composite. Briefly, the setup consisted of a 2 mm puck mold (Paradigm Curing Discs, 3M Company SKU: 76965) placed above a fixed near-infrared LED die package (5 mm away; 4 die 850 nm LED, LEDEngin, San Jose, Calif., operated at 1 A) and below a fixed dental curing light (2 mm away; Valiant Curing Light, Vista Dental Products, Racine, Wis.). Five different groups were tested with an n=3 for each group: G1) Valiant's standard 20 s cure mode (no NIR), G2) Valiant's boost 3 s cure mode (no NIR), G3) Valiant's standard 20 s cure+20 s NIR (0 s lag; i.e. simultaneous), G4) NIR (0-25 seconds)+Valiant's standard 20 s cure (from 5-25 s), i.e. a 5 s NIR lead, and G5) NIR (0-13 s)+Valiant's boost 3 s cure (10-13 s), i.e. a 10 s NIR lead. Composite samples were subjected to microhardness evaluation as described in example 5. Unpaired student's t-tests (a=0.05) were used to compare statistical significance between experimental groups.

Figure 12:
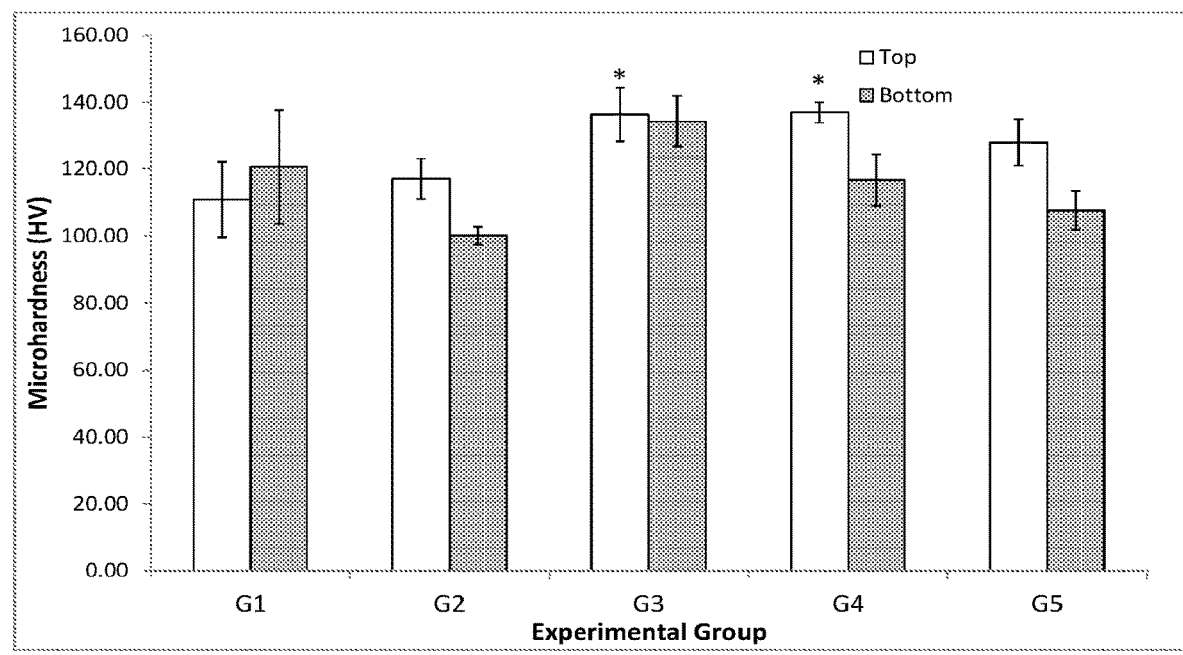
FIG. 12 is a graph of microhardness values post-cure of highly filled composites subjected to various multispectral patterns of applied photon energy (850 nm) and curing light (405 nm and 470 nm simultaneously). A statistically significant difference ($p<0.05$) was observed between G3 top vs G1 top, and G4 top vs G1 top. This figure demonstrates that the addition of photon energy within the disclosed wavelength range enhances the polymerization and degree-of-conversion translating to increased microhardness values post-cure.

Results:

Composite hardness results are provided in the subsequent FIG. 12. G3 and G4 showed statistically significantly increased microhardness on the top side of the composite samples compared to G1 (p=0.03 and 0.02, respectively). Statistical significance was not observed comparing the results between G2 and G5 (p=0.11); however, inter-group comparison reveals that G5's results had higher average results for both sides of the sample. Thus, a larger sample set may help elucidate the true trend between these groups.

Conclusion:

The simultaneous or sequential use of wavelengths above 520 nm and curing light seems to improve cured composite microhardness as this method does not negatively affect the curing process.

Figure 21:
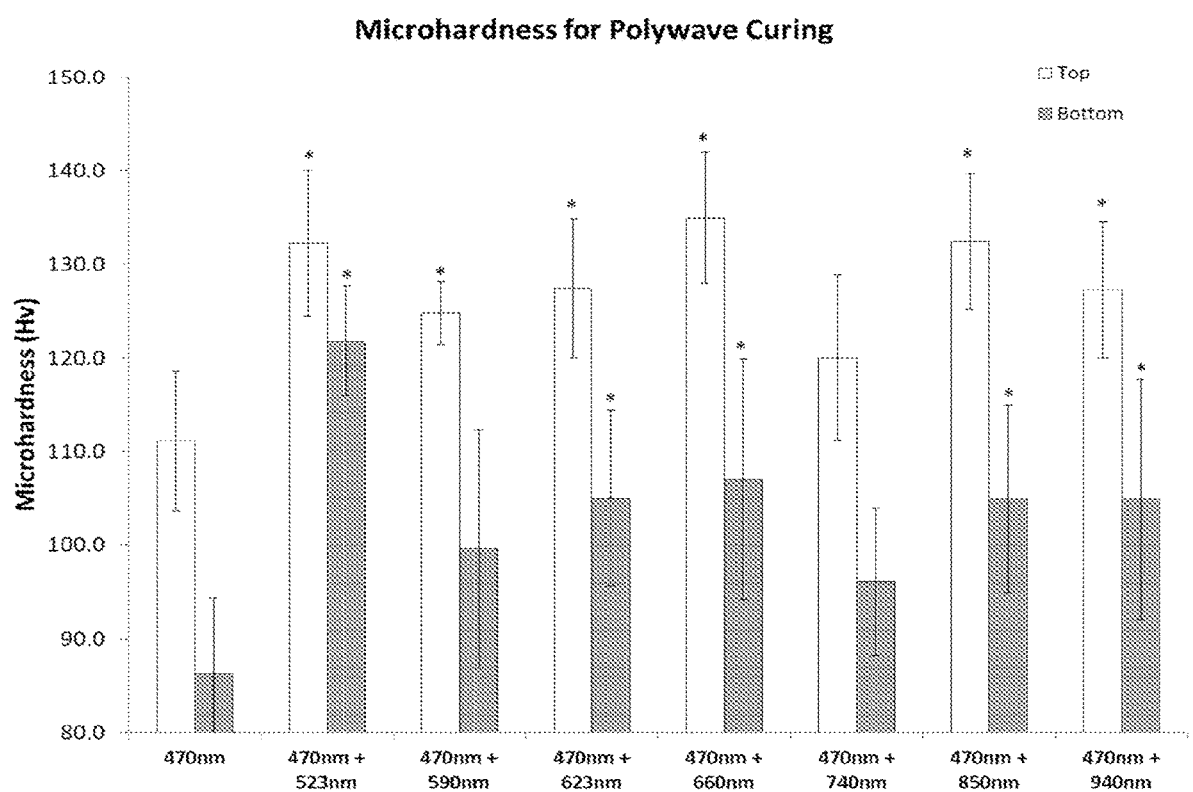
FIG. 21 is a graph showing the post-cure microhardness values of filtek supreme composite when subjected to multispectral light by simultaneously applying photon energy within the disclosed wavelength band and 470 nm light for curing. The asterisk designates statistically significantly different values compared to the "470 nm" group. This figure demonstrates that the addition of photon energy within the disclosed wavelength range enhances the polymerization and degree-of-conversion translating to increased microhardness values post-cure.

In addition, the impact of other wavelengths within the specified wavelength range (520 nm-2500 nm) on composite microhardness were evaluated according to the following experimentation, the results of which are graphically illustrated in FIG. 21

Methods:

A custom setup was used to investigate the simultaneous application of photon energy at various wavelengths and curing of Grandio SO composite. The setup consisted of a ring of 3 blue LEDs (475 nm Cree XLamp XP-E2) 5 mm away from the sample with a fourth interchangeable LED in the center. The power of the blue LEDs were adjusted so that the composite sample would be exposed to the same optical energy level as used with a commercially available curing light (Valiant Curing Light, Vista Dental Products, Racine, Wis.). The interchangeable LEDs were adjusted so they all emitted the same optical power output, while the optical power from the 3 blue LEDs was kept consistent. Optical power measurements were performed using an optical power meter (S310C sensor, PM100D console, Thor Labs, Newton, N.J.). Wavelengths tested by the interchangeable LED were 523 nm, 590 nm, 623 nm, 660 nm, 740 nm, 850 nm, and 940 nm (LedEngin LZ1). Ten seconds of exposure of the interchangeable LED preceded 20 seconds of combined interchangeable LED and blue LED output. In other words, the interchangeable LED emitted light for 30 seconds, while the three blue LEDs emitted light during the last 20 seconds, i.e. the photon energy within the specified wavelength leads the polymerization light by 10 s. Composite samples were subjected to microhardness evaluation as described previously in "Composite Microhardness vs Temperature" section. Unpaired student's t-tests (a=0.05) were used to compare statistical significance between experimental groups.

Results:

Microhardness data for the tested wavelengths are shown in FIG. 21. Top hardness was significantly greater using 523 nm, 590 nm, 623 nm, 660 nm, 850 nm, and 940 nm. Bottom microhardness was significantly greater using 523 nm, 623 nm, 660 nm, 850 nm, and 940 nm.

Figure 22:
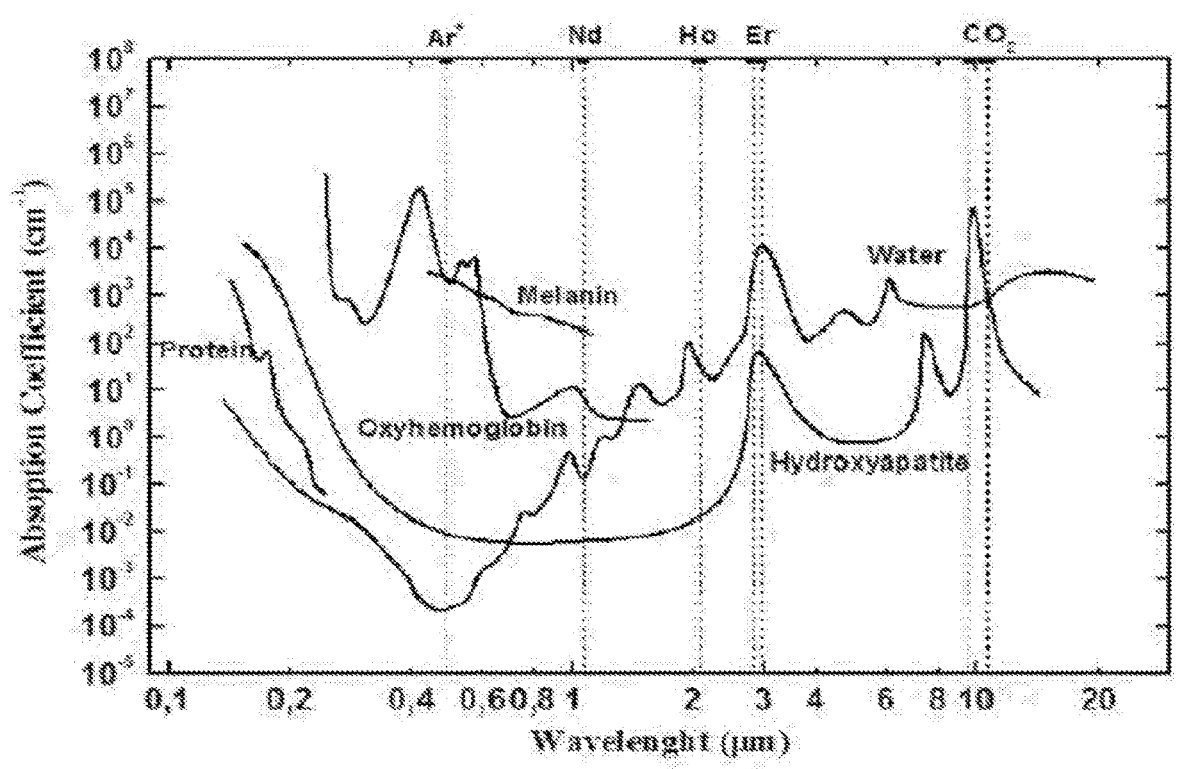
FIG. 22 is a graph showing the absorption coefficient for biological tissues at various wavelengths, of particular importance to teeth are oxyhemoglobin, protein, water, and hydroxyapatite. Although hydroxyapatite and water exhibit low absorption coefficients for commercially available curing light spectra, i.e. peak emission at 470 nm, oxyhemoglobin absorption coefficient is 1000-10000 times higher absorbance than the disclosed photon energy spectra, and is why commercially available curing lights pose concern for intrapulpal temperature rises and safety. The disclosed invention, therefore, can utilize photon energy between 520 nm and 2500 nm to increase composite microhardness (FIG. 21), decrease oxyhemoglobin and pulp absorbance, and improve clinical efficacy and safety.

Conclusion:

Multiple wavelengths showed improved post-cure microhardness on the top and bottom of the puck when combined with the standard blue polymerization light at 470 nm. These wavelengths would be advantageous to use clinically, as harder composites illustrate decreased wear in increased longevity. Furthermore, although hydroxyapatite and water exhibit low absorption coefficients for commercially available curing light spectra, i.e. peak emission at 470 nm, oxyhemoglobin absorption coefficient is 1000-10000 times higher absorbance than the disclosed photon energy spectra (ref FIG. 22); this is why commercially available curing lights pose concern for intrapulpal temperature rises and safety. Therefore, the disclosed invention can utilize photon energy between 520 nm and 2500 nm to increase composite microhardness (FIG. 21), decrease oxyhemoglobin and pulp absorbance, and improve clinical efficacy and safety.

Furthermore, the described "lead" of the photon energy emission, prior to curing light emission, demonstrates a successful exemplary embodiment of the invention. No deleterious effects were observed by using two discrete emission spectra during testing, wherein one emission spectra is within the disclosed photon energy range (520 nm-2500 nm).

Example 8. Improved Heating by Incorporating a Heating Additive to Dental Composite or Gutta Percha To enhance the absorption of the dental material in the near IR wavelengths, and thus improve the conversion of applied photon energy to temperature rise of dental material, near IR dyes (i.e., a photon energy absorption enhancer) were added. The first evaluation saw using two different NIR dyes as an additive to gutta-percha and a composite and the heating was evaluated according to the following experiment:

Methods:

Two near-infrared dyes were investigated (Nickel(II) 5,9,14,18,23,27,32,36-octabutoxy-2,3-naphthalocyanine, Sigma Aldrich, Milwaukee, Wis.; and QCR #NIR848A (QCR Solutions, Port St. Lucie, Fla.). Dyes were dissolved in ~0.3 mL chloroform (Sigma Aldrich, Milwaukee, Wis.) at varying concentrations to yield 2 w/w %, or 5 w/w % dye in gutta percha or 1 w/w %, or 2.5 w/w % dye in dental composite (Filtek Supreme). Once the dye was dissolved, powderized gutta percha or dental composite was added to the mixture and hand-blended with an additional ~0.5 mL chloroform until smooth. The newly formed gutta percha/composite then sat in a fume hood for ~30 minutes to allow the chloroform to evaporate. Gutta percha samples were placed on a watch glass on a 120° C. hot plate for 5 minutes until soft. Gutta percha pucks were made using a custom 2 mm height×3.4 mm diameter mold. A thermistor was placed into the gutta percha pucks and the samples were heated using an 850 nm four die LED package at a distance of 3 mm. Composite samples were formed in a similar fashion, except heat was not needed to create the pucks.

Results:

Heating results are provided in tables 15-16 below. Table 15 shows the results following addition of Near IR Dye #1 to Gutta-Percha. The Near IR dye #1 was Nickel(II) 5,9,14,18,23,27,32,36-octabutoxy-2,3-naphthalocyanine having an Absorbance of 845-851 nm and an extinction coefficient of 111 L/g*cm. The test compositions included either 2% or 5% of Dye 1 in powder Gutta Percha.

TABLE 15

Near IR Ni Dye in Gutta-Percha

| Sample | To (° C.) | Tf (30 s) (° C.) | Delta T (° C.) |
|---|---|---|---|
| 2% Dye 1 | 28 | 72 | 44 |
| 5% Dye 1 | 25 | 126 | 101 |
| GP (no dye) | No measurable temperature difference | | |

Table 16 shows the results following addition of Near IR Dye #2 to Gutta-Percha. Table 17 shows the results following addition of various concentrations of Near IR Dye #2 to the commercially available dental composite Filtek. The Near IR Dye #2 was QCR #NIR848A (Lot #0519-16A-8484) having an extinction coefficient of 330 L/g*cm. The test compositions included either 2% or 5% Ni IR dye in powder Gutta Percha

TABLE 16

Near IR QCR Dye in Gutta-Percha

| Gutta Percha | To (° C.) | Tf (30 s) (° C.) | Delta T (° C.) | Time to 80° C. |
|---|---|---|---|---|
| GP + 2% Dye 2 | 25 | 96 | 71 | 24 s |
| GP + 5% Dye 2 | 25 | 171 | 146 | 9 s |

TABLE 17

Near IR QCR Dye in Filtek Dental Composite

| Filtek Composite | To (° C.) | Tf (30 s) (° C.) | Delta T (° C.) | Time to 80° C. |
|---|---|---|---|---|
| Filtek without dye 2 | 24 | 105 | 81 | 18 (trial 1) 22 (trial 2) |
| Filtek + 1% Dye 2 | 26 | 178 | 152 | 7 s |
| Filtek + 2.5% Dye 2 | 26 | N/A | N/A | 9 s |
| Filtek + 5 ppm Dye 2 | 24 | 100 | 76 | 20 |
| Filtek + 10 ppm Dye 2 | 23 | 132 | 109 | 12 (trial 1) 12 (trial 2) |
| Filtek + 100 ppm Dye 2 | 23 | 117 | 94 | 14 |

Conclusion:

The addition of Near IR dyes significantly improves the efficiency of the deposited NIR photon energy to a temperature rise in the dental material and quickens the heating of dental materials, such as composite and gutta-percha. In one embodiment, an additive is added to a dental material composition in the concentration of at least 10 ppm (0.001%) that absorbs photon energy between 520 nm-2500 nm to facilitate rapid heating of the dental material. Additionally, this additive can be added to the dental material container.

Another test examined adding a NIR dye to composite. The heating rate/characteristics were evaluated according to the following experiment, the results of which are shown graphically in FIG. 23:

Methods:

One near infrared dye was investigated (LUNIR1). The dye was weighed and placed in a cuvette. Dental Composite (Grandio SO, VOCO GmBH) was added in the correct amounts to create 0.1 mg of composite with a dye concentration of 0.10%, 0.50%, 1.0%, and 2.0% by weight. These were tested against a control of dental material only. The composite was then exposed to a near infrared LED (940 nm LedEngin LZ1) for 15 seconds. Starting and ending temperature of the composite was measured using a thermocouple placed in the composite. Unpaired student's t-tests (a=0.05) were used to compare statistical significance between experimental groups.

Figure 23:
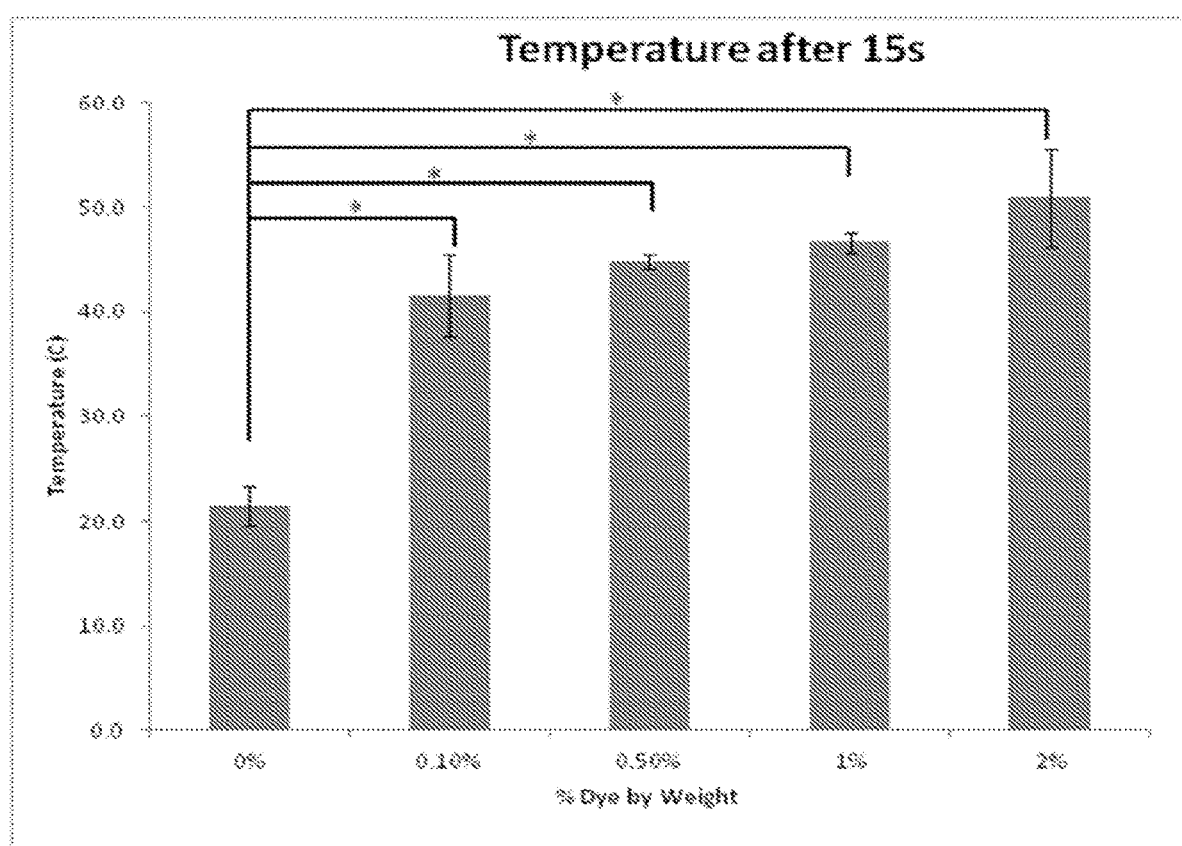
FIG. 23 is a graph showing the increase in dental composite (Grandio SO, VOCO) temperature when a photon energy absorber/dye was added at varying concentrations. Statistically significantly improved heating was observed with concentrations 0.1% of the LUNIR1 dye. The figure demonstrates that adding a photon energy absorbing dye to the composite significantly improves the energy conversion efficiency of photon energy to heat as evident by a substantially increased temperature observed after exposure to about 15 seconds of photon energy.

Results:

Composite temperature change data for the tested dye concentrations are show in FIG. 23. Statistically significant differences were found between the control and each of the four dye concentrations. No statistical significance was found when comparing the temperatures between the different dye concentration percentages. Regardless of LUNIR1 concentration, the composite's color did not noticeably change from the original tooth resin shade.

Conclusion:

Adding a photon energy absorbing dye to the composite significantly improves the efficiency of the deposited photon energy to be converted into heat and a temperature rise in the dental material. There is an observed positive trend of increased temperature rise with greater dye concentrations though no statistical difference. Thus, in one embodiment an additive is added to a dental material composition in the concentration of at least 0.1% that absorbs photon energy between 520 nm-2500 nm to facilitate rapid heating of the dental material. Additionally, the additive should not introduce an unnatural tooth color change to the dental material.

Another test examined adding a different dye to composite. The absorbance characteristics of the composite blend was evaluated according to the following experiment, the results of which are shown graphically in FIG. 24.

Methods:

Indocyanine green (ICG) is a well-known biocompatible dye that is FDA approved for in vivo use and has a peak absorbance at 800 nm. ICG was dissolved in ~0.3 mL chloroform (Sigma Aldrich, Milwaukee, Wis.) and added at varying amounts to yield 1 ppm, 10 ppm, 100 ppm, and 1000 ppm dye in dental composite (Filtek Supreme, shade A2). The mixture was then hand-blended until smooth and sat in a light-protected fume hood for ~10 minutes to allow the chloroform to evaporate (light protection was required to ensure the composite wasn't cured by room light). The samples were then subjected to Fourier transform spectroscopy to measure the absorbance at 800 nm.

Results:

As FIG. 24 illustrates, 10 ppm ICG resulted in a significant increase in absorbance of the dental composite at 800 nm. Further increases in ICG concentration resulted in increased absorbance. The absorbance of 1 ppm ICG was nearly identical to 0 ppm ICG. ICG concentrations of 1 ppm and 10 ppm did not noticeably change the composite color from the original composite tooth shade. However, 100 ppm and 1000 ppm ICG resulted in a green composite blend/mixture, which constitutes and unnatural tooth color.

Conclusions:

The addition of a photon energy absorbing dye, ICG, at concentrations greater than 1 ppm resulted in significantly increased material absorption at 800 nm. 10 ppm ICG would be applicable for dental composites, as the addition of 10 ppm ICG did not noticeably change the composite color from the original composite tooth shade. Due to aesthetic concerns, 100 ppm and 1000 ppm would not be applicable for use in dental composite. However, 100 ppm and 1000 ppm can be used in non-aesthetic procedures or in dental materials that are not concerns with aesthetics (e.g. gutta percha that is filled inside the tooth and not cosmetically visualized).

Example 9. Far Red or Near IR Dye Additive+Composite as a Photoinitiator to Improve Curing A far red dye that is a combination of a photo initiator and co-initiator to dental composite and the properties of the cure were evaluated according to the following, the results of which are shown in FIG. 26.

Methods:

Dental composite (Ivoclar Evo-Ceram) was used with a far red light photoinitiator (H-Nu 660, Spectra Group Limited) at varying concentrations from 0.005% to 0.1% by weight along with a co-initiator (Borate V) used at 10× times concentration. Also tested for comparison were unmodified composite and composite with the co-initiator at 1% by weight without the initiator. Pucks of composite were made 2.35 mm deep and 3.45 mm wide. Curing was performed on all variables with a far red (660 nm LedEngin LZ1) and blue (475 nm Cree XLamp XP-E2) LED combination. The red LED was first activated for 10 seconds, followed by 20 seconds of simultaneous red and blue LED activation. Also tested as a control was an additional blue LED in place of the red on the unmodified composite and composite only with the coinitiator. Surface microhardness was measured on the top and bottom of the composite puck after curing. Unpaired student's t-tests (a=0.05) were used to compare statistical significance between experimental groups.

Results:

Microhardness data for the tested conditions are shown in FIG. 26. A significant increase was found on the top for 0.005% 660 nm initiator+0.05% Borate V. Significantly lower hardness was found for 0.1% 660 nm initiator+1.0% Borate V, 0.05% 660 nm initiator+0.5% Borate V, and 0% 660 nm initiator+1.0% Borate V. Additionally, a visible color change from green/blue to standard A2 shade was visualized after photopolymerization for the various compositions, as shown in FIG. 27. In particular, the green/blue color was unnoticeable post-cure for 660HNu concentrations equal to or below 0.05%. Thus, these concentrations can be used to provide a visible indication of a complete/successful cure to the clinician. Conversely, remnant green/blue color is observed in the 0.1% 660HNu samples post-cure.

Conclusion:

Using an additional initiator and coinitiator along with a far red wavelength has an effect on the microhardness of cured composite. At too high of a concentration, it can actually have an adverse effect on the hardness of the bottom side, potentially because energy is absorbed by the initiators before it can reach this depth. However, a concentration can be selected that will improve the microhardness compared to using blue light alone. In particular, the addition of 0.005% 660H-Nu and 0.05% BorateV to commercially available dental composites, and subsequent curing using 660 nm and blue (e.g. 470 nm) light would result in a harder composite post-cure.

Example 10. Far Red or Near Infrared Dye Additive+Housing Material

To enhance the absorption of the dental material housing in the far red or near IR wavelengths, and thus improve the conversion of applied photon energy to temperature rise of dental material, a plastic with a NIR dye was evaluated according to the following; the results of which are shown graphically in FIG. 25.

Methods:

An NIR LED (940 nm LZ1 LedEngin powered at 1 A) was used to heat various plastic materials of similar thickness. A thermocouple was adhered to the plastic on the side opposite exposure to the LED emission, centered over the LED. The LED was activated for 30 seconds, and an additional 30 seconds of temperature data were recorded after the LED was turned off. Materials tested were poly (methyl methacrylate) (PMMA) (clear, orange, black and white colored), polycarbonate (PC) embedded with NIR absorbing dye (resulting plastic was clear orange in appearance), and two commercialized composite compules (black and blue colored).

Results:

Heating curves for the materials are shown in FIG. 25. Both the rate of change and peak temperature change are greater for the PC with the NIR dye. Of the other materials, the black composite compule was the next best for heating, but the peak temperature was 60% lower than that of the PC with NIR dye.

Conclusion:

Adding an NIR dye to plastic material improves the efficiency of the deposited NIR photon energy to be converted into a temperature rise.

Figure 14:
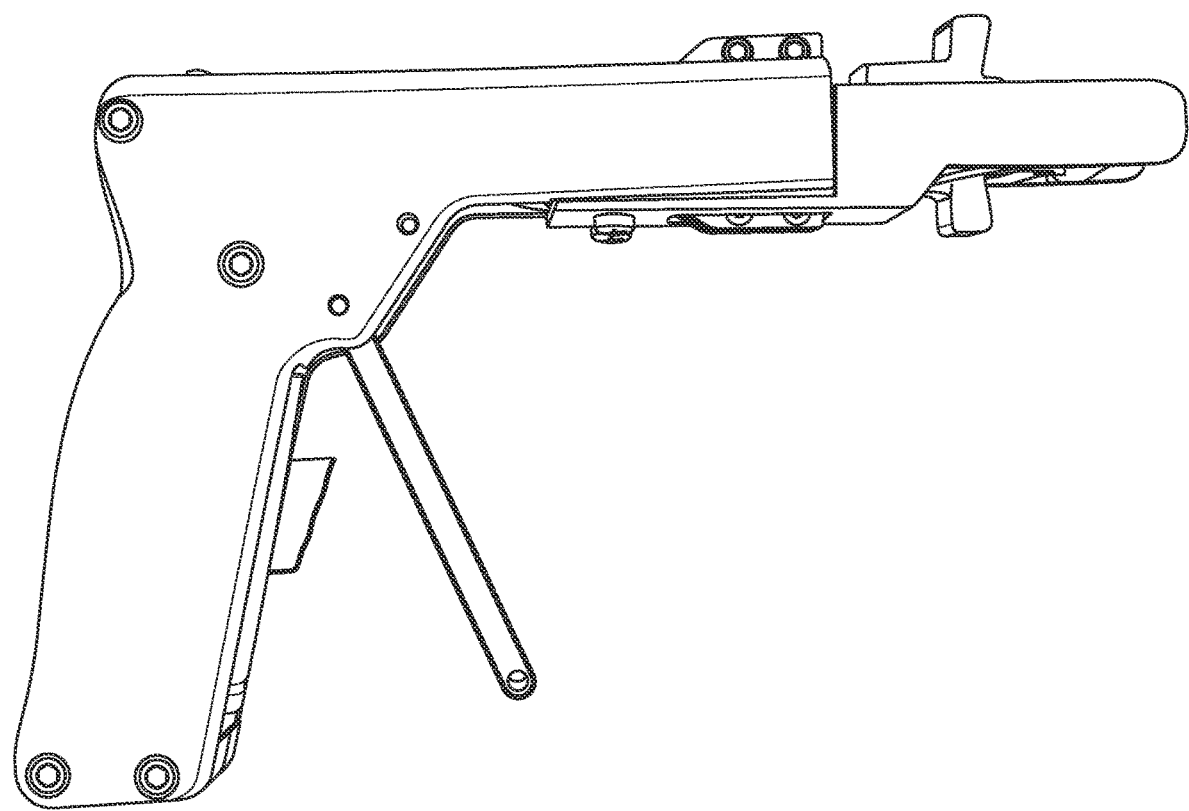
FIG. 14 is an isometric view of a delivery device according to one exemplary embodiment of the invention.
Figure 15:
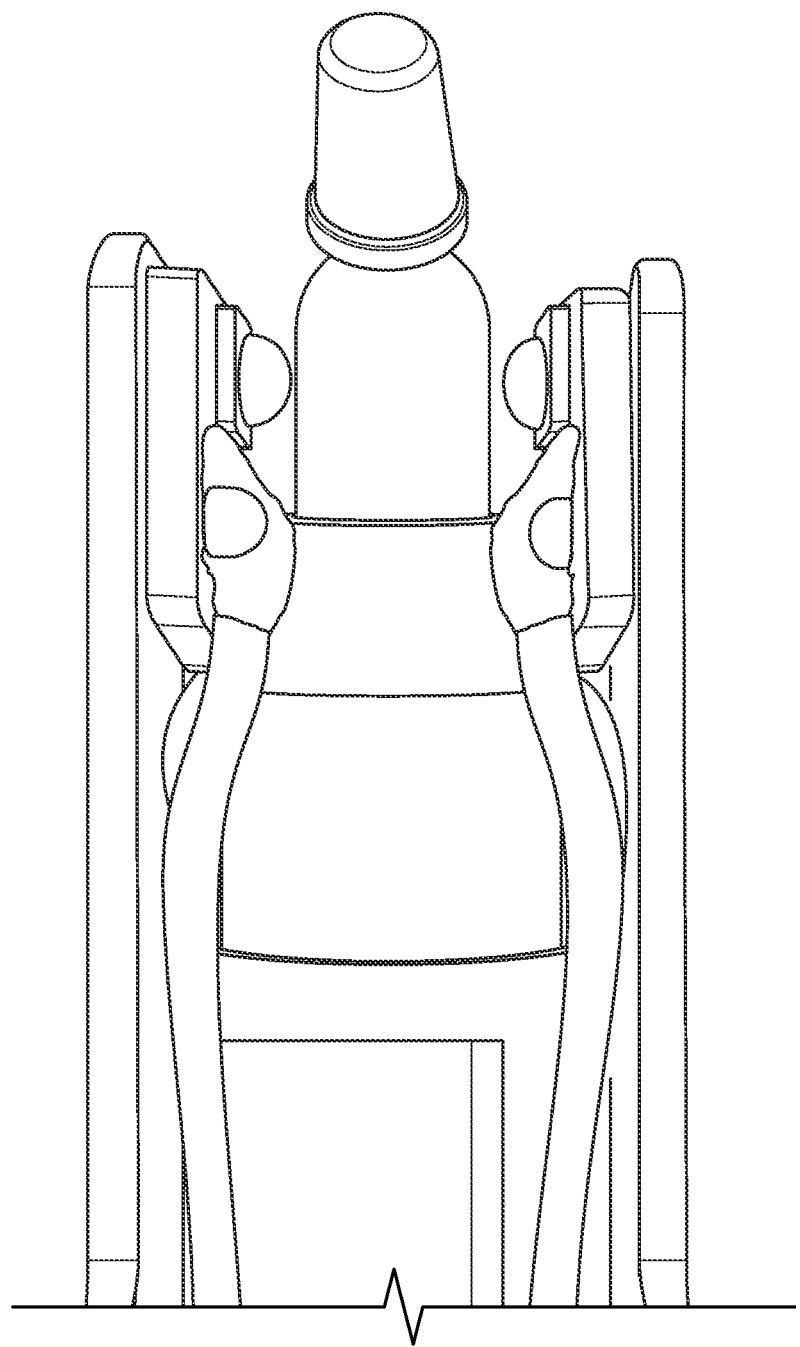
FIG. 15 is a partially broken away bottom plan view of a dispensing tip and compule of the device of FIG. 14 showing retention of the compule and spatial orientation of the photon energy sources directed towards the dental container containing a photopolymerizable dental material.
Figure 16:
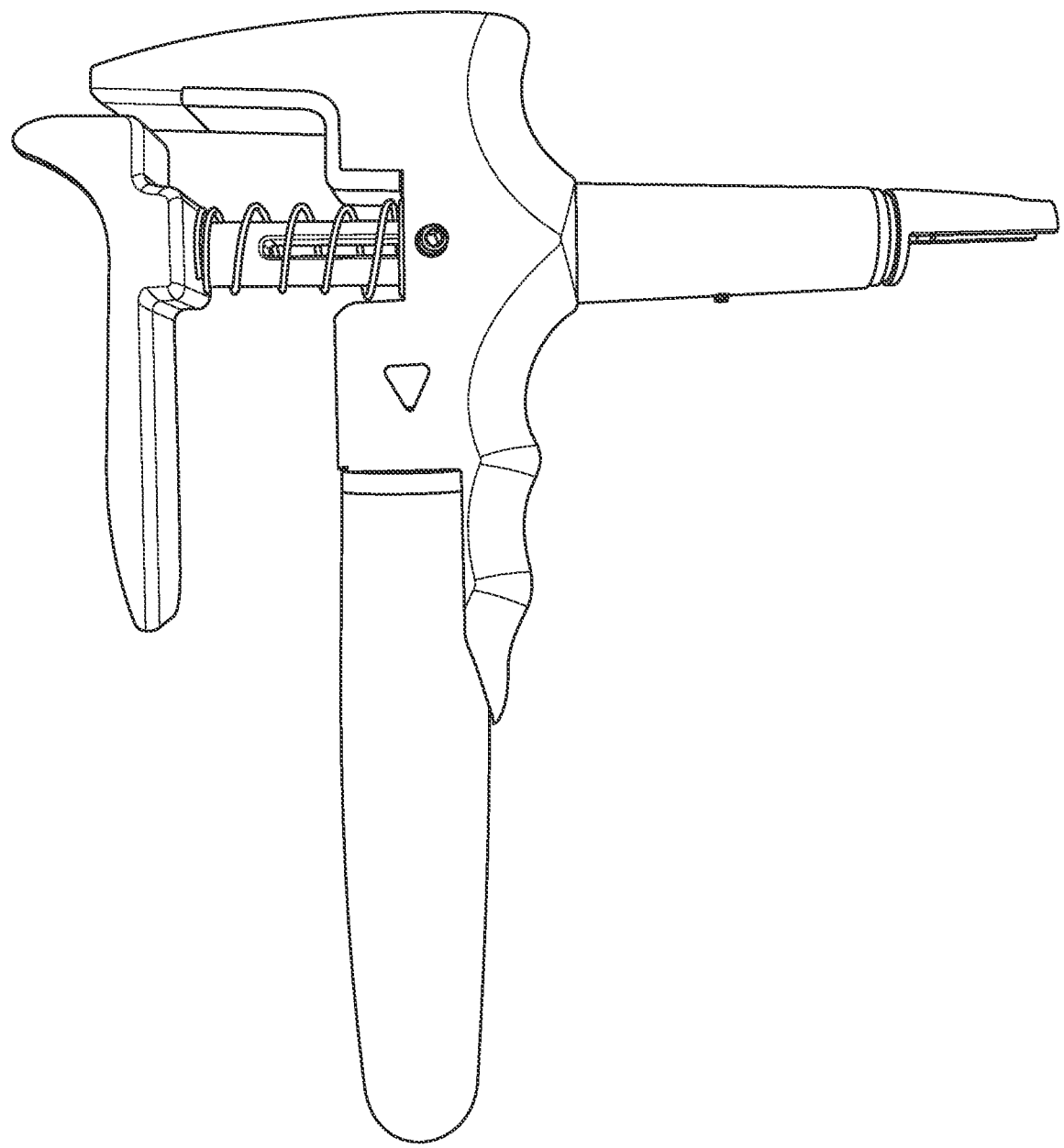
FIG. 16 is an isometric view of a delivery device according to another exemplary embodiment of the invention.

Example 11. Devices for the Heating of Dental Material Compositions and Application of Dental Material Compositions, and Devices for the Heating of Dental Material Compositions and Curing of Dental Photopolymerizable Compositions Described herein are example embodied devices for performing the application of the dental material, for example dental composite. One exemplary embodiment of a dispensing or delivery device is illustrated in FIGS. 14-15. The device has a body including a handle and an actuator or trigger that operates to dispense the composite form the device. The actuator can additionally be formed as a spring-biased grip as shown in FIG. 16. As shown in FIG. 15, the body can also include a light-emitter that emits near IR light/photon energy and a compule is further releasably attached to the body adjacent to the emitter such that light from the emitter strikes the compule and/or a dental material contained therein. The light/photons from the emitter strike the compule and/or dental material and affect the dental material by heating the material to the desired temperature and subsequently the trigger is operated to dispense the dental material from the compule. When exhausted, the compule can be disengaged from the body and a new compule attached thereto to heat and dispense additional dental material using the device. The body can further include an internal power source (not shown) such as a battery, such that the device is cordless. Alternatively, the device can be connected to a suitable exterior power source (not shown) such as via a plug (not shown) operably connected to the device and releasably engageable with the power source.

The device may further include or be formed as a curing light source (not shown) that can be operated consecutively or simultaneously with the near IR emitter, where the IR emitter can be a part of the curing device. The device also includes suitable actuators or buttons for the activation of the emitter and/or light source. In addition, the device may include or be formed as a curing light source (not shown) that can be operated consecutively or simultaneously with the near IR emitter, where the IR emitter can be a part of the curing device.

Referring to FIG. 28, one exemplary embodiment of a dispensing or delivery device is illustrated. The device 1 has a main outer body including an outer side housing 2, a hand held grip 3 for holding the device, a base 4, an actuator 5, a top housing 6, and a removable autoclavable sleeve 7 overlaying a removable compule 8 that is capable of containing a dental material described herein. The grip 3 further includes a removable rechargeable energy source door 9 having a holding clip 11. The top housing 6 further overlays one or more LED indicators 12 and the device further contains an on/off button or switch 13.

Referring to FIG. 29, which shows another side perspective of device 1 described above and a distal tip portion 14 of the device. As shown the distal tip portion 14 contains a compule 8 that is overlayed by autoclavable sleeve 7. Compule 8 is attached distal to a plunger 16, which extends into compule 8 after depressing actuator 5 releasing a dental material from orifice 15.

Referring now to FIGS. 30 and 31 are side sagittal perspectives of device 1 with outer side housing 2 and autoclavable sleeve 7 removed. As shown, the device contains a main printed circuit board (PCB) 24 that is in connection with rechargeable energy source 25. PCB 24 is further connected to a wire or wire ribbon 23 that is connected to a secondary PCB 18 having one or more control sensors 20 and one or more photon energy emitters 21 mounted thereto. Overlaying the photon energy emitters 21 is a lens 17, such that the photon energy emitters 21 are in close proximity (e.g., less than 1 cm) to compule 8. As described herein, the one or more photon energy emitters 21 emit photon energy that is absorbed by one or more components of a dental material contained in compule 8 causing it to heat. Additionally, as described herein, the one or more photon energy emitters 21 emit photon energy that is absorbed by one or more components of a dental material container, such as a compule 8, causing the dental material container to heat and thereby heat the dental material contained therein. Secondary PCB 18 may also function as a primary heat sink for the one or more photon energy emitters 21 mounted thereto. In addition, overlaying secondary PCB 18 is a secondary heat sink 19, which may comprise a portion of the overlaying device top housing 6 or nose cone bottom 18. FIG. 30 bottom image shows a side sagittal perspective of distal tip portion 14 of the device as described above.

Referring now to FIG. 32 is shown an expanded version of the device. As shown is an outer side housing 2L (left side housing) and 2R (right side housing), top housing 6, a nose cone bottom 22, a hand held grip 3 for holding the device, base 4, a rechargeable energy source door 9 having a holding clip 11 on the right and left side, an actuator 5, removable autoclavable sleeve 7, and LED indicators 12. Also shown is plunger 16 hingedly connected to actuator 5 extending distally to compule 8. Further shown is main PCB 24 having at least one photon energy emission emitter source 21 connected to a rechargeable energy source 25 via a connected wire or wire ribbon 23. Secondary PCB 18 is shown having multiple photon energy emitters 21 mounted thereto and disconnected from wire or wire ribbon 23. Lens 17 that overlays the one or more photon emitters 21 is shown in close proximity (e.g., less than 1 cm) to compule 8.

FIGS. 17-19 and 35 are embodiments of packages of photon emitters (i.e. LEDs) that can be incorporated for the disclosed multispectral device described herein that emits at least two discrete emission spectra for curing the dental composite and for the application of photon energy for heating. In one aspect, the LEDs can reside on two separate PCBs and be either on the same plane or a different plane. Although not shown in these figures, the 2 different emission sources can be placed on the same PCB and reside on the same plane, or lastly a single LED package can be created that incorporated multiple die(s) for the emission of different spectra. In one aspect, the various photon energy sources (i.e. LEDs) are on separate PCBs on separate planes as illustrated in FIGS. 17-19 and 35 as this configuration allows for improved collimation and illumination of the light/photon energy compared to multiple dies on the same LED package. Specifically, in one aspect, a configuration entails three LEDs oriented in a clover configuration (i.e. spaced 120° apart) on a PCB that is located in an elevated position relative to another PCB containing one LED (see FIGS. 17 and 35). This configuration allows for closer spacing of the LEDs for easier collimation of the LEDs' spectral radiation patterns using smaller sized optical components (e.g. reflector, collimator, etc) and an even illumination field.

Figure 17:
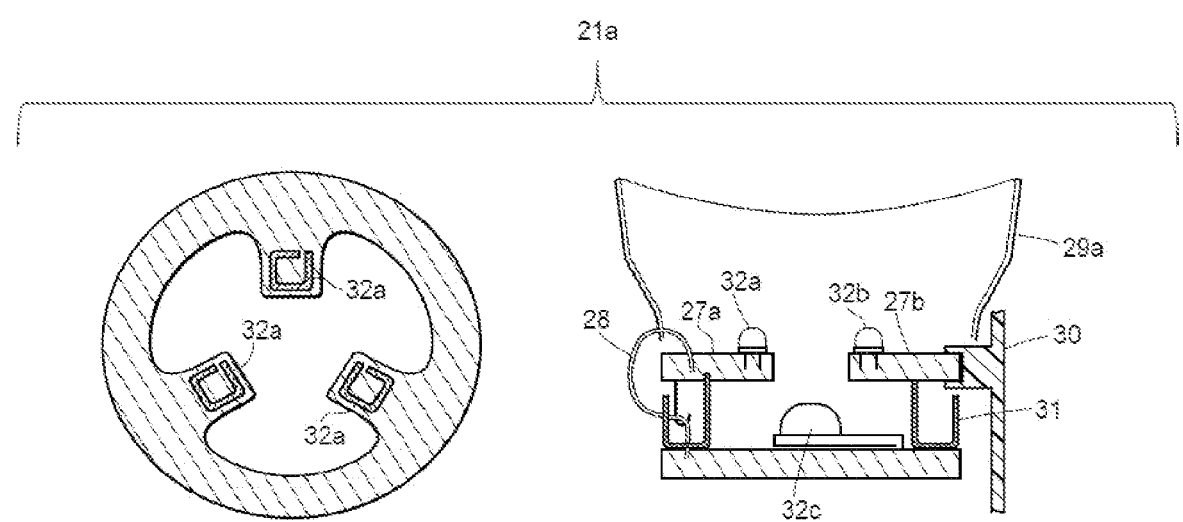
FIG. 17 is an exemplary embodiment of a package consisting of at least three photon energy emitters (i.e. LEDs) for use in a multispectral device, which emits at least two discrete emission spectra to cure dental composite materials and for the application of photon energy for heating. The left image is a top view of the package showing the orientation of three photon energy emitters (i.e. LEDs) on a clover shape PCB. The right image is a cross-section of the package showing the centrally located photon energy emitter 32c (i.e. LED) located on a plane parallel to the clover PCB; here two of the three LEDs located on the clover PCB are shown.
Figure 18:
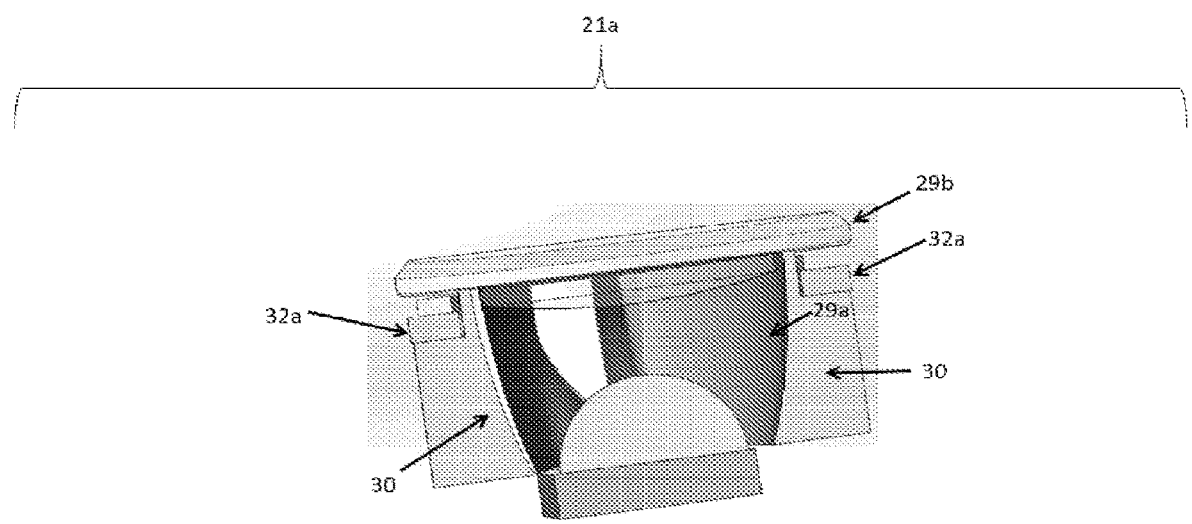
FIG. 18 is an exemplary embodiment of a package of photon emitters for use in a multispectral device that emits at least two discrete emission spectra for curing dental composite materials and for the application of photon energy for heating.
Figure 19:
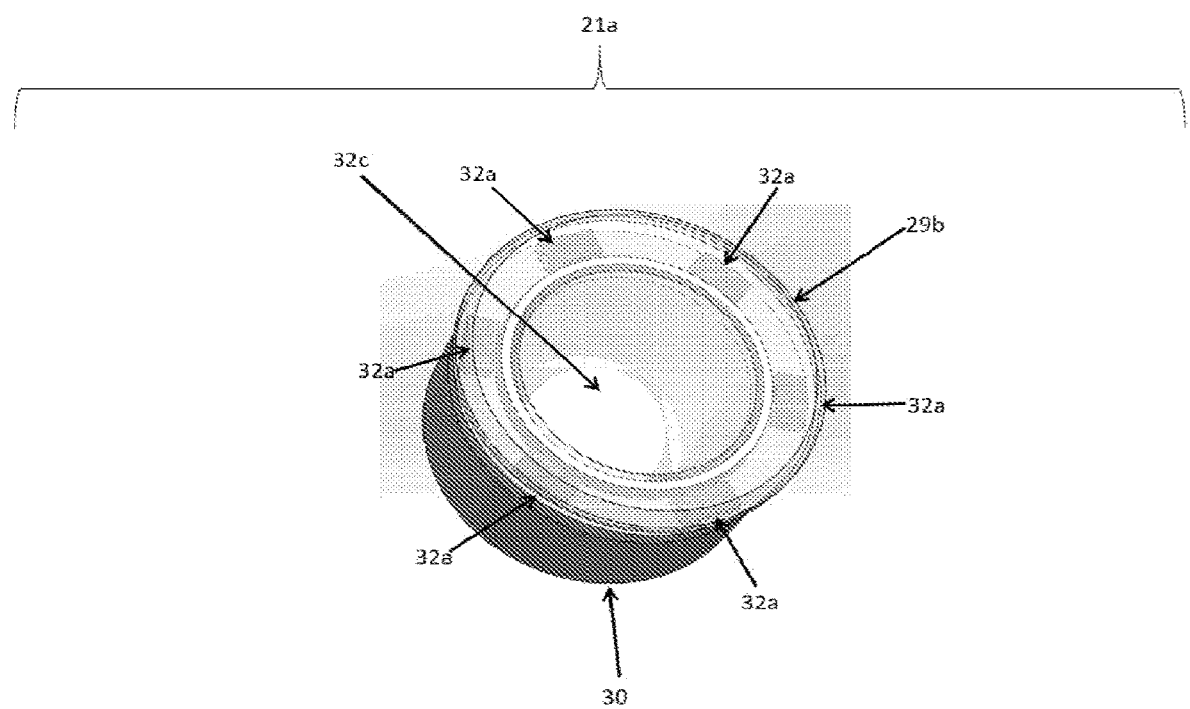
FIG. 19 is an exemplary embodiment of a package of photon emitters for use in a multispectral device, which emits at least two discrete emission spectra for curing dental composite materials and for the application of photon energy for heating.

Further detailing the embodied LED configurations and referring to FIGS. 17-19, the light or photon emission portion of the multispectral device 38 can include different sets of photon emitters 21a which can be placed on the same printed circuit board (PCB) and reside on the same plane, or they can reside on two separate PCB and be either on the same plane or a different plane, or lastly a single LED package can be created that incorporated multiple die(s) for the emission of different wavelengths of light or photons of different energies.

In FIG. 17, the multispectral device 38 further includes a collimator body or device housing 30 for the emitter(s) 21a that enclose LEDs 32a, 32b, and 32c, where the LEDs 32a, 32b, and 32c are mounted on the same or different PCB 27a and 27b that can be disposed in different planes. LEDs 32a, 32b, and 32c must emit at least two distinct emission spectra, wherein at least one emission spectra is within the specified photon energy range. The LEDs 32a, 32b, and 32c are disposed within the collimator body or device housing 30 in alignment with a collimator surface 29a to direct the light and/or photons out of the collimator body or device housing 30 where desired through a lens 29b. In FIGS. 17 and 18 the LEDs 32a are located around the exterior of the collimator body or device housing 30, with the LED 32c disposed within collimator body or device housing 30 as illustrated in the embodiment of FIG. 17.

Another embodied device is shown in FIGS. 33 and 34, which is a multispectral device 38 for curing and/or heating a dental material. Device 38 includes a central photon energy emitter (i.e. an LED) 35 with three radially placed photon energy emitters (i.e. LEDs) 34. The central photon energy emitter 35 is placed on a primary heat sink that is coupled to the thermally conductive main body 41. The three radially placed photon energy emitters 34 are placed on a separate primary heat sink that is parallel to the central photon energy emitter's 35 primary heat sink and is also coupled to the thermally conductive main body 41. Device 38 may optionally include an optical transilluminator 39. Device 38 includes a PCB 43, button 42, detachable and rechargeable battery pack 44, and rotation knob 40 for selecting a mode of operation.

Referring now to FIG. 35 is shown a setup 33 for inclusion within the multispectral device 38. The setup 33 contains 3 radially positioned photon energy emitters (i.e. LEDs) 34 on heat sink/PCB 36, around central LED 35 that is attached to separate heat sink/PCB 37 which is parallel to the other heat sink/PCB 36. Both heat sinks are coupled to the thermally conductive main body 41. In this example, the four LEDs 34 and 35 emit at least two distinctly different spectra; at least one spectra is used to elevate the photopolymerizable material above ambient temperature and at least one spectra is used to cure the photopolymerizable material.

The following statements are illustrative and within the scope of the embodiments of the invention described herein.

Statement 1. A method of treating a tooth of a subject in need thereof comprising:
heating a dental photopolymerizable material above ambient temperature with a device having a photon energy emission source that emits a photon energy that:
does not photopolymerize the material,
is absorbed by the dental photopolymerizable material, a dental photopolymerizable material container, or a heating additive, and
increases one or more properties comprising:
energy conversion efficiency from photon energy to heat or,
heating rate of the dental photopolymerizable material; and
applying the heated dental photopolymerizable material to a tooth surface cavity.

Statement 2. The method according to statement 1, wherein the photon energy increases the heating rate of a dental photopolymerizable material compared to heating the dental photopolymerizable material without photon energy.

Statement 3. The method according to any one of statements 1-2, wherein the device emits a photon energy of about 0.49 eV-2.38 eV (2500 nm-520 nm).

Statement 4. The method according to any one of statements 1-3, wherein the device emits a photon energy of about 1.23 eV-2.06 eV (1000 nm-600 nm).

Statement 5. The method according to any one of statements 1-4, wherein the dental photopolymerizable material is heated to a temperature of about 50° C. to about 250° C.

Statement 6. The method according to any one of statements 1-5, wherein the dental photopolymerizable material is heated to a temperature of about 60° C. to about 80° C.

Statement 7. The method according to any one of statements 1-6, further comprising curing the dental photopolymerizable material.

Statement 8. The method according to any one of statements 1-7, wherein the dental photopolymerizable material comprises composite resins, highly filled composite resins, glass ionomer resins, sealants, cements, cavity liners, or combinations thereof.

Statement 9. The method according to any one of statements 1-8, further comprising curing the dental photopolymerizable material by applying a second source of photon energy that emits a wavelength suitable for absorption by the photopolymerizable material to initiate polymerization.

Statement 10. The method according to any one of statements 1-9, wherein an applied photon energy for heating the dental photopolymerizable material does not overlap with an absorbance of a photoinitiator present in the dental photopolymerizable material.

Statement 11. The method according to any one of statements 1-10, wherein the dental photopolymerizable material or the dental photopolymerizable material container further comprises a heating additive, a thermal conductivity enhancer, or a polymerization enhancer, or combinations of the same.

Statement 12. The method according to any one of statements 1-11, wherein the heating additive is a dye having an absorption spectra that overlaps with an emission spectra of the photon energy emitted from the photon energy source.

Statement 13. The method according to any one of statements 11-12, wherein the thermal conductivity enhancer is an additive that improves the thermal conductivity of the dental photopolymerizable material or the dental photopolymerizable material container.

Statement 14. The method according to any one of statements 11-13, wherein the thermal conductivity enhancer is selected from graphite fibers, graphene flakes, ceramic particles, metal oxides, metal particles, carbon nanotubes, and combinations of the same.

Statement 15. The method according to any one of statements 1-14, wherein the photon energy that is at an absorption wavelength of the dental photopolymerizable material or a dental photopolymerizable material container is emitted during a curing step or just prior to a curing step of the dental photopolymerizable material.

Statement 16. The method according to any one of statements 1-15, wherein the application of the photon energy that is at an absorption wavelength of the dental photopolymerizable material or a dental photopolymerizable material container increases one or more post-cure properties of the dental photopolymerizable material, selected from degree-of-conversion and hardness, compared to a dental photopolymerizable material that has not been heated with the photon energy that is at an absorption wavelength of the dental photopolymerizable material or a dental photopolymerizable material container.

Statement 17. The method according to any one of statements 1-16, wherein the application of the photon energy that is at an absorption wavelength of the dental photopolymerizable material or a dental photopolymerizable material container stimulates one or more photochemical effects selected from: photodegradation, photobleaching, or photocatalysis of the dental photopolymerizable material.

Statement 18. A photopolymerizable dental composition comprising:
  unreacted monomer(s),
  filler(s),
  at least one photoinitiator, and
  a heating additive that increases one or more properties comprising: the energy conversion efficiency from photon energy to heat or increasing a heating rate of the dental photopolymerizable material, wherein the heating additive does not impart an unnatural tooth color to the photopolymerizable dental composition after photopolymerization.

Statement 19. The composition of statement 18, wherein the heating additive and the at least one photoinitiator are activated by distinctly different photon energy spectra.

Statement 20. The composition according to any one of statements 18-19, wherein the heating additive comprises one or more of the following properties: a high absorbance between 0.49 eV-2.38 eV (2500 nm-520 nm), compatible with a dental photopolymerizable material, stable at temperatures greater than room temperature, soluble and dispersible within the dental photopolymerizable material, does not negatively affect a dental photopolymerizable material performance, or has a high conversion efficiency from photon energy to heat or a combination of properties thereof.

Statement 21. The composition according to any one of statements 18-20, wherein the heating additive comprises a photon energy absorption enhancer or a thermal conductivity enhancer or a combination thereof.

Statement 22. The composition according to statement 21, wherein the photon energy absorption enhancer is present in the dental photopolymerizable material at a concentration of up to about 10% by weight of the dental photopolymerizable material.

Statement 23. The composition according to any one of statements 21-22, wherein the photon energy absorption enhancer is present in the dental photopolymerizable material at a concentration of about 0.001% to about 0.5%.

Statement 24. The composition according to any one of statements 21-23, wherein an area-intersection of a normalized absorbance spectra of the photon energy absorption enhancer and a normalized emission spectra of a photon energy source is at least 10% of an area-under-the-curve for either spectra.

Statement 25. The composition according to statement 24, wherein the area-intersection of the normalized absorbance spectra of the photon energy absorption enhancer and a normalized emission spectra of the photon energy source is at least 25% of an area-under-the-curve for either spectra.

Statement 26. The composition according to any one of statements 24-25, wherein the area-intersection of the normalized absorbance spectra of the photon energy absorption enhancer and a normalized emission spectra of the photon energy source is at least 50% of an area-under-the-curve for either spectra.

Statement 27. The composition according to any one of statements 21-26, wherein the thermal conductivity enhancer is an additive that improves the thermal conductivity of the dental photopolymerizable material.

Statement 28. The composition according to any one of statements 21-27, wherein the thermal conductivity enhancer is selected from: graphite particles, graphene particles, ceramic particles, metal oxide particles, metal particles, carbon nanotubes, and combinations thereof.

Statement 29. The composition according to any one of statements 21-28, wherein the thermal conductivity enhancer is present in the dental photopolymerizable material at a concentration of about of 0.01% to about 90% by weight of the dental photopolymerizable material.

Statement 30. The composition according to any one of statements 21-29, wherein the thermal conductivity enhancer is present in the dental photopolymerizable material at a concentration of about of 1% to about 10% by weight of the dental photopolymerizable material.

Statement 31. The composition according to any one of statements 18-30, wherein the composition further comprises a polymerization enhancer consisting of a photoinitiator or a co-initiator or a combination thereof.

Statement 32. The composition of statement 31, wherein the polymerization enhancer increases a photopolymerization of a photopolymerizable monomer present in the dental photopolymerizable material.

Statement 33. The composition according to any one of statements 31-32, wherein the polymerization enhancer increases one or more properties consisting of: improving polymerization, improving depth-of-cure, improving degree-of-conversion using photon energy, and combinations of properties thereof.

Statement 34. The composition according to any one of statements 18-33, wherein the heating additive comprises a dye, which exhibits an absorbance between 0.49 eV-2.38 eV (2500 nm-520 nm).

Statement 35. The composition of statement 18-34, wherein the dye comprises about 0.001% to about 10% by weight of the composition.

Statement 36. The composition according to any one of statements 18-35, wherein the composition comprises:
a. an unreacted acrylate monomer comprising about 5-30% by weight;
b. an inorganic filler comprising about 60-95% by weight;
c. a photoinitiator comprising about 0.001-0.5% by weight;
d. a co-initiator comprising about 0.001-1% by weight; and
e. a dye, which exhibits an absorbance between 0.49 eV-2.38 eV (2500 nm-520 nm) comprising about 0.001-10% by weight.

Statement 37. The composition according to any one of statements 18-36, wherein the composition comprises:
a. an unreacted acrylate monomer comprising 40-90% by weight;
b. an inorganic filler comprising 1-20% by weight;
c. a photoinitiator comprising 0.001-0.5% by weight;
d. a co-initiator comprising 0.001-0.5% by weight; and
e. a dye, which exhibits an absorbance between 0.49 eV-2.38 eV (2500 nm-520 nm) comprising 0.001-10% by weight.

Statement 38. A method of treating a tooth of a subject in need thereof comprising heating the composition of any one of statements 18-37 with a device having a photon energy emission source that emits a photon energy that is at an absorption wavelength of the composition or a heating additive present in the composition and applying the heated composition to a surface of the tooth.

Statement 39. A dental composition, comprising polyisoprene, inorganic filler(s), radiopacifier, wax(es) or resin(s), and a heating additive that increases one or more properties comprising: energy conversion efficiency from photon energy to heat or increasing a heating rate of the dental composition.

Statement 40. The composition of statement 39, wherein the polyisoprene comprises natural or synthetic gutta percha.

Statement 41. The composition according to any one of statements 39-40, wherein the polyisoprene comprises about 10% to about 30% by weight of the composition.

Statement 42. The composition according to any one of statements 39-41, wherein the filler comprises about 50% to about 85% by weight of the composition.

Statement 43. The composition according to any one of statements 39-42, wherein the radiopacifier comprises about 1% to about 35% by weight of the composition.

Statement 44. The composition according to any one of statements 39-43, wherein the wax(es) or resin(s) comprise about 1% to about 10% by weight of the composition.

Statement 45. The composition according to any one of statements 39-44, wherein the heating additive comprises about 0.001% to about 10% by weight of the composition.

Statement 46. The composition of according to any one of statements 39-45, wherein the composition comprises:
a. natural gutta percha or synthetic gutta percha comprising about 10-30% by weight of the composition;
b. an inorganic filler comprising about 50-85% by weight of the composition;
c. a radiopacifier comprising about 1-35% by weight of the composition;
d. a wax or resin comprising about 0-10% by weight of the composition; and
e. a heating additive, which exhibits an absorbance between 0.49 eV-2.38 eV (2500 nm-520 nm) comprising about 0.001-10% by weight of the composition.

Statement 47. A method of treating a tooth of a subject in need thereof comprising heating the composition of any one of statements 39-46 with a device having a photon energy emission source that emits a photon energy that is at an absorption wavelength of the composition or a heating additive present in the composition and applying the heated composition to a surface of the tooth.

Statement 48. A photopolymerizable dental composition comprising:
unreacted monomer(s),
filler(s),
at least two photoinitiators, wherein at least one of the two photoinitiators is activated by photon energy within a range of 0.49 eV-1.90 eV (2500 nm-650 nm), and at least one of the other photoinitiator(s) is activated by photon energy outside this photon energy range,
at least one co-initiator, wherein the at least one co-initiator consists of a borate derivative; and
wherein the photoinitiators do not impart an unnatural tooth color to the photopolymerizable dental composition after photopolymerization.

Statement 49. The composition of statement 48, wherein the two photoinitiators comprise a type I or a type II photoinitiator or a combination thereof.

Statement 50. The composition of any one of statements 48-49, wherein the photopolymerizable material comprises two type II photoinitiators.

Statement 51. The composition according to any one of statements 48-50, wherein the photoinitiator that is activated by photon energy within the range of 0.49 eV-1.90 eV (2500 nm-650 nm) enhances photopolymerization.

Statement 52. The composition according to any one of statements 48-51, wherein the photoinitiator that is activated by photon energy within the range of 0.49 eV-1.90 eV (2500 nm-650 nm) is present at a concentration of about 0.0001% to about 0.5% by weight of the composition.

Statement 53. The composition according to any one of statements 48-52, wherein the photoinitiator that is activated by photon energy within the range of 0.49 eV-1.90 eV (2500 nm-650 nm) is present at a concentration of about 0.001% to about 0.1% by weight of the composition.

Statement 54. The composition according to any one of statements 48-53, wherein the borate derivative is borate V.

Statement 55. The composition according to any one of statements 48-54, wherein the borate derivative is at least 10 times more concentrated than the at least one photoinitiator that is activated by photon energy within the range of 0.49 eV-1.90 eV (2500 nm-650 nm).

Statement 56. The composition according to any one of statements 48-55, wherein the photoinitiator that is activated by photon energy within the range of 0.49 eV-1.90 eV (2500 nm-650 nm) is photobleached and/or is consumed during a photopolymerization process occurring at 0.49 eV-1.90 eV (2500 nm-650 nm) to reduce its visible color.

Statement 57. The composition according to any one of statements 48-56, wherein the photoinitiator that is activated by photon energy within the range of 0.49 eV-1.90 eV (2500 nm-650 nm) promotes material curing by increasing radical formation and simultaneously bleaches as formed radicals deplete providing a visible change to indicate complete curing.

Statement 58. The composition according to any one of statements 48-57, wherein the composition comprises:
a. an unreacted acrylate monomer comprising about 5-30% by weight;
b. an inorganic filler comprising about 60-95% by weight;
c. a first photoinitiator comprising about 0.001-0.5% by weight;

d. a second photoinitiator, which exhibits an absorbance between 0.49 eV-1.90 eV (2500 nm-650 nm), comprising about 0.001-0.5% by weight; and
e. a borate derivative co-initiator comprising about 0.01-5% by weight.

Statement 59. The composition according to any one of statements 48-58, wherein the composition comprises:
a. an unreacted acrylate monomer comprising 40-90% by weight;
b. an inorganic filler comprising 1-20% by weight;
c. a first photoinitiator comprising 0.001-0.5% by weight;
d. a second photoinitiator, which exhibits an absorbance between 0.49 eV-1.90 eV (2500 nm-650 nm), comprising 0.001-0.5% by weight; and
e. a borate derivative co-initiator comprising 0.01-5% by weight.

Statement 60. A method of treating a tooth of a subject in need thereof comprising heating the composition of any one of statements 48-59 with a device having a photon energy emission source that emits a photon energy that is at an absorption wavelength of the composition or a photoinitiator present in the composition and applying the heated composition to a surface of the tooth.

Statement 61. A material container comprising a thermoplastic resin and at least one photon energy absorption enhancer additive forming the container that increases one or more properties comprising:
increasing energy conversion efficiency from photon energy to heat, or
increasing a heating rate of the material contained within,
wherein the at least one photon energy absorption enhancer additive has an optical density value greater than 1 for photon energy between 0.49 eV-2.38 eV (2500 nm-520 nm) after thermoplastic injection molding.

Statement 62. The container of statement 61, wherein the container further comprises a pigment, a colorant, a plasticizer, or a filler, or a combination thereof.

Statement 63. The container according to any one of statements 61-62, wherein the container comprises an additional photon energy absorption enhancer additive, or at least one thermal conductivity enhancer, or combinations thereof as an integral part of the container.

Statement 64. The container according to statement 63, wherein the photon energy absorption enhancer additive is present in the container at a concentration of about 0.01% to about 20% by weight of a dental photopolymerizable material container.

Statement 65. The container according to any one of statements 63-64, wherein the photon energy absorption enhancer additive is present in the container at a concentration of about of 0.1% to about 5% by weight of a dental photopolymerizable material container.

Statement 66. The container according to any one of statements 61-65, wherein an area-intersection of a normalized absorbance spectra of the photon energy absorption enhancer additive and a normalized emission spectra of a photon energy source is at least 10% of an area-under-the-curve for either spectra.

Statement 67. The container according to statement 66, wherein the area-intersection of the normalized absorbance spectra of the photon energy absorption enhancer additive and a normalized emission spectra of the photon energy source is at least 25% of an area-under-the-curve for either spectra.

Statement 68. The container according to any one of statements 66-67, wherein the area-intersection of the normalized absorbance spectra of the photon energy absorption enhancer additive and a normalized emission spectra of the photon energy source is at least 50% of an area-under-the-curve for either spectra.

Statement 69. The container according to any one of statements 63-68, wherein the thermal conductivity enhancer is an additive that improves the thermal conductivity of the dental material container.

Statement 70. The container according to any one of statements 63-69, wherein the thermal conductivity enhancer is selected from: graphite particles, graphene particles, ceramic particles, metal oxide particles, metal particles, carbon nanotubes, and combinations thereof.

Statement 71. The container according to any one of statements 63-70, wherein the thermal conductivity enhancer is present in the housing at a concentration of about 0.1% to about 50% by weight.

Statement 72. The composition according to any one of statements 63-71, wherein the thermal conductivity enhancer is present in a dental photopolymerizable material container at a concentration of about 1% to about 10% by weight of the dental photopolymerizable material container.

Statement 73. The container according to any one of statements 61-72, wherein the housing sufficiently blocks light from transmitting through the container to a dental photopolymerizable material housed therein, thereby preventing the dental photopolymerizable material from being cured within the container.

Statement 74. The container according to any one of statements 61-73, wherein the thermoplastic resin comprises about 50% to about 95% by weight of the container.

Statement 75. The container according to any one of statements 61-74, wherein the photon energy absorption enhancer additive comprises about 0.1% to about 50% by weight of the composition.

Statement 76. The container according to any one of statements 61-75, wherein the container comprises the thermoplastic resin comprising about 95% by weight of the container and the heating additive comprising about 5% by weight of the container.

Statement 77. A method of treating a tooth of a subject in need thereof comprising heating the container of any one of statements 61-76, wherein the container comprises a dental material, wherein the container is heated with a device having a photon energy emission source that emits photon energy that is at an absorption wavelength of the container or a heating additive present in the container, or the dental material housed in the container and applying the heated dental material to a surface of the tooth.

Statement 78. A container for holding a dental material according to any one of statements 61-77 made by a process comprising:
a). heating a thermoplastic resin to at least its softening point;
b). maintaining and controlling the resin temperature to at least its softening point;
c). adding an additive at about 0.1-5%, that has a high photon energy absorbance between 520 nm-2500 nm, and optionally a dispersant while maintaining and controlling the resin temperature to at least it softening point;
d). mixing the mixture of a-c while maintaining temperature to at least the resin's softening point to homogenize the mixture; and
e). extruding the heated mixture of a-d into a mold cavity comprising the dental material container shape and allowing it to cool prior to removal from the cavity.

Statement 79. A container for holding a dental material according to any one of statements 61-77 made by a process comprising:
   a). heating a thermoplastic resin to at least its softening point;
   b). maintaining and controlling the resin temperature to at least its softening point;
   c). adding an additive at about 0.1-5%, that has a high photon energy absorbance between 520 nm-2500 nm, and optionally a dispersant while maintaining and controlling the resin temperature to at least it softening point;
   d). mixing the mixture of a-c while maintaining temperature to at least the resin's softening point to homogenize the mixture; and
   e). making pellets from the mixture of a-d that can be later used for injection molding a dental material container.

Statement 80. The container according to any one of statements 61-79, wherein the made container is filled with a dental material.

Statement 81. A device for heating a dental material and applying the heated dental material to a tooth surface or cavity comprising:
   a. a body;
   b. a plunger mounted movably within the body for engaging with a dental material container;
   c. an actuation means connected to the plunger to controllably dispense the dental material from the dental material container;
   d. a distally mounted photon energy emission source, wherein the photon energy emission source consists of a electroluminescence source that produces between 0.5 watts and 20 watts of optical power;
   e. a rechargeable power source, wherein the electroluminescence source is in electrical communication with the rechargeable power source;
   f. a primary heat sink located within the device body or constitutes a part of the device body, wherein the electroluminescence source is coupled to the primary heat sink located; and
   g. a receptacle on the device body for securably receiving the dental material container, such that the dental material container is held within close proximity to the electroluminescence source.

Statement 82. The device according to statement 81, wherein the photon energy source is capable of emitting photon energy between 0.49 eV-2.38 eV (i.e. 2500 nm-520 nm).

Statement 83. The device according to any one of statements 81-82, wherein the photon energy emission source emits photon energy between 1.24 eV-1.77 eV (i.e. 1000 nm-700 nm).

Statement 84. The device according to any one of statements 81-83, wherein the electroluminescence source comprises a light emitting diode (LED) or a laser diode or a combination thereof.

Statement 85. The device according to any one of statements 81-84, wherein the electroluminescence source is less than about 1 cm from a dental material container having a dental material therein.

Statement 86. The device according to any one of statements 81-85, wherein the device further comprises a collimator comprising a lens or fiber optic for increasing the photon energy irradiance to the container having the dental material.

Statement 87. The device according to any one of statements 81-86, wherein the primary heat sink is coupled to a secondary heat sink contained within the device, or that comprises part of the housing of the device, wherein the secondary heat sink prevents the device from reaching an unsafe elevated temperature above 50° C.

Statement 88. The device according to any one of statements 81-87, wherein the primary heat sink or secondary heat sink is coupled to a heat pipe, wherein the heat pipe prevents the device from reaching an elevated temperature.

Statement 89. The device according to any one of statements 81-88, further comprising a heat sensor, wherein the heat sensor prevents the device from reaching an elevated temperature, which may degrade the dental material or may pose a danger to an operator or a patient being treated with the device; wherein the heat sensor is indirectly capable of monitoring the temperature of the dental material and reducing or removing power output of the photon energy source.

Statement 90. The device according to any one of statements 81-89, further comprising a loop control feedback system for maintaining a desired temperature without reaching undesirable temperatures, which may degrade the dental material or may pose a danger to an operator or a patient being treated with the device.

Statement 91. The device according to any one of statements 81-90, further comprising an absorption sensor for determining the absorption characteristics of a dental material or dental material container, wherein the sensor provides an output for adjusting power and/or duration of the photon energy source for achieving a desired temperature of the dental material.

Statement 92. The device according to any one of statements 81-91, further comprising an additional light source for curing dental photopolymerizable materials.

Statement 93. The device according to any one of statements 81-92, wherein the additional light source emits a light at a wavelength of about 365 nm-500 nm.

Statement 94. The device according to any one of statements 81-93, wherein the additional light source for curing dental photopolymerizable materials emits between 500 mW and 3 W of optical power.

Statement 95. The device according to any one of statements 81-94, wherein the additional light source for curing dental photopolymerizable materials a emits between 700 mW and 1.5 W of optical power.

Statement 96. The device according to any one of statements 81-95, wherein the photon energy emission output leads, lags, or is simultaneously used with the photon energy emission output of the additional light source for curing dental photopolymerizable materials.

Statement 97. The device according to any one of statements 81-96, wherein the curing light and photon energy sources are arranged distally on the device for access to an oral cavity of a patient.

Statement 98. A handheld multispectral device for enhancing the cure of photopolymerizable dental materials, the device comprising:
   a. a thermally conductive body;
   b. at least four discrete distally mounted photon energy emission source(s) that produce at least two discrete emission spectra, wherein;
     a. one photon energy source is centrally located, and at least three photon energy sources are located radially about the centrally located photon energy source;
     b. the output of the centrally located photon energy emission source leads, lags, or is simultaneously used with the output of the at least three radially located photon energy emission sources;
     c. at least one emission spectra is used for curing the photopolymerizable dental material, and at least one emission spectra is used to elevate the photopolymerizable dental material's temperature above ambient temperature during curing;

d. the at least four photon energy emission sources consists of light emitting diodes;

c. the at least four discrete photon energy emission sources are coupled to at least one primary heat sink located within the device body;

d. the at least one primary heat sink is coupled to the thermally conductive body; and e. the light emitting diodes are in electrical communication to a direct current power source.

Statement 99. The device according to statement 98, wherein the direct current power source comprises a detachable, rechargeable power source.

Statement 100. The device according to any one of statements 98-99, wherein at least three radially mounted LEDs are arranged on a primary heat sink around the centrally located LED, which is on a separate primary heat sink, to provide a near uniform beam profile and illumination field.

Statement 101. The device according to any one of statements 98-100, wherein the at least four LEDs are collimated to produce about a 1 cm spot size at a distance between 1-10 mm.

Statement 102. The device according to any one of statements 98-101, wherein the at least one photon energy emission source for curing the photopolymerizable dental material emits light between 365 nm-500 nm at an optical power of between 500 mW and 3 W.

Statement 103. The device according to any one of statements 98-102, wherein the at least one photon energy emission source for elevating the photopolymerizable dental material's temperature above ambient temperature during curing emits light between 520 nm-2500 nm at a power between 500 mW and 3 W of optical power. 104. A method of treating a tooth of a subject in need thereof comprising heating a dental composite material or a container comprising the dental composite material with the device according to any one of any one of statements 81-103.

Although the invention herein has been described in connection with described embodiments thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

What is claimed is:

1. A method of treating a tooth of a subject in need thereof comprising:

heating a dental photopolymerizable material above ambient temperature with a device having a photon energy emission source that emits a photon energy that:
    does not photopolymerize the material,
    is absorbed by a dental photopolymerizable material container and increases one or more properties comprising:
        energy conversion efficiency from photon energy to heat or,
        heating rate of the dental photopolymerizable material; and
    applying the heated dental photopolymerizable material to a tooth surface cavity.

2. The method according to claim 1, wherein the photon energy increases the heating rate of the dental photopolymerizable material compared to heating the dental photopolymerizable material without photon energy.

3. The method according to claim 1, wherein the device emits a photon energy of about 0.49 eV-2.38 eV (2500 nm-520 nm).

4. The method according to claim 1, wherein the device emits a photon energy of about 1.23 eV-2.06 eV (1000 nm-600 nm).

5. The method according to claim 1, wherein the dental photopolymerizable material is heated to a temperature of about 50° C. to about 250° C.

6. The method according to claim 1, wherein the dental photopolymerizable material is heated to a temperature of about 60° C. to about 80° C.

7. The method according to claim 1, further comprising curing the dental photopolymerizable material.

8. The method according to claim 1, wherein the dental photopolymerizable material comprises composite resins, highly filled composite resins, glass ionomer resins, sealants, cements, cavity liners, or combinations thereof.

9. The method according to claim 1, further comprising curing the dental photopolymerizable material by applying a second source of photon energy that emits a wavelength suitable for absorption by the photopolymerizable material to initiate polymerization.

10. The method according to claim 1, wherein an applied photon energy for heating the dental photopolymerizable material does not overlap with an absorbance of a photoinitiator present in the dental photopolymerizable material.

11. The method according to claim 1, wherein the dental photopolymerizable material or the dental photopolymerizable material container further comprises a heating additive, a thermal conductivity enhancer, or a polymerization enhancer, or combinations of the same.

12. The method according to claim 11, wherein the thermal conductivity enhancer is an additive that improves the thermal conductivity of the dental photopolymerizable material or the dental photopolymerizable material container.

13. The method according to claim 11, wherein the thermal conductivity enhancer is selected from: graphite fibers, graphene flakes, ceramic particles, metal oxides, metal particles, carbon nanotubes, and combinations of the same.

14. The method according to claim 1, wherein the heating additive is a dye having an absorption spectra that overlaps with an emission spectra of the photon energy emitted from the photon energy source.

15. The method according to claim 1, wherein the photon energy that is at an absorption wavelength of the dental photopolymerizable material or a dental photopolymerizable material container is emitted during a curing step or just prior to a curing step of the dental photopolymerizable material.

16. The method according to claim 1, wherein the application of the photon energy that is at an absorption wavelength of the dental photopolymerizable material or a dental photopolymerizable material container increases one or more post-cure properties of the dental photopolymerizable material, selected from: degree-of-conversion and hardness, compared to a dental photopolymerizable material that has not been heated with the photon energy that is at an absorption wavelength of the dental photopolymerizable material or a dental photopolymerizable material container.

17. The method according to claim 1, wherein the application of the photon energy that is at an absorption wavelength of the dental photopolymerizable material or a dental photopolymerizable material container stimulates one or more photochemical effects selected from: photodegradation, photobleaching, or photocatalysis of the dental photopolymerizable material.

\* \* \* \* \*